United States Patent
Ihn et al.

(10) Patent No.: US 10,297,764 B2
(45) Date of Patent: May 21, 2019

(54) MIXTURE, THIN FILM, AND ORGANIC LIGHT EMITTING DEVICE INCLUDING MIXTURE AND THIN FILM

(71) Applicants: SAMSUNG ELECTRONICS CO., LTD., Suwon-si, Gyeonggi-do (KR); Samsung SDI Co., Ltd., Yongin-si, Gyeonggi-do (KR)

(72) Inventors: Sooghang Ihn, Hwaseong-si (KR); Hosuk Kang, Suwon-si (KR); Jhunmo Son, Yongin-si (KR); Namheon Lee, Suwon-si (KR); Jongsoo Kim, Suwon-si (KR); Joonghyuk Kim, Seoul (KR); Myungsun Sim, Suwon-si (KR); Youngmok Son, Hwaseong-si (KR); Soonok Jeon, Seoul (KR); Dalho Huh, Suwon-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 269 days.

(21) Appl. No.: 15/262,584

(22) Filed: Sep. 12, 2016

(65) Prior Publication Data
US 2017/0077421 A1 Mar. 16, 2017

(30) Foreign Application Priority Data

Sep. 14, 2015 (KR) .................. 10-2015-0129774
Mar. 7, 2016 (KR) .................. 10-2016-0027140

(51) Int. Cl.
*H01L 51/50* (2006.01)
*H01L 51/00* (2006.01)
(Continued)

(52) U.S. Cl.
CPC ........ *H01L 51/0072* (2013.01); *C07D 209/86* (2013.01); *C07D 209/88* (2013.01);
(Continued)

(58) Field of Classification Search
None
See application file for complete search history.

(56) References Cited

U.S. PATENT DOCUMENTS 5,955,836 A 9/1999 Boerner et al.
8,993,129 B2 3/2015 Endo et al.
(Continued)

FOREIGN PATENT DOCUMENTS

JP 2000-133453 A 5/2000
JP 2009-277838 A 11/2009
(Continued)

OTHER PUBLICATIONS

Shin et. al., Blue Phosphorescent Organic Light-Emitting Diodes Using an Exciplex Forming Co-host with the External Quantum Efficiency of Theoretical Limit, 2014, Advanced Materials, 26, 4730-4734 (Year: 2014).*
(Continued)

*Primary Examiner* — Gregory D Clark
(74) *Attorney, Agent, or Firm* — Cantor Colburn LLP

(57) ABSTRACT

A composition including a donor compound and an acceptor compound, wherein the donor compound and the acceptor compound form an exciplex having characteristics described in the specification.

26 Claims, 9 Drawing Sheets

(51) Int. Cl.
*C07D 209/86* (2006.01)
*C07D 209/88* (2006.01)
*C09K 11/02* (2006.01)
*C09K 11/06* (2006.01)
*H01L 51/52* (2006.01)

(52) U.S. Cl.
CPC ............ *C09K 11/02* (2013.01); *C09K 11/06* (2013.01); *H01L 51/0055* (2013.01); *H01L 51/5012* (2013.01); *C09K 2211/1007* (2013.01); *C09K 2211/1011* (2013.01); *C09K 2211/1029* (2013.01); *H01L 51/5004* (2013.01); *H01L 51/5028* (2013.01); *H01L 51/5206* (2013.01); *H01L 51/5221* (2013.01); *H01L 2251/552* (2013.01)

(56) References Cited

U.S. PATENT DOCUMENTS

| | | |
|---|---|---|
| 2005/0221116 A1 | 10/2005 | Cocchi et al. |
| 2008/0220287 A1 | 9/2008 | Dotz et al. |
| 2010/0037285 A1 | 2/2010 | Cain |
| 2012/0217869 A1 | 8/2012 | Adachi et al. |
| 2014/0367647 A1* | 12/2014 | Kim .................. H01L 51/0085 257/40 |
| 2015/0069352 A1 | 3/2015 | Kim et al. |
| 2016/0190478 A1 | 6/2016 | Nakanotani et al. |

FOREIGN PATENT DOCUMENTS

| | | |
|---|---|---|
| JP | 2010-040036 A | 2/2010 |
| KR | 10-2014-0092710 A | 7/2014 |
| KR | 10-1419810 B1 | 7/2014 |
| WO | 2015-022974 A1 | 2/2015 |
| WO | 2015-041157 A1 | 3/2015 |
| WO | 2015041157 A1 | 3/2015 |

OTHER PUBLICATIONS

Bo Zhao et al. "Highly efficient tandem full exciplex orange and warm white OLEDs based on thermally activated delayed fluorescene mechanism", Organic Electronics 17 (2015) 15-21.

Extended Search Report dated Jan. 26, 2017, issued by the European Patent Office for European Patent Application No. 16188366.5-1555.

Hyun Shin et al. "Blue Phosphorescent Organic Light-Emitting Diodes Using an Exciplex Forming Co-host with the External Quantum Efficiency of Theoretical Limit", Adv. Mater. 2014, 26, 4730-4734.

Jin Won Sun et al. "A Fluorescent Organic Light-Emitting Diode with 30% External Quantum Efficiency", Adv. Mater. 2014, 26, 5684-5688.

* cited by examiner

MIXTURE, THIN FILM, AND ORGANIC LIGHT EMITTING DEVICE INCLUDING MIXTURE AND THIN FILM

CROSS-REFERENCE TO RELATED APPLICATIONS

This application claims priority to Korean Patent Applications No. 10-2015-0129774, filed on Sep. 14, 2015 and No. 10-2016-0027140, filed on Mar. 7, 2016, in the Korean Intellectual Property Office, and all the benefits accruing therefrom under 35 U.S.C. § 119, the contents of which are incorporated herein in their entirety by reference.

BACKGROUND

1. Field

The present disclosure relates to a composition, a thin film, and an organic light-emitting device.

2. Description of the Related Art

Organic light-emitting devices (OLEDs) are self-emission devices that have wide viewing angles, high contrast ratios, and short response times. In addition, OLEDs have excellent brightness, driving voltage, and response speed characteristics, compared to devices in the art, and produce full-color images.

Typical OLEDs include an anode, a cathode, and an organic layer that is disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transit from an excited state to a ground state to thereby generate light.

Various types of organic light emitting devices are known. However, there still remains a need in OLEDs having low driving voltage, high efficiency, high brightness, and long lifespan.

SUMMARY

Provided are a composition that may include an exciplex that meets specific conditions, a thin film including the composition, and organic light-emitting device including the composition, which has a low driving voltage, high emission efficiency, high luminance, and long lifespan.

Additional aspects will be set forth in part in the description which follows and, in part, will be apparent from the description, or may be learned by practice of the presented embodiments.

According to an aspect of an embodiment, a composition includes:

a donor compound and an acceptor compound, wherein the donor compound and the acceptor compound form an exciplex, wherein a maximum emission wavelength $\lambda_{max}$(Ex) in a photoluminescence spectrum of the exciplex is about 390 nanometers or greater and about 490 nanometers or less, wherein a decay time $T_{decay}$(Ex) of delayed fluorescence in a time-resolved photoluminescence spectrum of the exciplex is about 100 nanoseconds or greater, wherein a ratio of a delayed fluorescence portion to the overall light-emitting portions in the time-resolved photoluminescence spectrum of the exciplex is about 10% or greater, wherein a photoluminescence stability of the exciplex is 59% or greater, wherein the photoluminescence spectrum and the time-resolved photoluminescence spectrum of the exciplex are each a spectrum measured at room temperature with respect to a film that is formed by co-deposition of the donor compound and the acceptor compound on a substrate, and wherein the photoluminescence stability of the exciplex is calculated according to Equation 10:

$$\text{PL stability (\%)} = (I_2/I_1) \times 100 \qquad \text{Equation 10}$$

wherein, in Equation 10, $I_1$ is an intensity of a light at the maximum emission wavelength $\lambda_{max}$(Ex) in a photoluminescence spectrum of Film 1, which is obtained immediately after formation of a film by co-deposition of the donor compound and the acceptor compound on a substrate, measured at room temperature in an inert atmosphere in which external air is excluded, and $I_2$ is an intensity of a light at the maximum emission wavelength $\lambda_{max}$(Ex) in a photoluminescence spectrum of Film 2, which is obtained after exposure of the Film 1 to pumping laser light used in the evaluation of $I_1$ in an inert atmosphere in which external air is excluded for 3 hours, measured at room temperature in an inert atmosphere in which external air is excluded.

According to an aspect of another embodiment, a thin film includes the composition.

According to an aspect of another embodiment, an organic light-emitting device includes:

a first electrode;

a second electrode; and an organic layer disposed between the first electrode and the second electrode, wherein the organic layer includes a thin film including the composition.

BRIEF DESCRIPTION OF THE DRAWINGS

These and/or other aspects will become apparent and more readily appreciated from the following description of the embodiments, taken in conjunction with the accompanying drawings in which.

Figure 1:
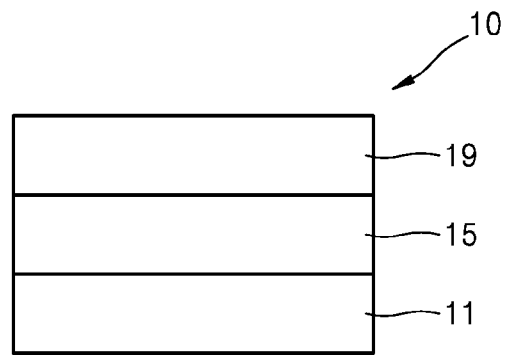
FIG. 1 is a schematic cross-sectional view of an organic light-emitting device according to an embodiment.

B3PYMPM, and TCTA:3TPYMB, and a PL spectrum ("3-hr exposed") measured after three-hour exposure to laser light.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

A composition (for example, a mixture) may include a donor compound and an acceptor compound, and the donor compound and the acceptor compound may form an exciplex. For example, the composition (for example, the mixture) may consist of a donor compound and an acceptor compound, and the donor compound and the acceptor compound may form an exciplex.

The donor compound may be an electron-donor compound in which electron donating properties are dominated over its electron accepting properties, and the acceptor compound may be an electron-acceptor compound in which electron accepting properties are dominated over its electron donating properties, wherein the donor compound may be a hole transport compound and wherein the acceptor compound may be an electron transport compound.

The exciplex may be an excited state complex formed between the donor compound and the acceptor compound.

In the composition, a maximum emission wavelength ($\lambda_{max}$(Ex)) of a photoluminescence (PL) spectrum of the exciplex may be about 390 nanometers (nm) or greater and about 490 nm or less, in some embodiments, about 390 nm or greater and about 450 nm or less, in some embodiments, about 390 nm or greater and about 440 nm or less, and in some embodiments, about 390 nm or greater and about 410 nm or less. When the maximum emission wavelength ($\lambda_{max}$(Ex)) of a photoluminescence (PL) spectrum of the exciplex is within the above ranges, the composition may emit blue light. For example, the composition may emit blue light having X coordinates in CIE color-coordinates in a range of about 0.182 to about 0.307 and Y coordinates in CIE color-coordinates in a range of about 0.092 to about 0.523. Thus, when the composition is used in an electronic device, e.g., an organic light-emitting device, the electronic device may emit blue light of high color purity.

In the composition, a decay time ($T_{decay}$(Ex)) of delayed fluorescence in a time-resolved photoluminescence (TRPL) spectrum of the exciplex may be about 100 nanoseconds (ns) or greater, in some embodiments, about 150 ns or greater, and in some embodiments, about 100 ns or greater and about 10 milliseconds (ms) or less. A ratio of a delayed fluorescence portion to the overall light-emitting portions in the TRPL spectrum of the exciplex may be about 10% or greater, and in some embodiments, about 15% or greater. Accordingly, up-conversion of the exciplex from a triplet state to a singlet state may efficiently occur, and thus the exciplex may emit high efficiency delayed fluorescence. Thus, when the composition is used, a high efficiency electronic device, for example, a high efficiency organic light-emitting device, may be realized.

The PL spectrum and the TRPL spectrum of the exciplex may each be a spectrum measured at room temperature with respect to a film that is formed by co-deposition of the donor compound and the acceptor compound on a substrate (e.g., a quartz substrate). This may be understood with reference to Examples and Evaluation Examples below.

The $T_{decay}$ (Ex) may be evaluated by using one or more suitable methods using a TRPL spectrum. For example, the $T_{decay}$(Ex) may be evaluated by using the method described in Evaluation Example 1, but embodiments are not limited thereto.

A ratio of the delayed fluorescence portion (DF portion) may be evaluated by using one or more suitable methods using a TRPL spectrum. For example, the ratio of the delayed fluorescence portion may be evaluated by using the method described in Evaluation Example 1, but embodiments are not limited thereto.

A PL stability of the exciplex of the composition may be about 59% or greater, in some embodiments, about 60% or greater, and in some embodiments, about 70% or greater. According to an embodiment, a PL stability of the exciplex of the composition may be about 80% or greater, and in some embodiments, about 90% or greater. While not wishing to be bound by theory, it is understood that when the exciplex of the composition has PL stability within these ranges, an organic light-emitting device employing the composition may have long lifespan.

The PL stability of the exciplex may be calculated according to Equation 10:

$$\text{PL stability (\%)} = (I_2/I_1) \times 100 \qquad \text{Equation 10}$$

wherein, in Equation 10, $I_1$ may be an intensity (arbitrary units, a.u.) of a light at the maximum emission wavelength ($\lambda_{max}$(Ex)) in a PL spectrum of Film 1, which is obtained immediately after formation of a film by co-deposition of the donor compound and the acceptor compound on a substrate, measured at room temperature in an inert atmosphere in which external air is excluded, and $I_2$ may be an intensity (arbitrary units, a.u.) of a light at the maximum emission wavelength ($\lambda_{max}$(Ex)) in a PL spectrum of Film 2, which is obtained after exposure of the Film 1 to pumping laser light used in the evaluation of $I_1$ in an inert atmosphere in which external air is excluded for 3 hours, measured at room temperature in an inert atmosphere in which external air is excluded.

An embodiment of the PL stability evaluation will be described with reference to Examples and Evaluation Examples.

According to an embodiment, an absolute value of the highest occupied molecular orbital (HOMO) energy level of the donor compound (|HOMO (D)|) may be about 5.78 electron volts (eV) or less, and in some embodiments, about 4.84 eV or greater and about 5.78 eV or less. According to an embodiment, an absolute value of the lowest unoccupied molecular orbital (LUMO) energy level of the acceptor compound (|LUMO (A)|) may be about 1.76 eV or greater, and in some embodiments, about 2.43 eV or less and about 1.76 eV or greater. Accordingly, exciplex formation efficiency in the composition may increase, and thus, an electronic device, e.g., an organic light-emitting device, including the composition may have improved efficiency and lifespan.

The HOMO (D) may be measured by using cyclic voltammetry (CV), and the LUMO (A) may be measured by using a UV absorption spectrum measured at room temperature. This will be understood with reference to Examples below.

In various embodiments, an absolute value of the HOMO energy level difference between the acceptor compound and the donor compound (|HOMO (A)–HOMO (D)–) may be about 0.037 eV or greater and about 1.1 eV or less, and in some embodiments, about 0.04 eV or greater and about 0.9 eV or less. In various embodiments, an absolute value of the LUMO energy level difference between the acceptor compound (|LUMO (A)–LUMO (D)|) and the donor compound may be about 0.001 eV or greater and about 1.1 eV or less, and in some embodiments, about 0.01 eV or greater and about 0.9 eV or less. Accordingly, hole migration through the donor compound and electron migration through the acceptor compound may efficiently occur, thus leading to efficient formation of an exciplex at an interface between the donor compound and the acceptor compound. Thus, an electronic device, e.g., an organic light-emitting device, including the composition may have improved efficiency and lifespan.

The donor compound may include at least one selected from a carbazole-containing ring, a dibenzofuran-containing ring, a dibenzothiophene-containing ring, an indenocarbazole-containing ring, an indolocarbazole-containing ring, a benzofurocarbazole-containing ring, a benzothienocarbazole-containing ring, an acridine-containing ring, a dihydroacridine-containing ring, and a tri-indolobenzene-containing ring, and the acceptor compound may include at least one selected from a carbazole-containing ring, a dibenzofuran-containing ring, a dibenzothiophene-containing ring, an indenocarbazole-containing ring, an indolocarbazole-containing ring, a benzofurocarbazole-containing ring, a benzothienocarbazole-containing ring, a pyridine-containing ring, a pyrimidine-containing ring, and a triazine-containing ring.

For example, the donor compound may not include an electron withdrawing group, and the acceptor compound may include at least one electron withdrawing group, wherein the electron withdrawing group may be selected from —F, —CFH$_2$, —CF$_2$H, —CF$_3$, —CN, and —NO$_2$;

a C$_1$-C$_{60}$ alkyl group substituted with at least one selected from —F, —CFH$_2$, —CF$_2$H, —CF$_3$, —CN, and —NO$_2$;

a C$_1$-C$_{60}$ heteroaryl group and a monovalent non-aromatic condensed polycyclic heterocyclic group, each including *=N—*' as a ring-forming moiety; and a C$_1$-C$_{60}$ heteroaryl group and a monovalent non-aromatic condensed polycyclic heterocyclic group, each including *=N—*' as a ring-forming moiety and each substituted with at least one selected from deuterium, —F, —CFH$_2$, —CF$_2$H, —CF$_3$, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_7$-C$_{60}$ arylalkyl group, a substituted or unsubstituted C$_1$-C$_{60}$ heteroaryl group, a substituted or unsubstituted C$_1$-C$_{60}$ heteroaryloxy group, a substituted or unsubstituted C$_1$-C$_{60}$ heteroarylthio group, a substituted or unsubstituted C$_2$-C$_{60}$ heteroarylalkyl group, a substituted or unsubstituted monovalent non-aromatic condensed polycyclic group, and a substituted or unsubstituted monovalent non-aromatic condensed heteropolycyclic group.

According to an embodiment, the donor compound may be selected from compounds represented by Formula D-1, and the acceptor compound may be selected from compounds represented by Formulae A-1 and A-2:

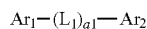

Formula D-1

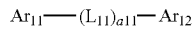

Formula A-1

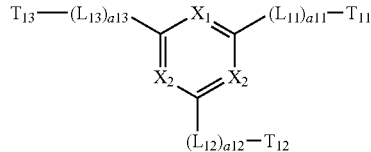

Formula A-2

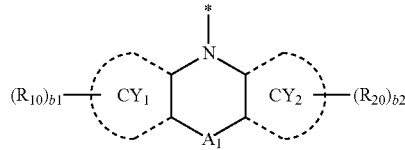

Formula 11

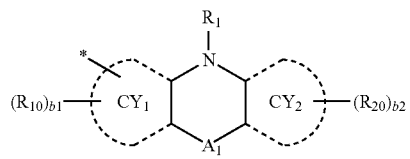

Formula 12

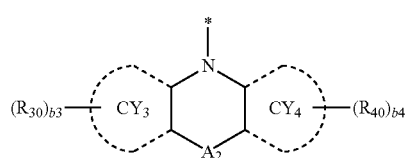

Formula 13

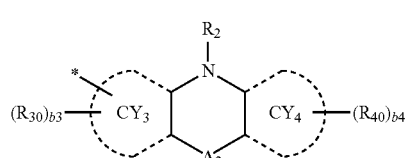

Formula 14 wherein, in Formulae D-1, A-1, A-2, and 11 to 14, $Ar_1$ may be selected from groups represented by Formulae 11 and 12, $Ar_2$ may be selected from groups represented by Formulae 11 and 12, a phenyl group, and a naphthyl group; and a phenyl group and a naphthyl group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, and a dibenzothiophenyl group, $Ar_{11}$ and $Ar_{12}$ may be each independently selected from groups represented by Formulae 13 and 14, $X_1$ may be N or $C(T_{14})$, $X_2$ may be N or $C(T_{15})$, and $X_3$ may be N or $C(T_{16})$, provided that at least one of $X_1$ to $X_3$ may be N, $L_1$ may be selected from a single bond, a phenylene group, a naphthylene group, a fluorenylene group, a carbazolylene group, a dibenzofuranylene group, and a dibenzothiophenylene group; and a phenylene group, a naphthylene group, a fluorenylene group, a carbazolylene group, a dibenzofuranylene group, and a dibenzothiophenylene group, each substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, and —Si$(Q_{11})(Q_{12})(Q_{13})$, $L_{11}$ to $L_{13}$ may be each independently selected from a single bond, a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group; and a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, —$CFH_2$, a phenyl group, a phenyl group substituted with a cyano group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —Si$(Q_{11})(Q_{12})(Q_{13})$, a1 and a11 to a13 may be each independently an integer selected from 0 to 5, when a1 is 2 or greater, groups $L_1$ may be identical to or different from each other, when a11 is 2 or greater, groups $L_{11}$ may be identical to or different from each other, when a12 is 2 or greater, groups $L_{12}$ may be identical to or different from each other, when a13 is 2 or greater, groups $L_{13}$ may be identical to or different from each other, $CY_1$ to $CY_4$ may be each independently selected from a benzene group, a naphthalene group, a fluorene group, a carbazole group, a benzocarbazole group, an indolocarbazole group, a dibenzofuran group, and a dibenzothiophene group, $A_1$ may be selected from a single bond, a $C_1$-$C_4$ alkylene group, and a $C_2$-$C_4$ alkenylene group; and a $C_1$-$C_4$ alkylene group and a $C_2$-$C_4$ alkenylene group, each substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, and —Si$(Q_{21})(Q_{22})(Q_{23})$, $A_2$ may be selected from a single bond, a $C_1$-$C_4$ alkylene group, and a $C_2$-$C_4$ alkenylene group; and a $C_1$-$C_4$ alkylene group and a $C_2$-$C_4$ alkenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —Si($Q_{21}$)($Q_{22}$)($Q_{23}$), $R_1$, $R_{10}$, and $R_{20}$ may be each independently selected from hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, and a dibenzothiophenyl group;

a phenyl group, a naphthyl group, a fluorenyl group, a carbazolyl group, a dibenzofuranyl group, and a dibenzothiophenyl group;

a phenyl group, a naphthyl group, a fluorenyl group, a carbazolyl group, a dibenzofuranyl group, and a dibenzothiophenyl group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, and a dibenzothiophenyl group; and
—Si($Q_1$)($Q_2$)($Q_3$), $T_{11}$ to $T_{16}$, $R_2$, $R_{30}$, and $R_{40}$ may be each independently selected from hydrogen, deuterium, —F, —Cl, —Br, —I, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$), b1 to b4 may be each independently an integer selected from 0 to 10, and at least one substituent of the substituted $C_1$-$C_{60}$ alkyl group, substituted $C_2$-$C_{60}$ alkenyl group, substituted $C_2$-$C_{60}$ alkynyl group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_1$-$C_{60}$ heteroaryloxy group, substituted $C_1$-$C_{60}$ heteroarylthio group, substituted $C_2$-$C_{60}$ heteroarylalkyl group, substituted monovalent non-aromatic condensed polycyclic group, and substituted monovalent non-aromatic condensed heteropolycyclic group may be selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, and —Si($Q_{31}$)($Q_{32}$)($Q_{33}$), wherein $Q_1$ to $Q_3$, $Q_{11}$ to $Q_{13}$, $Q_{21}$ to $Q_{23}$, and $Q_{31}$ to $Q_{33}$ may be each independently selected from hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, $Ar_1$ in Formula D-1 may be selected from groups represented by Formulae 11-1 to 11-8 and 12-1 to 12-8, $Ar_2$ in Formula D-1 may be selected from groups represented by Formulae 11-1 to 11-8 and 12-1 to 12-8, a phenyl group, and a naphthyl group, and $Ar_{11}$ and $Ar_{12}$ in Formula A-1 may be each independently selected from groups represented by Formulae 13-1 to 13-8 and 14-1 to 14-8:

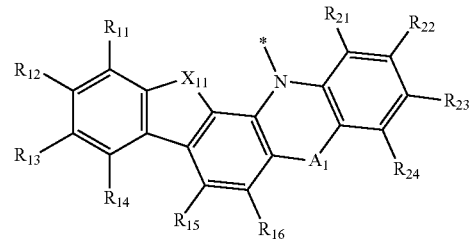

Formula 11-1

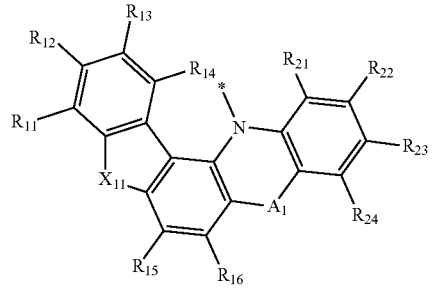

Formula 11-2

Formula 11-3
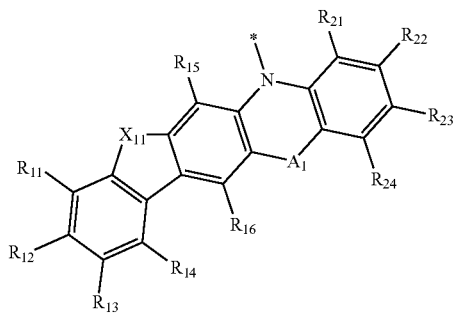
Formula 11-4
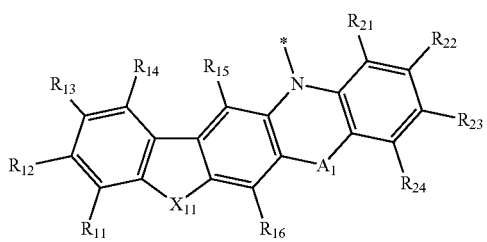
Formula 11-5
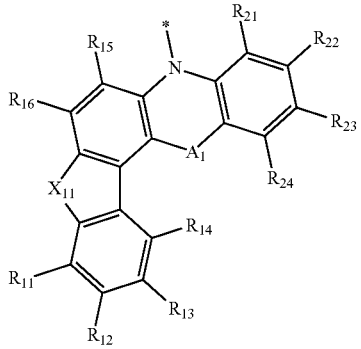
Formula 11-6
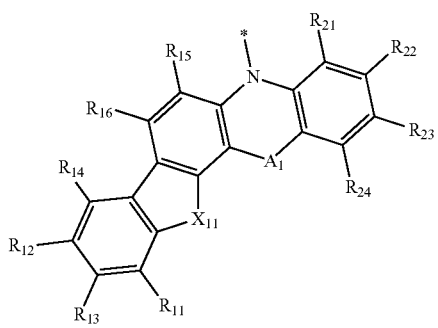
Formula 11-7
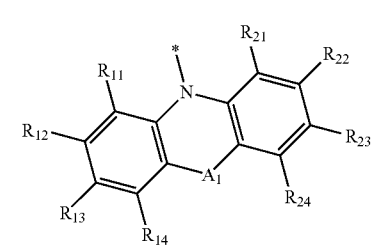
Formula 11-8
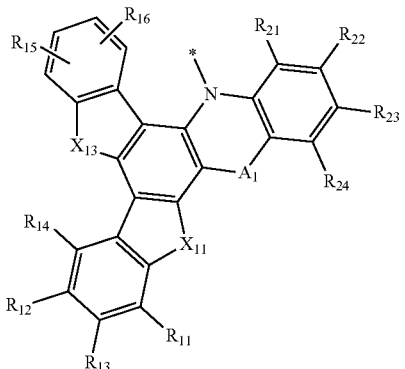
Formula 12-1
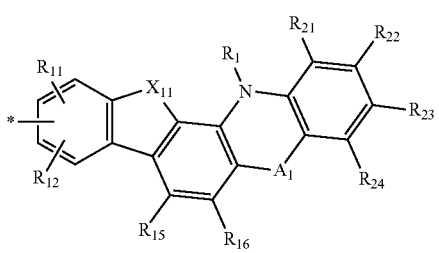
Formula 12-2
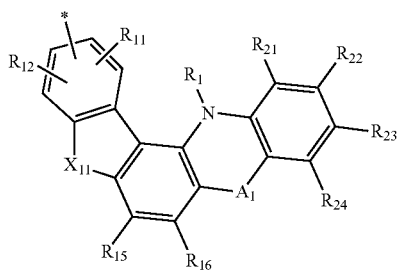
Formula 12-3
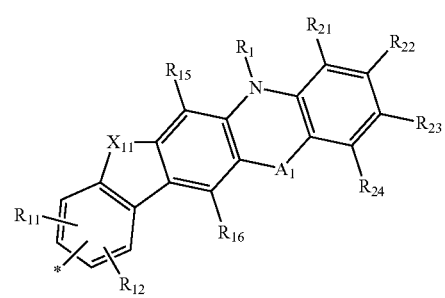
Formula 12-4

Formula 12-5
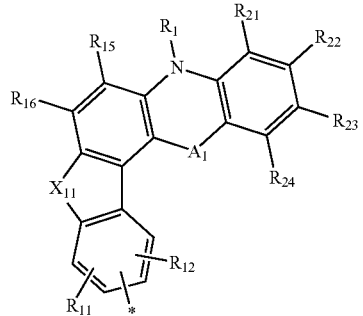
Formula 12-6
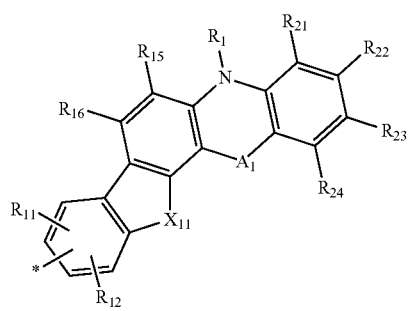
Formula 12-7
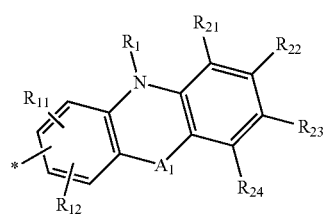
Formula 12-8
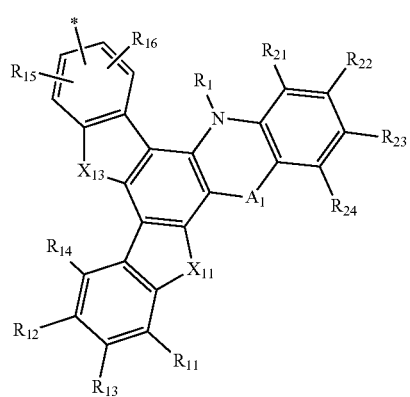
Formula 13-1
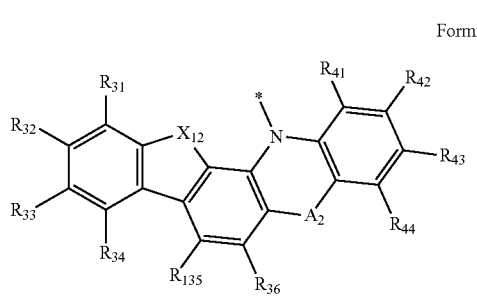
Formula 13-2
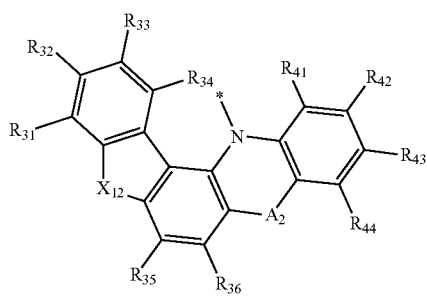
Formula 13-3
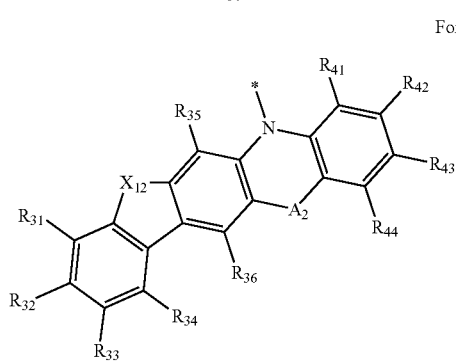
Formula 13-4
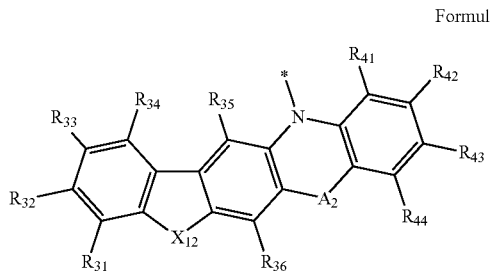
Formula 13-5
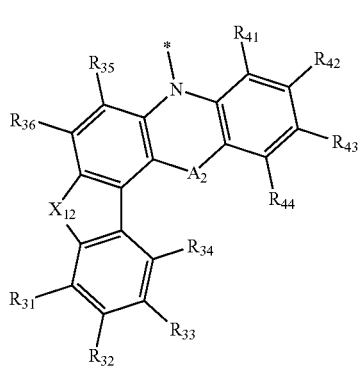
Formula 13-6
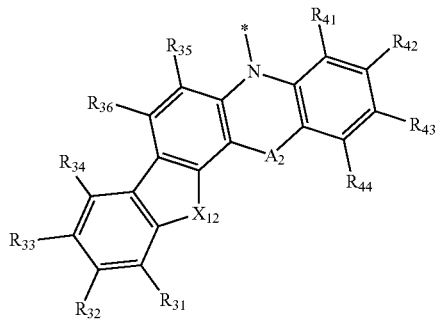

Formula 13-7
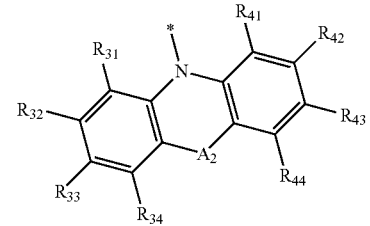
Formula 13-8
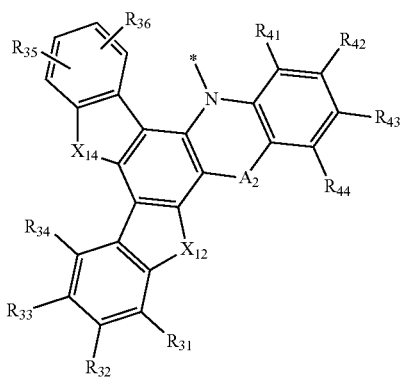
Formula 14-1
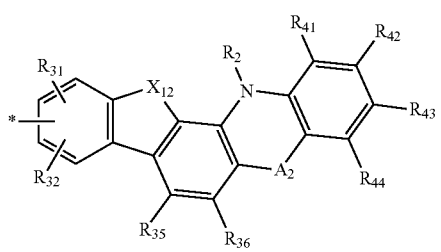
Formula 14-2
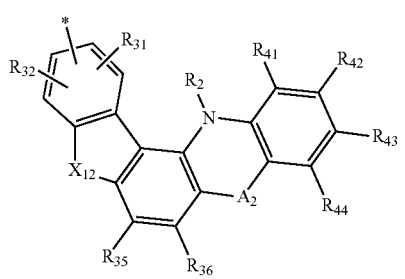
Formula 14-3
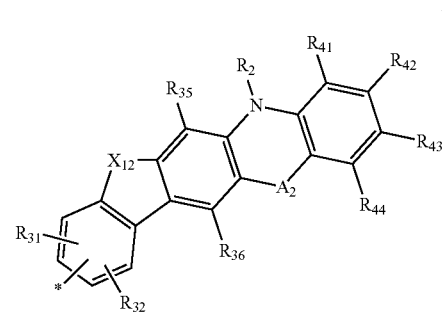
Formula 14-4
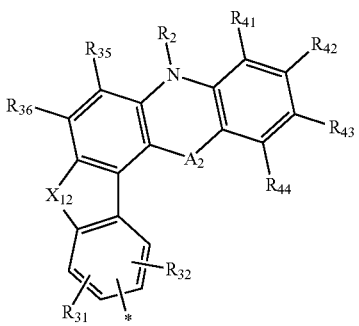
Formula 14-5
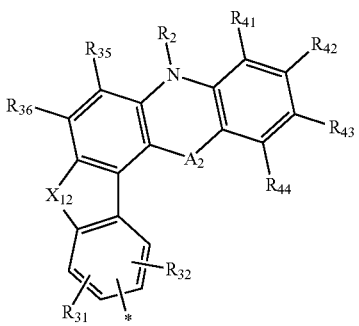
Formula 14-6
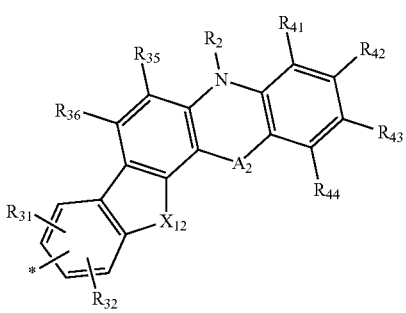
Formula 14-7
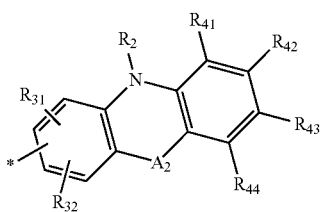
Formula 14-8
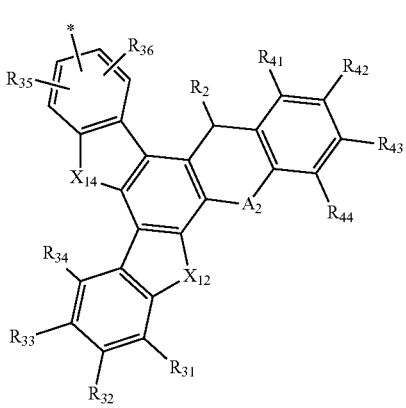
wherein, in Formulae 11-1 to 11-8, 12-1 to 12-8, 13-1 to 13-8, and 14-1 to 14-8,
$X_{11}$ and $X_{13}$ may be each independently $C(R_{17})(R_{18})$, $N(R_{19})$, O, or S, $X_{12}$ and $X_{14}$ may be each independently $C(R_{37})(R_{38})$, $N(R_{39})$, O, or S, $R_1$, $R_2$, $A_1$, and $A_2$ may be the same as those groups defined herein, $R_{11}$ to $R_{19}$ may be the same as described herein in connection with $R_{10}$, $R_{21}$ to $R_{24}$ may be the same as described herein in connection with $R_{20}$, $R_{31}$ to $R_{39}$ may be the same as described herein in connection with $R_{30}$, $R_{41}$ to $R_{44}$ may be the same as described herein in connection with $R_{40}$, and

* indicates a binding site to an adjacent atom.

In some embodiments, $A_1$ in Formulae 11, 12, 11-1 to 11-8, and 12-1 to 12-8 may be selected from a single bond, a $C_1$-$C_2$ alkylene group, and a $C_2$ alkenylene group; and a $C_1$-$C_2$ alkylene group and a $C_2$ alkenylene group, each substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, and —Si$(Q_{21})(Q_{22})(Q_{23})$, $A_2$ in Formulae 13, 14, 13-1 to 13-8, and 14-1 to 14-8 may be selected from a single bond, a $C_1$-$C_2$ alkylene group, and a $C_2$ alkenylene group; and a $C_1$-$C_2$ alkylene group and a $C_2$ alkenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —Si$(Q_{21})(Q_{22})(Q_{23})$, $R_2$, $R_{30}$ to $R_{39}$, and $R_{40}$ to $R_{44}$ in Formulae 13, 14, 13-1 to 13-8, and 14-1 to 14-8 may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, and a dibenzothiophenyl group;

a phenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group;

a phenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group; and —Si$(Q_1)(Q_2)(Q_3)$, wherein $Q_1$ to $Q_3$ and $Q_{21}$ to $Q_{23}$ may be each independently selected from hydrogen, a $C_1$-$C_{10}$ alkyl group, a $C_1$-$C_{10}$ alkoxy group, a phenyl group, and a naphthyl group, but embodiments are not limited thereto.

According to an embodiment, $Ar_1$ in Formula D-1 may be selected from groups represented by Formulae 15-1 to 15-17 and 16-1 to 16-8, $Ar_2$ in Formula D-1 may be selected from groups represented by Formulae 15-1 to 15-17 and 16-1 to 16-8, a phenyl group, and a naphthyl group, and $Ar_{11}$ and $Ar_{12}$ in Formula A-1 may be each independently selected from groups represented by Formulae 17-1 to 17-3, but embodiments are not limited thereto:

Formula 15-1

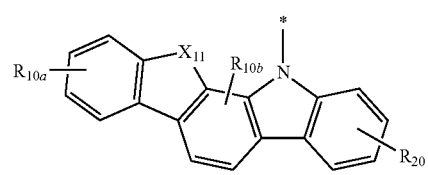

Formula 15-2

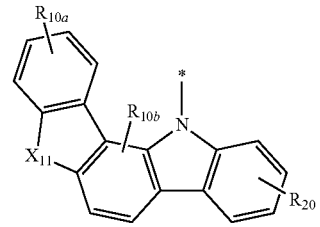

Formula 15-3

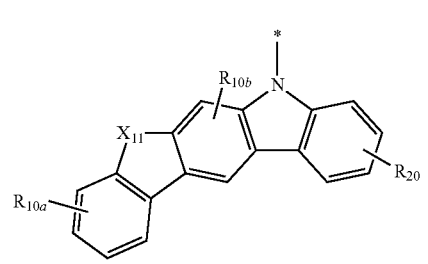

Formula 15-4

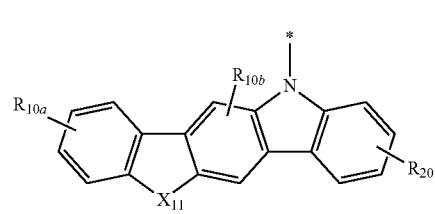

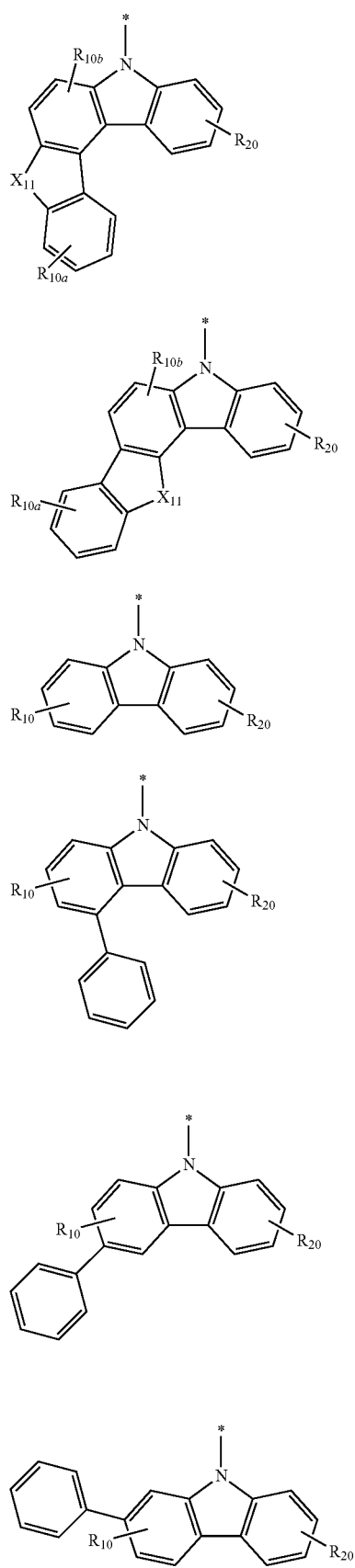
Formula 15-5
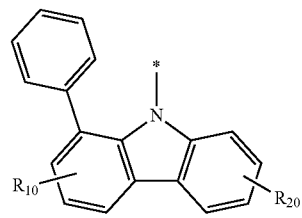
Formula 15-11
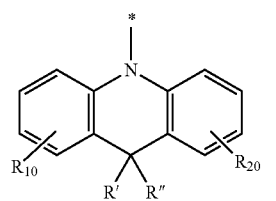
Formula 15-12
Formula 15-6
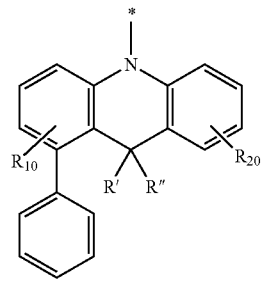
Formula 15-13
Formula 15-7
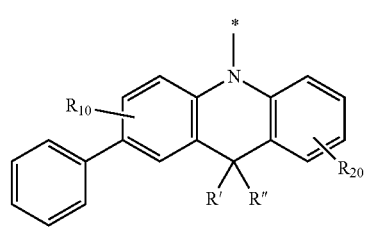
Formula 15-14
Formula 15-8
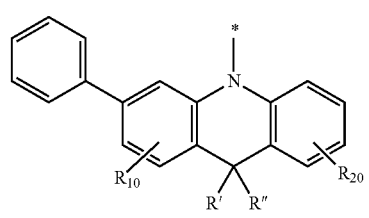
Formula 15-15
Formula 15-9
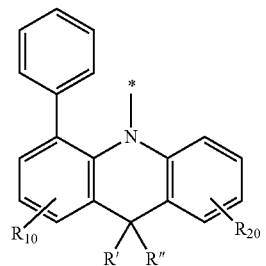
Formula 15-16
Formula 15-10

Formula 15-17
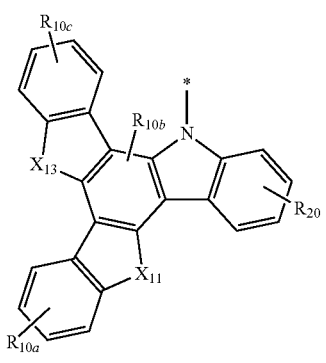

Formula 16-1
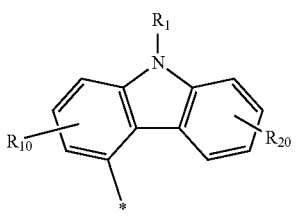

Formula 16-2
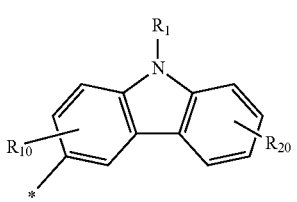

Formula 16-3
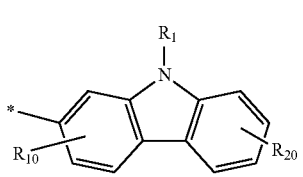

Formula 16-4
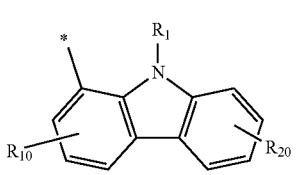

Formula 16-5
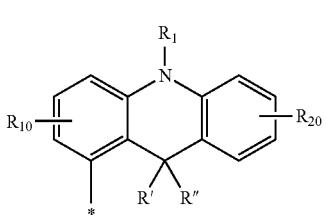

Formula 16-6
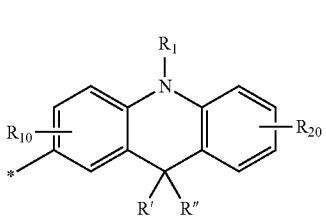

Formula 16-7
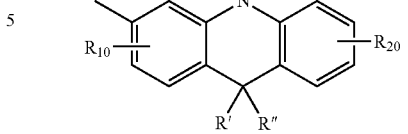

Formula 16-8
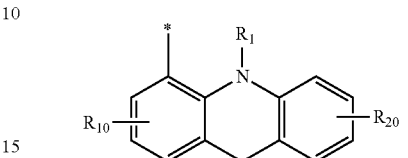

Formula 17-1
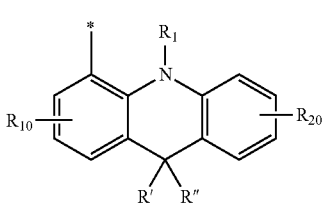

Formula 17-2
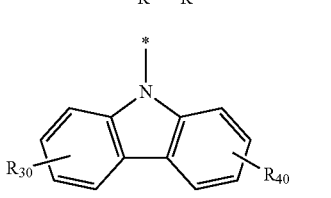

Formula 17-3
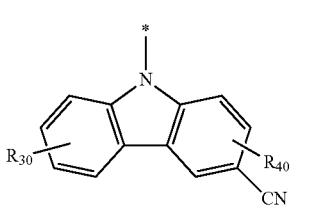

wherein, in Formulae 15-1 to 15-17, 16-1 to 16-8, and 17-1 to 17-3, $X_{11}$ and $X_{13}$ may be each independently $C(R_{17})(R_{18})$, $N(R_{19})$, O, or S, R' and R" may be each independently selected from hydrogen, deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, and a dibenzothiophenyl group, $R_1$, $R_{10}$, $R_{20}$, $R_{30}$, and $R_{40}$ may be the same as those described herein, and $R_{10a}$ to $R_{10c}$ may be the same as described herein in connection with $R_{10}$.

In some embodiments, in Formulae 15-1 to 15-17, 16-1 to 16-8, and 17-1 to 17-3, $R_1$, $R_{10}$, $R_{10a}$ to $R_{10c}$, and $R_{20}$ may be each independently selected from hydrogen, deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, and —Si($Q_1$)($Q_2$)($Q_3$), $R_{30}$ and $R_{40}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, and —$CFH_2$;

a phenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group;

a phenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, —$CFH_2$, a phenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group; and —$Si(Q_1)(Q_2)(Q_3)$, wherein $Q_1$ to $Q_3$ may be each independently selected from hydrogen, a $C_1$-$C_{10}$ alkyl group, a $C_1$-$C_{10}$ alkoxy group, a phenyl group, and a naphthyl group, but embodiments are not limited thereto.

In some embodiments, i) the donor compound may be represented by Formula D-1, provided that the donor compound may be selected from compounds in which $L_1$ in Formula D-1 is a single bond; or ii) the donor compound may be selected from compounds represented by Formulae D-1(1) to D-1(52):

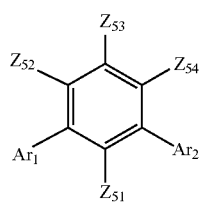

Formula D-1(1)

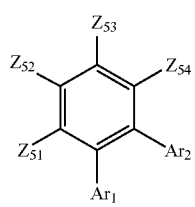

Formula D-1(2)

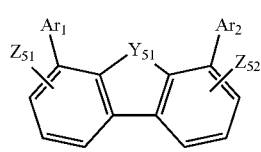

Formula D-1(3)

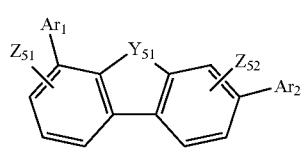

Formula D-1(4)

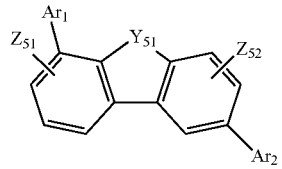

Formula D-1(5)

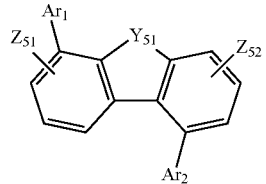

Formula D-1(6)

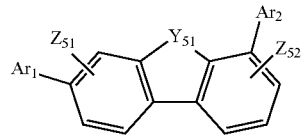

Formula D-1(7)

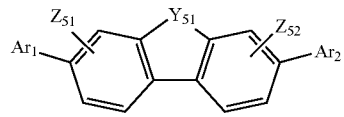

Formula D-1(8)

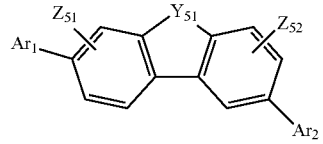

Formula D-1(9)

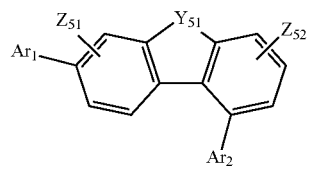

Formula D-1(10)

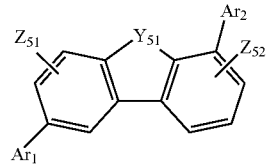

Formula D-1(11)

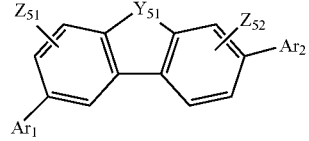

Formula D-1(12)

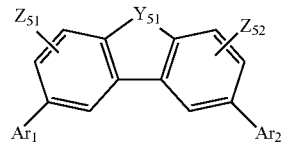

Formula D-1(13)

-continued
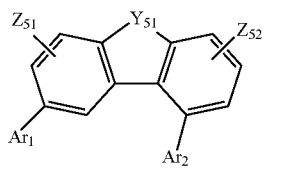
Formula D-1(14)
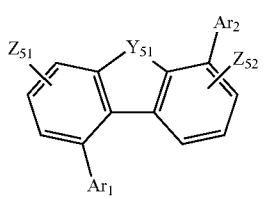
Formula D-1(15)
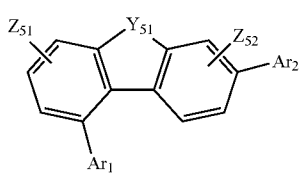
Formula D-1(16)
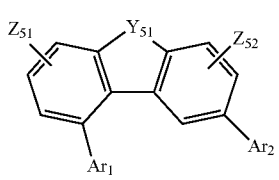
Formula D-1(17)
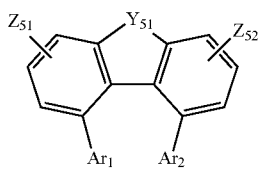
Formula D-1(18)
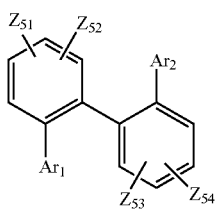
Formula D-1(19)
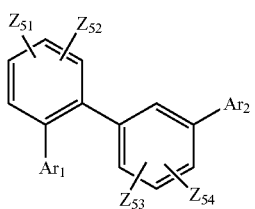
Formula D-1(20)
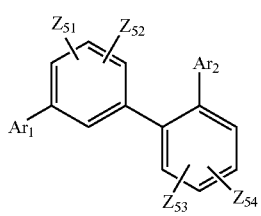
Formula D-1(21)
-continued
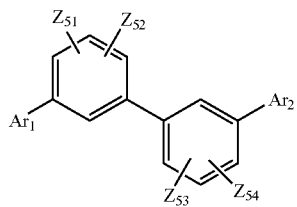
Formula D-1(22)
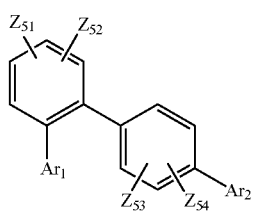
Formula D-1(23)
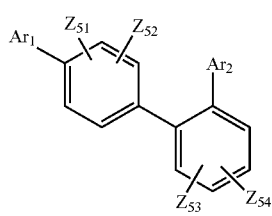
Formula D-1(24)
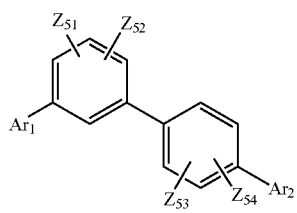
Formula D-1(25)
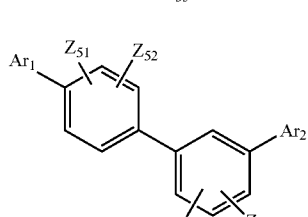
Formula D-1(26)
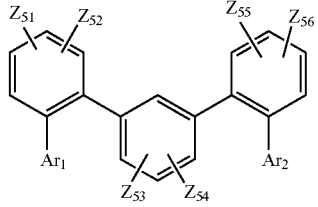
Formula D-1(27)
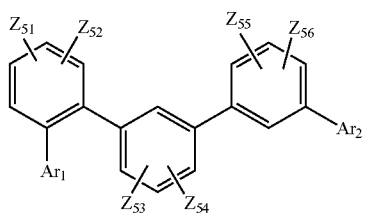
Formula D-1(28)

Formula D-1(29)
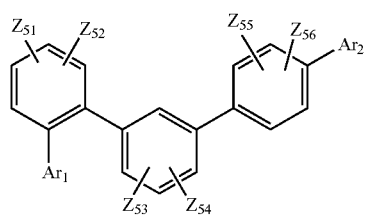
Formula D-1(30)
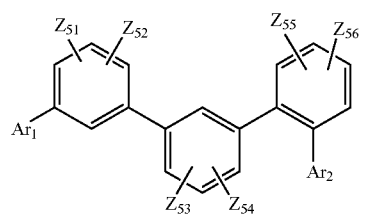
Formula D-1(31)
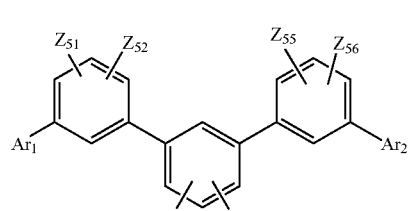
Formula D-1(32)
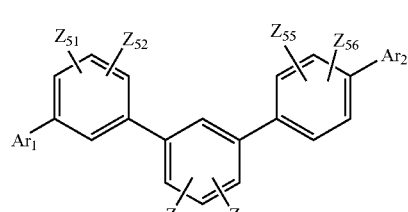
Formula D-1(33)
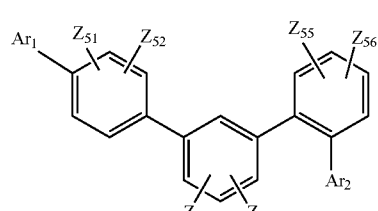
Formula D-1(34)
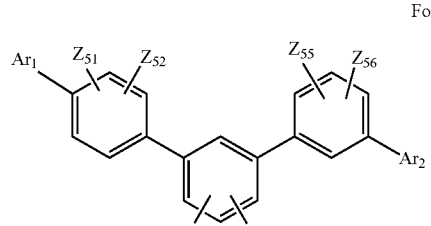
Formula D-1(35)
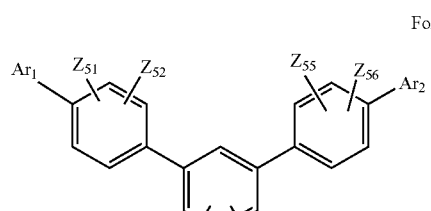
Formula D-1(36)
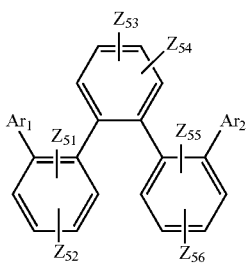
Formula D-1(37)
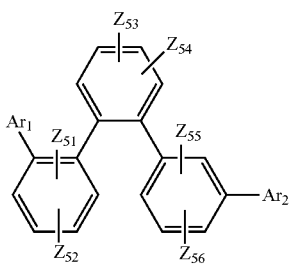
Formula D-1(38)
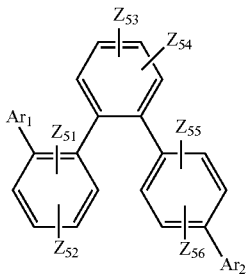
Formula D-1(39)
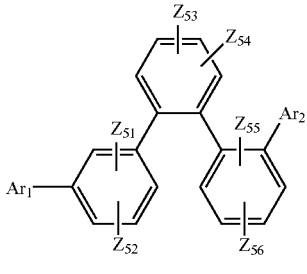
Formula D-1(40)
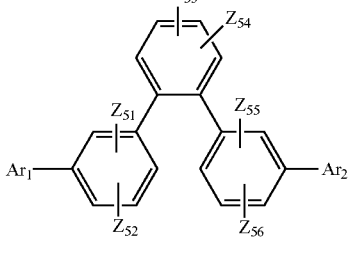
Formula D-1(41)
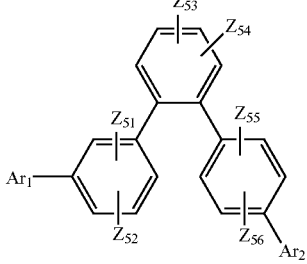

Formula D-1(42)
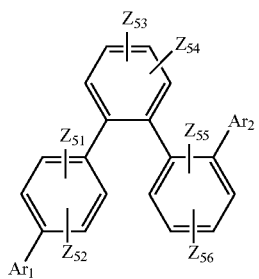
Formula D-1(43)
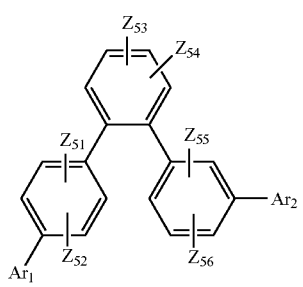
Formula D-1(44)
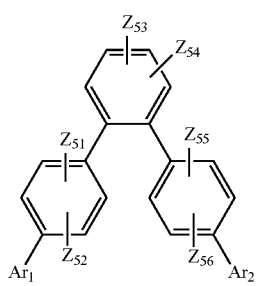
Formula D-1(45)
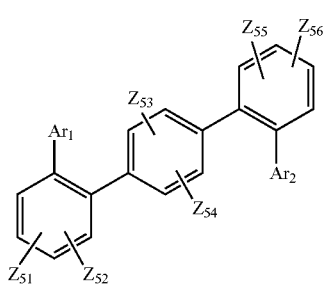
Formula D-1(46)
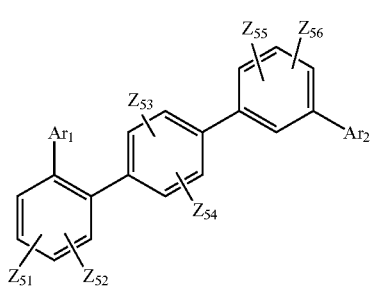
Formula D-1(47)
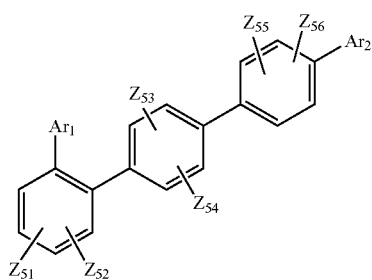
Formula D-1(48)
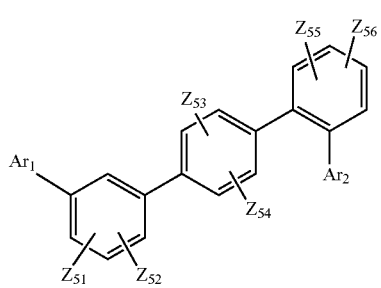
Formula D-1(49)
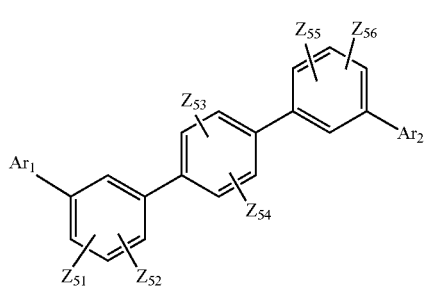
Formula D-1(50)
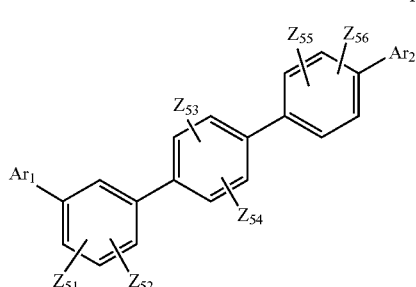
Formula D-1(51)
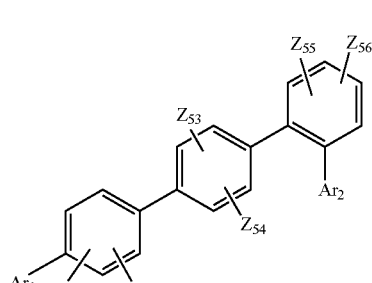

-continued

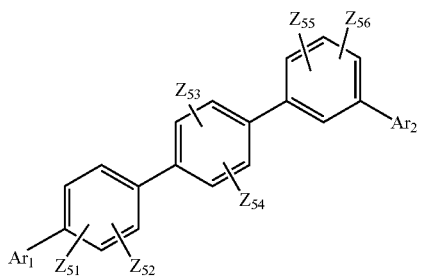

Formula D-(52)

wherein, in Formulae D-1(1) to D-1(52), $Ar_1$ and $Ar_2$ may be the same as those described herein, $Y_{51}$ may be each independently $C(Z_{53})(Z_{54})$, $N(Z_{55})$, O, or S, and $Z_{51}$ to $Z_{56}$ may be each independently selected from hydrogen, deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, and $-Si(Q_{11})(Q_{12})(Q_{13})$, wherein $Q_{11}$ to $Q_{13}$ may be each independently selected from hydrogen, a $C_1$-$C_{10}$ alkyl group, a $C_1$-$C_{10}$ alkoxy group, a phenyl group, and a naphthyl group.

In some embodiments, in Formulae D-1(1) to D-1(52), $Ar_1$ may be selected from groups represented by Formulae 11 and 12, and $Ar_2$ may be selected from groups represented by Formulae 11 and 12, a phenyl group, and a naphthyl group; and a phenyl group and a naphthyl group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, naphthyl group, a fluorenyl group, a carbazolyl group, a dibenzofuranyl group, and a dibenzothiophenyl group.

According to some embodiments, in Formulae D-1(1) to D-1(52), $Ar_1$ may be selected from groups represented by Formulae 11-1 to 11-8 and 12-1 to 12-8, and $Ar_2$ may be selected from groups represented by Formulae 11-1 to 11-8 and 12-1 to 12-8, a phenyl group, and a naphthyl group, but embodiments are not limited thereto.

$L_{11}$ to $L_{13}$ in Formulae A-1 and A-2 may be each independently selected from groups represented by Formulae 3-1 to 3-56, and i) at least one of $L_{11}$ in the number of a11, ii) at least one of $L_{12}$ in the number of a12, and iii) at least one of $L_{13}$ in the number of a13 may be each independently selected from groups represented by Formulae 3-15 to 3-56:

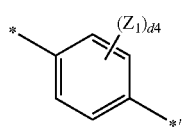

Formula 3-1

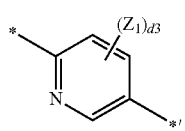

Formula 3-2

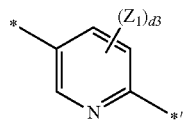

Formula 3-3

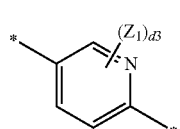

Formula 3-4

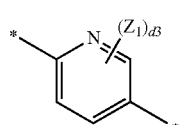

Formula 3-5

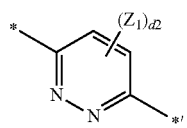

Formula 3-6

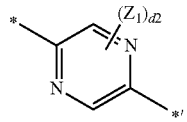

Formula 3-7

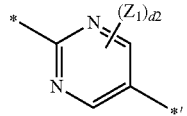

Formula 3-8

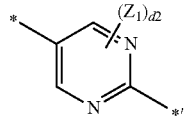

Formula 3-9

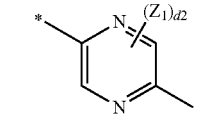

Formula 3-10

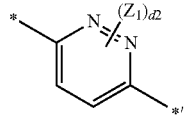

Formula 3-11

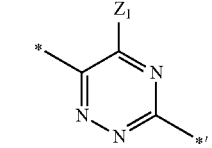

Formula 3-12

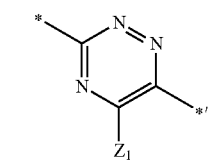

Formula 3-13

-continued
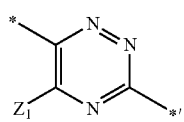
Formula 3-14
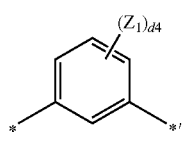
Formula 3-15
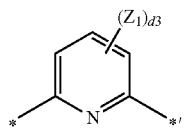
Formula 3-16
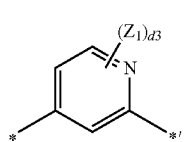
Formula 3-17
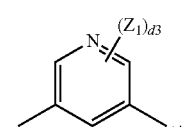
Formula 3-18
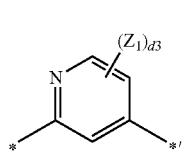
Formula 3-19
Formula 3-20
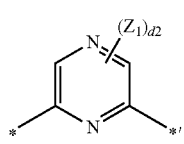
Formula 3-21
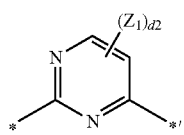
Formula 3-22
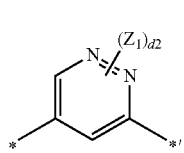
Formula 3-23
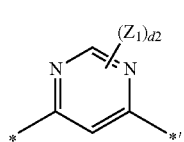
Formula 3-24
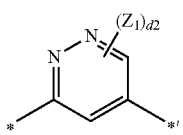
Formula 3-25
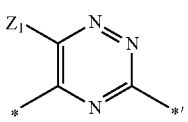
Formula 3-26
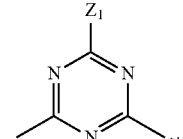
Formula 3-27
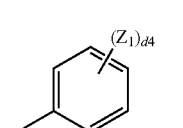
Formula 3-28
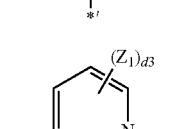
Formula 3-29
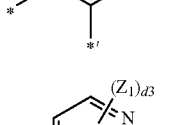
Formula 3-30
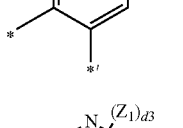
Formula 3-31
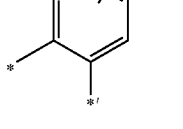
Formula 3-32
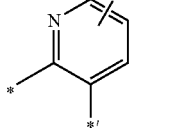
Formula 3-33
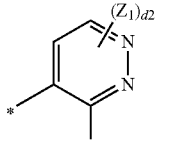
Formula 3-34
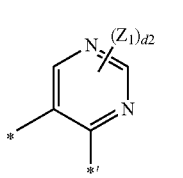

Formula 3-35
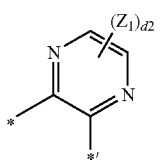
Formula 3-36
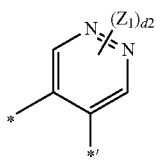
Formula 3-37
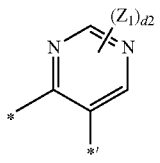
Formula 3-38
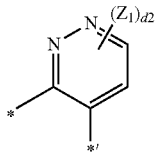
Formula 3-39
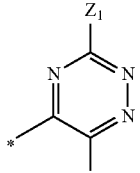
Formula 3-40
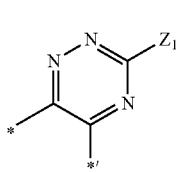
Formula 3-41
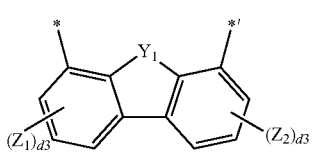
Formula 3-42
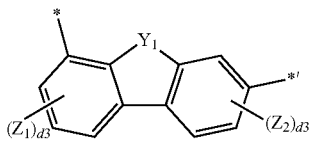
Formula 3-43
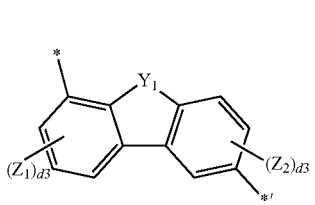
Formula 3-44
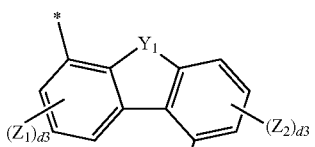
Formula 3-45
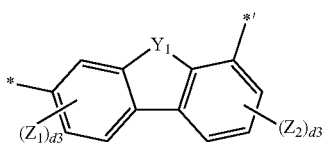
Formula 3-46
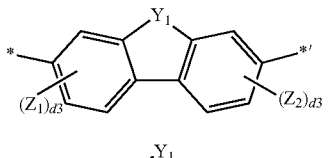
Formula 3-47
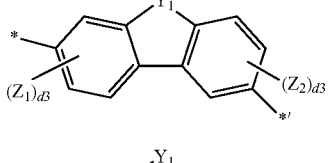
Formula 3-48
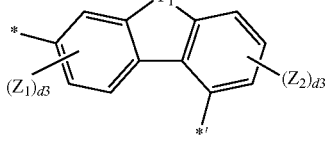
Formula 3-49
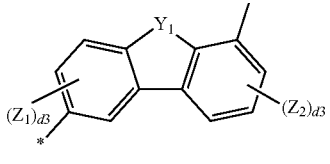
Formula 3-50
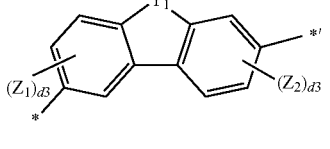
Formula 3-51
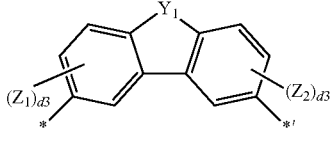
Formula 3-52
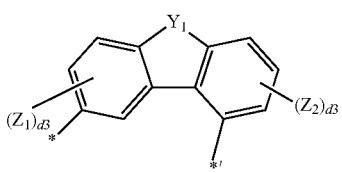
Formula 3-53

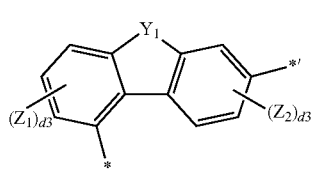

Formula 3-54

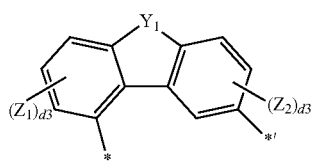

Formula 3-55

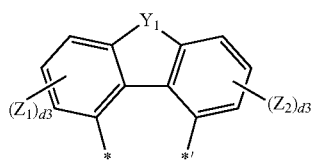

Formula 3-56 wherein, in Formulae 3-1 to 3-56, $Y_1$ may be selected from O, S, $C(Z_3)(Z_4)$, and $N(Z_5)$, $Z_1$ to $Z_5$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, —$CFH_2$, a phenyl group, a phenyl group substituted with a cyano group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —Si$(Q_{11})(Q_{12})(Q_{13})$, wherein $Q_{11}$ to $Q_{13}$ may be each independently selected from hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, and a dibenzothiophenyl group, d4 may be an integer selected from 0 to 4, d3 may be an integer selected from 0 to 3, d2 may be an integer selected from 0 to 2, and

* and *' each indicate a binding site to an adjacent atom.

According to some embodiments, groups represented by *-$(L_{11})_{a11}$-*', *-$(L_{12})_{a12}$-*', and *-$(L_{13})_{a13}$-*' in Formulae A-1 and A-2 may be selected from groups represented by Formulae 4-1 to 4-39:

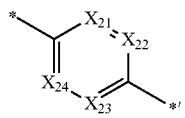

Formula 4-1

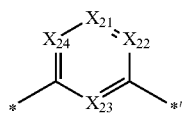

Formula 4-2

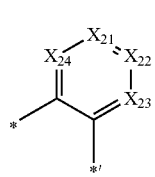

Formula 4-3

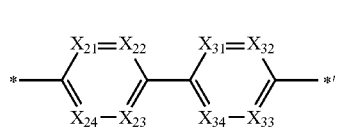

Formula 4-4

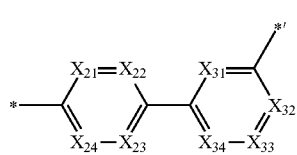

Formula 4-5

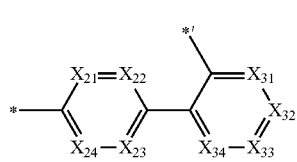

Formula 4-6

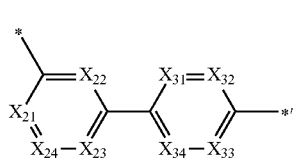

Formula 4-7

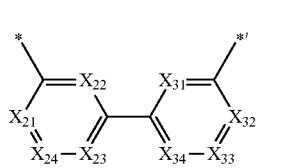

Formula 4-8

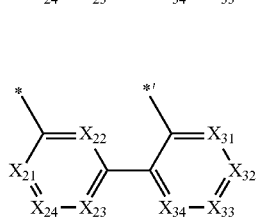

Formula 4-9

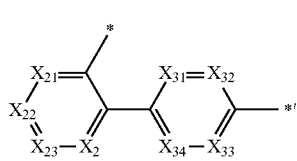

Formula 4-10

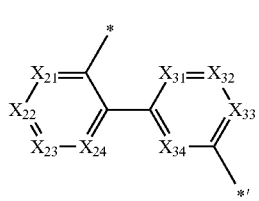

Formula 4-11

-continued

Formula 4-12

Formula 4-13

Formula 4-14

Formula 4-15

Formula 4-16

Formula 4-17

Formula 4-18

Formula 4-19

Formula 4-20

Formula 4-21

Formula 4-22

Formula 4-23

Formula 4-24

Formula 4-25

Formula 4-26
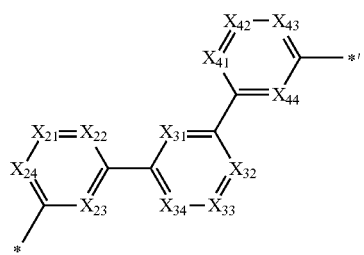
Formula 4-27
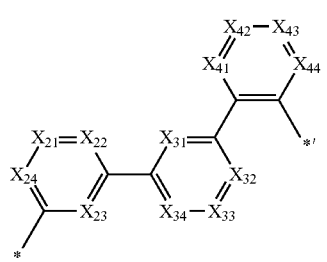
Formula 4-28
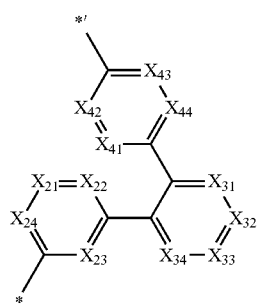
Formula 4-29
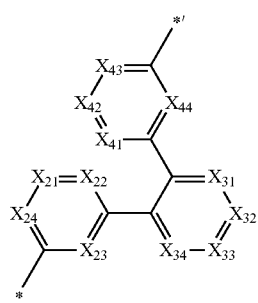
Formula 4-30
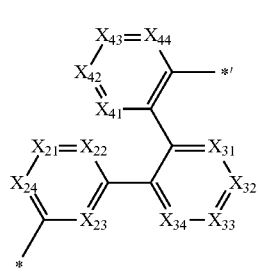
Formula 4-31
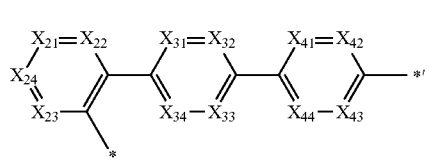
Formula 4-32
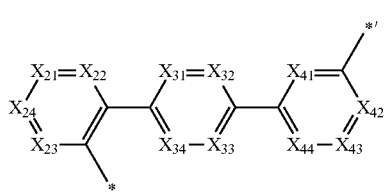
Formula 4-33
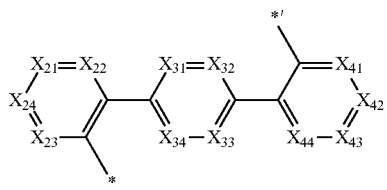
Formula 4-34
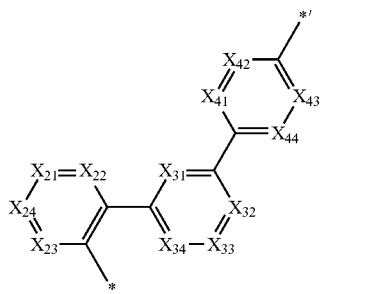
Formula 4-35
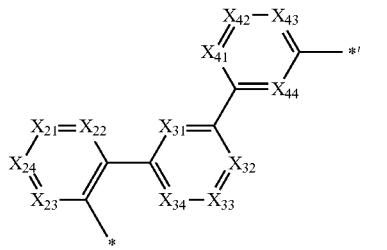
Formula 4-36
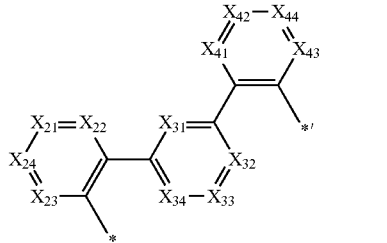
Formula 4-37
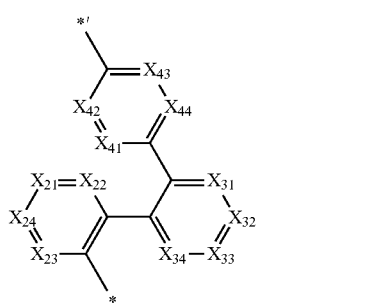

-continued

Formula 4-38

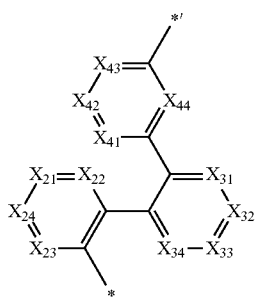

Formula 4-39

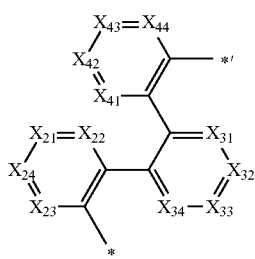

wherein, in Formulae 4-1 to 4-39, $X_{21}$ may be N or $C(Z_{21})$, $X_{22}$ may be N or $C(Z_{22})$, $X_{23}$ may be N or $C(Z_{23})$, $X_{24}$ may be N or $C(Z_{24})$, $X_{31}$ may be N or $C(Z_{31})$, $X_{32}$ may be N or $C(Z_{32})$, $X_{33}$ may be N or $C(Z_{33})$, $X_{34}$ may be N or $C(Z_{34})$, $X_{41}$ may be N or $C(Z_{41})$, $X_{42}$ may be N or $C(Z_{42})$, $X_{43}$ may be N or $C(Z_{43})$, and $X_{44}$ may be N or $C(Z_{44})$, provided that at least one of $X_{21}$ to $X_{24}$ may not be N, at least one of $X_{31}$ to $X_{34}$ may not be N, and at least one of $X_{41}$ to $X_{44}$ may not be N, $Z_{21}$ to $Z_{24}$, $Z_{31}$ to $Z_{34}$, and $Z_{41}$ to $Z_{44}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, —$CFH_2$, a phenyl group, a phenyl group substituted with a cyano group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —$Si(Q_{11})(Q_{12})(Q_{13})$, wherein $Q_{11}$ to $Q_{13}$ may be each independently selected from hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, and a dibenzothiophenyl group, and

* and *' each indicate a binding site to an adjacent atom.

$T_{11}$ to $T_{16}$ in Formula A-2 may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, and —$CFH_2$;

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$CF_3$, —$CF_2H$, and —$CFH_2$;

a phenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, and a dibenzothiophenyl group;

a phenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, —$CFH_2$, a phenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, and a dibenzothiophenyl group; and —$Si(Q_1)(Q_2)(Q_3)$, wherein $Q_1$ to $Q_3$ may be each independently selected from hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, and a dibenzothiophenyl group.

In some embodiments, $T_{11}$ to $T_{16}$ in Formula A-2 may be each independently selected from hydrogen, deuterium, —F, a cyano group, a $C_1$-$C_{10}$ alkyl group, a $C_1$-$C_{10}$ alkoxy group —$CF_3$, —$CF_2H$, and —$CFH_2$;

a $C_1$-$C_{10}$ alkyl group and a $C_1$-$C_{10}$ alkoxy group, each substituted with at least one selected from deuterium, —F, a cyano group —$CF_3$, —$CF_2H$, and —$CFH_2$;

a phenyl group, a pyridinyl group, a pyrimidinyl group, a triazinyl group, a carbazolyl group, a dibenzofuranyl group, and a dibenzothiophenyl group;

a phenyl group, a pyridinyl group, a pyrimidinyl group, a triazinyl group, a carbazolyl group, a dibenzofuranyl group, and a dibenzothiophenyl group, each substituted with at least one selected from deuterium, —F, a cyano group, a $C_1$-$C_{10}$ alkyl group, a $C_1$-$C_{10}$ alkoxy group, —$CF_3$, —$CF_2H$, —$CFH_2$, a phenyl group, a pyridinyl group, a pyrimidinyl group, a triazinyl group, a carbazolyl group, a dibenzofuranyl group, and a dibenzothiophenyl group; and —$Si(Q_1)(Q_2)(Q_3)$, wherein $Q_1$ to $Q_3$ may be each independently selected from hydrogen, a $C_1$-$C_{10}$ alkyl group, a $C_1$-$C_{10}$ alkoxy group, a phenyl group, a pyridinyl group, a pyrimidinyl group, a triazinyl group, a carbazolyl group, a dibenzofuranyl group, and a dibenzothiophenyl group.

In some embodiments, i) the acceptor compound may be represented by Formula A-1, provided that the acceptor compound may be selected from compounds in which $Ar_{11}$ and $Ar_{12}$ in Formula A-1 may be each independently selected from groups represented by Formulae 17-1 to 17-3, and at least one of $Ar_{11}$ and $Ar_{12}$ may be selected from groups represented by Formulae 17-2 and 17-3;

ii) the acceptor compound may be represented by Formula A-1, provided that the acceptor compound may be selected from compounds in which $L_{11}$ in Formula A-1 may be selected from groups represented by Formulae 3-15 and 3-28, and at least one of $L_{11}$ in number of a11 may be selected from groups represented by Formulae 6-1 to 6-4; or iii) the acceptor compound may be represented by Formula A-2, provided that the acceptor compound may be selected from compounds in which $X_1$ to $X_3$ in Formula A-2 may all be N, but embodiments are not limited thereto.

According to some embodiments, the donor compound may be selected from Compounds D1 to D16, and the acceptor compound may be selected from Compounds A1 to A11, but embodiments are not limited thereto:

D1

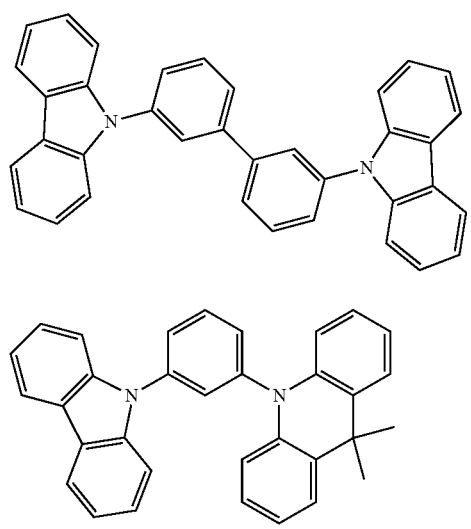

D2

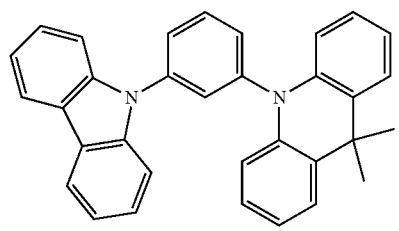

D3

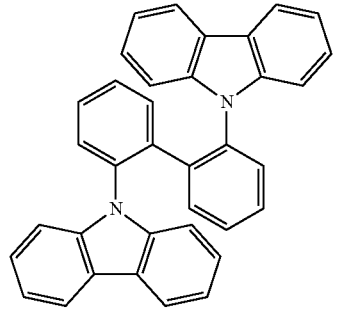

D4

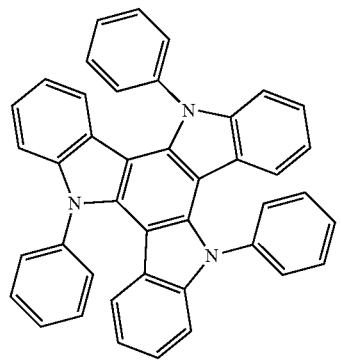

-continued

D5

D6

D7

D8

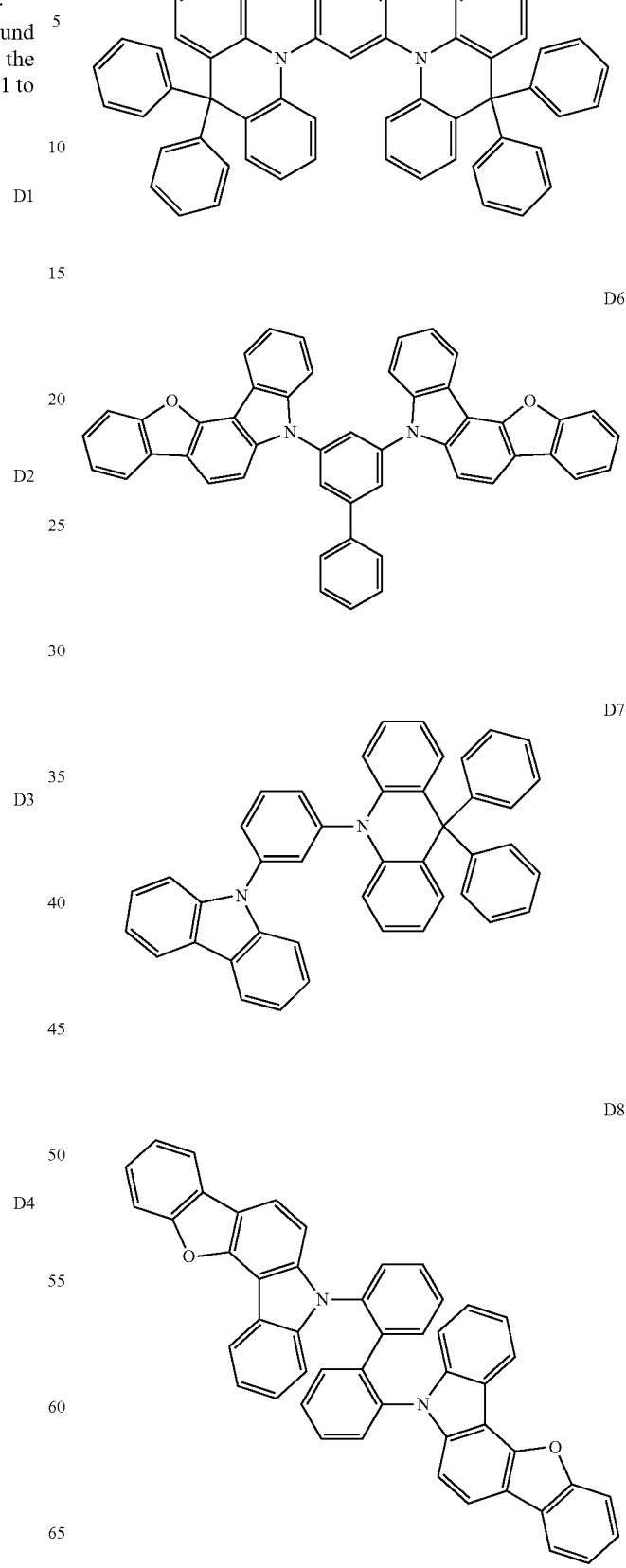

D9 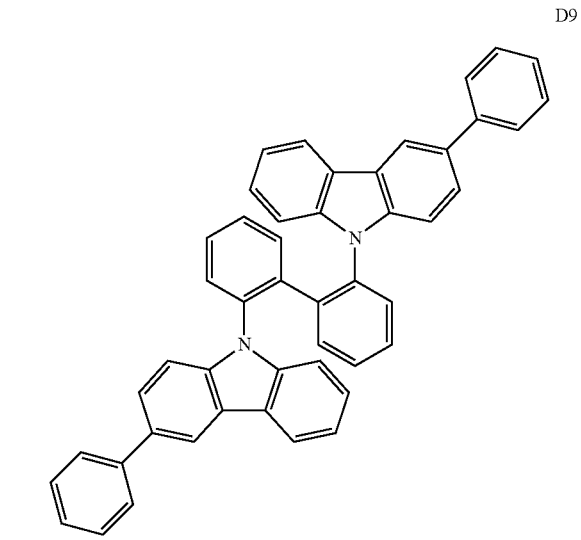
D10 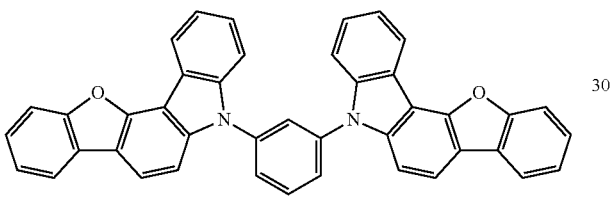
D11 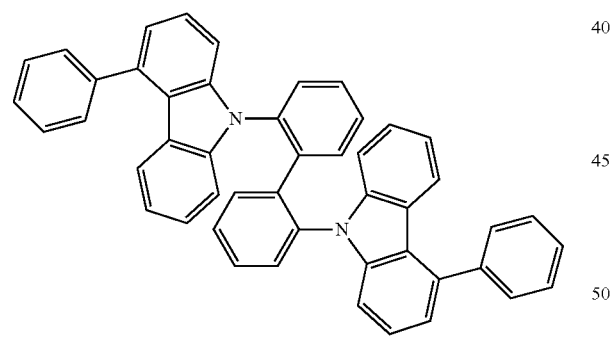
D12 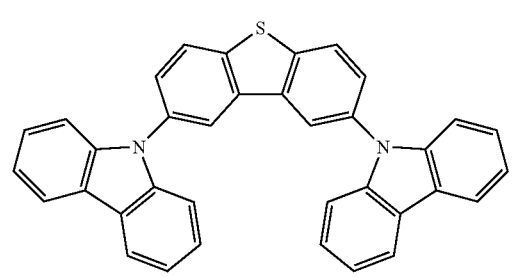
D13 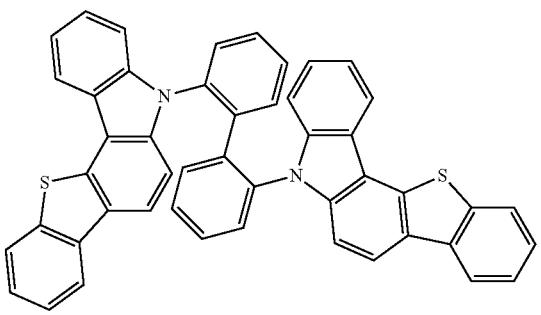
D14 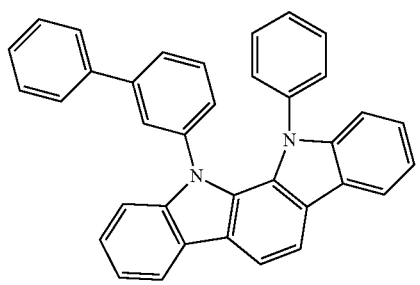
D15 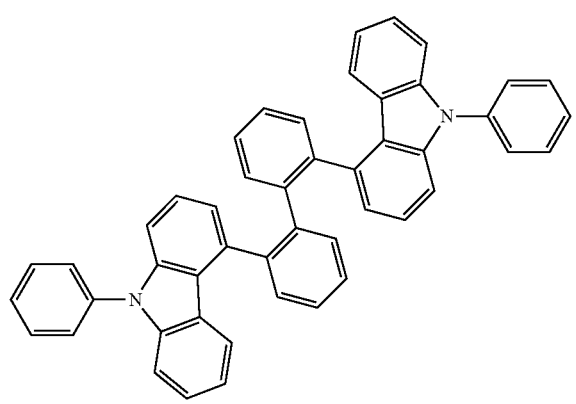
D16

A1
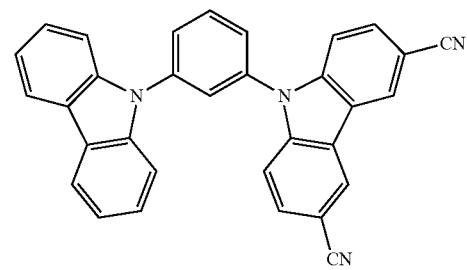
A2
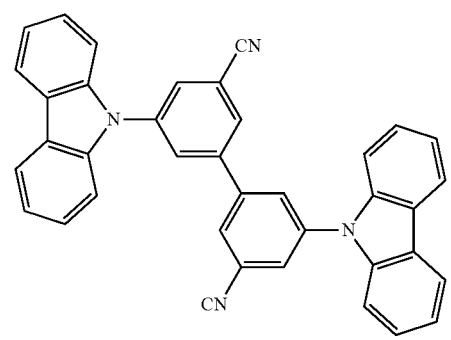
A3
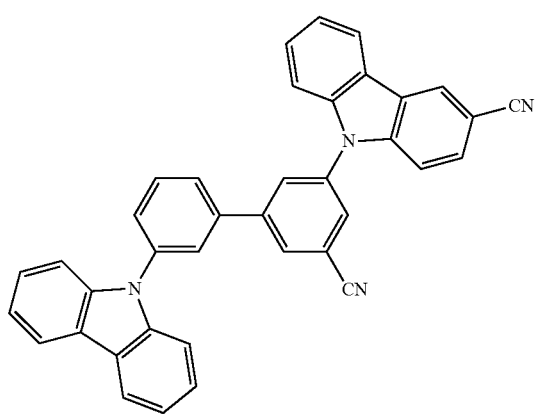
A4
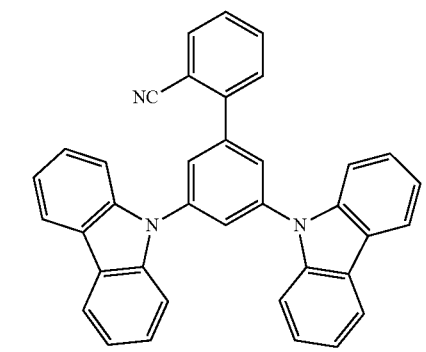
A5
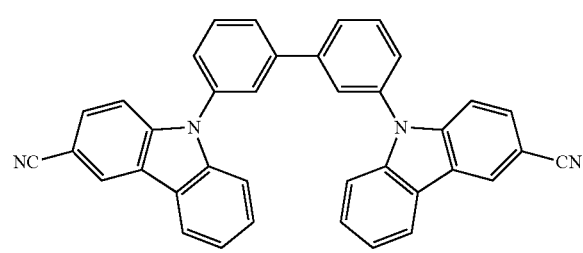
A6
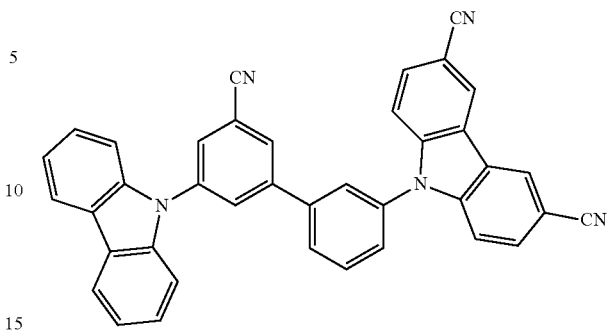
A7
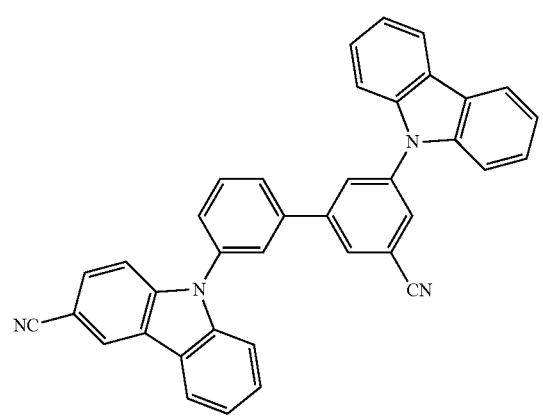
A8
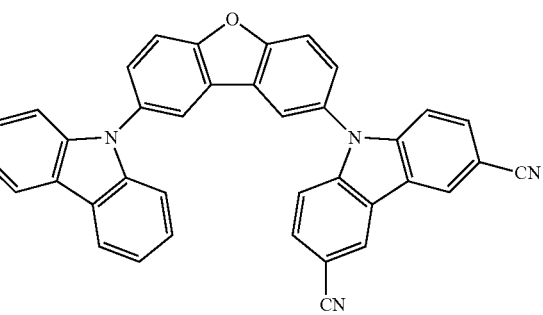
A9
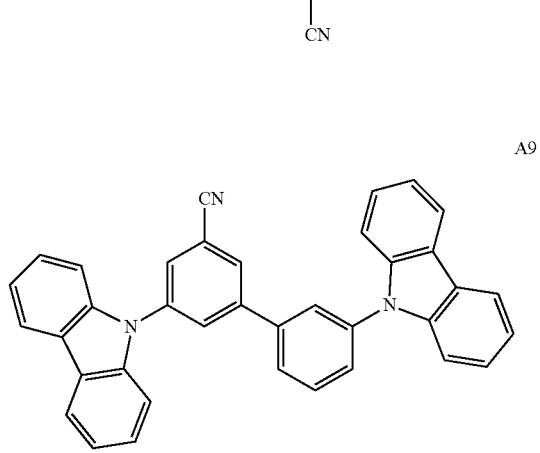

A10

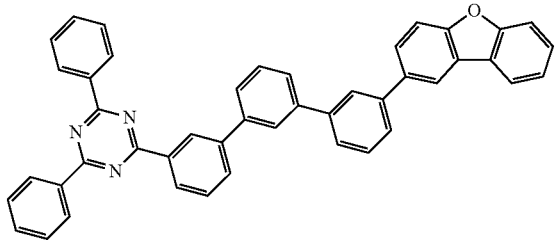

A11

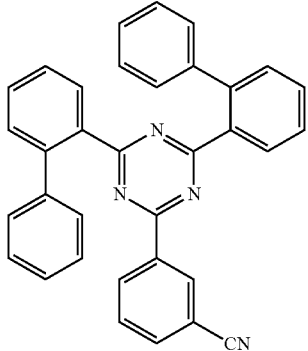

The composition may be used to form a thin film. Thus, a thin film including the composition may be provided. In some embodiments, the thin film may include the composition. In some embodiments, the thin film may include the composition and a fluorescent dopant or the composition and a phosphorescent dopant. In some embodiments, the thin film may include the composition and a fluorescent dopant or the composition and a phosphorescent dopant, but embodiments are not limited thereto.

The composition may be used in an emission layer of an electronic device, e.g., an organic light-emitting device. Thus, according to another aspect, there is provided an organic light-emitting device that includes:
 a first electrode;
 a second electrode; and
 an organic layer that is between the first electrode and the second electrode,
wherein the organic layer may include a thin film including the composition.

The organic light-emitting device may include the thin film including the composition, thus having a low driving voltage, high efficiency, and long lifespan. The thin film including the composition in the organic light-emitting device may be, for example, an emission layer.

Thus, according to an embodiment, the organic light-emitting device may include an emission layer including the composition.

The exciplex in the composition included in the emission layer may have $T_{decay}(Ex)$ of about 100 ns or greater (e.g., about 150 ns or greater), and thus, the exciplex may be, for example, a thermally activated delayed fluorescence emitter (TADF).

According to an embodiment, the emission layer may include the composition.

In some embodiments, in an organic light-emitting device of which the emission layer includes the composition, light emitted from the emission layer may be blue light, wherein a maximum emission wavelength of the blue light may be in a range of about 390 nm to about 490 nm, X coordinates in CIE color-coordinates of the blue light may be in a range of about 0.182 to about 0.307, and Y coordinates in CIE color-coordinates of the blue light may be in a range of about 0.092 to about 0.523. That is, the organic light-emitting device may emit blue light with high color purity.

In various embodiments, the emission layer may further include a fluorescent dopant as well as the composition. In this case, in the emission layer, the amount of the composition may be greater than that of the fluorescent dopant.

In some embodiments, a maximum emission wavelength ($\lambda_{max}$(Ex)) in a PL spectrum of the exciplex may be less than a maximum emission wavelength ($\lambda_{max}$(FD)) in a PL spectrum of the fluorescent dopant. Accordingly, the energy may be transferred from the composition to the fluorescent dopant, and thus, an emission mechanism in the emission layer may mostly depend on energy transfer from an excited state to a ground state of the fluorescent dopant. In other words, the composition in the emission layer may serve as a so-called assistant-dopant in delayed fluorescence, and thus, the emission color of the fluorescent dopant may determine the emission color of the emission layer. In some embodiments, when the fluorescent dopant is a green dopant, the emission layer may emit green light.

The PL spectrum of the exciplex may be a spectrum measured at room temperature with respect to a film that is formed by co-deposition of the donor compound and the acceptor compound on a substrate, and the PL spectrum of the fluorescent dopant may be a spectrum measured at room temperature with respect to a film that is formed by deposition of the fluorescent dopant on a substrate.

FIG. 1 is a schematic view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19, which are sequentially stacked in this stated order.

A substrate may be additionally disposed under the first electrode 11 or above the second electrode 19. Any substrate that is used in general organic light-emitting devices may be used as the substrate, and the substrate may be a glass substrate or a transparent plastic substrate, each having excellent mechanical strength, thermal stability, transparency, surface smoothness, ease of handling, and water-resistance.

The first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode 11 may be, for example, indium tin oxide (ITO), indium zinc oxide (IZO), tin oxide ($SnO_2$), and zinc oxide (ZnO). In various embodiments, magnesium (Mg), aluminum (Al), aluminum-lithium (Al—Li), calcium (Ca), magnesium-indium (Mg—In), or magnesium-silver (Mg—Ag) may be used as the material for forming the first electrode 11.

The first electrode 11 may have a single-layered structure or a multi-layered structure including two or more layers. For example, the first electrode 11 may have a three-layered structure of ITO/Ag/ITO, but the structure of the first electrode 11 is not limited thereto.

The organic layer 15 may be disposed on the first electrode 11.

The organic layer 15 may include a hole transport region, an emission layer, and an electron transport region.

The hole transport region may be between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In various embodiments, the hole transport region may have a structure of hole injection layer/hole transport layer or hole injection layer/hole transport layer/electron blocking layer, which are sequentially stacked in this stated order from the first electrode 11.

A hole injection layer may be formed on the first electrode 11 by using one or more suitable methods selected from vacuum deposition, spin coating, casting, or Langmuir-Blodgett (LB) deposition.

When a hole injection layer is formed by vacuum deposition, the deposition conditions may vary depending on a material that is used to form the hole injection layer and the structure and thermal characteristics of the hole injection layer. In some embodiments, the deposition conditions may include a deposition temperature of about 100° C. to about 500° C., a vacuum pressure of about $10^{-8}$ torr to about $10^{-3}$ torr, and a deposition rate of about 0.01 Angstroms per second (Å/sec) to about 100 Å/sec. However, the deposition conditions are not limited thereto.

When the hole injection layer is formed using spin coating, coating conditions may vary depending on the material used to form the hole injection layer and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (Pani/PSS), a compound represented by Formula 201 below, and a compound represented by Formula 202 below:

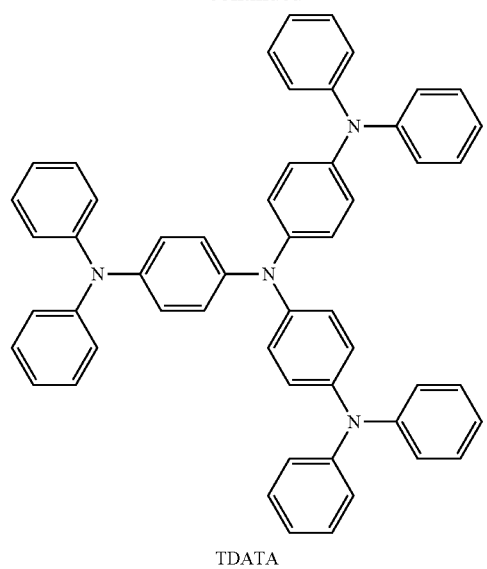

TDATA

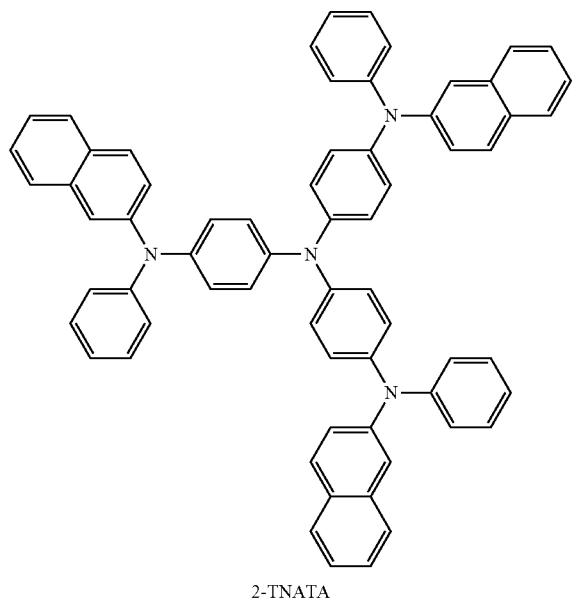

2-TNATA

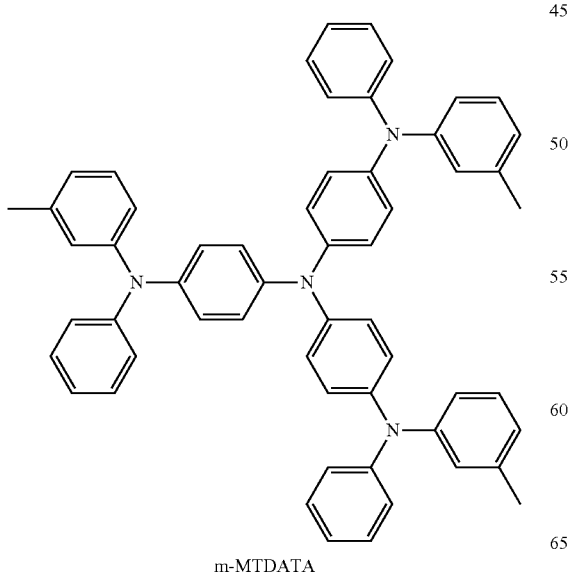

m-MTDATA

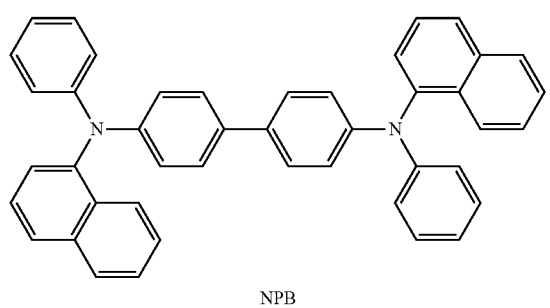

NPB

-continued

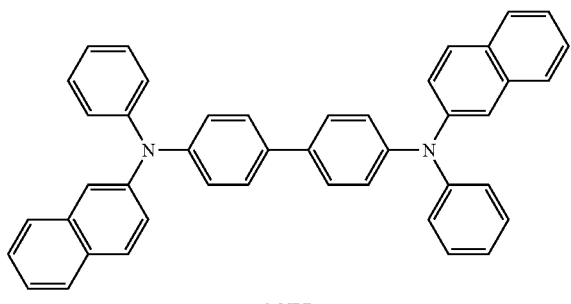

β-NPB

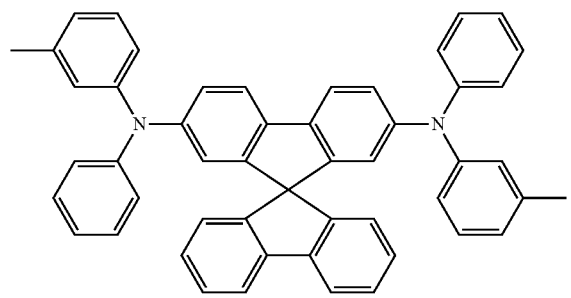

TPD

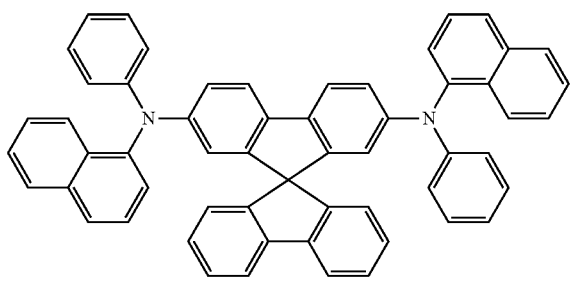

Spiro-TPD

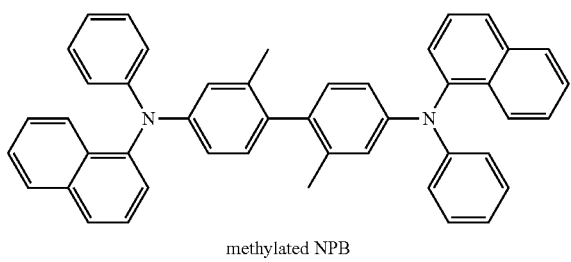

Spiro-NPB methylated NPB

-continued

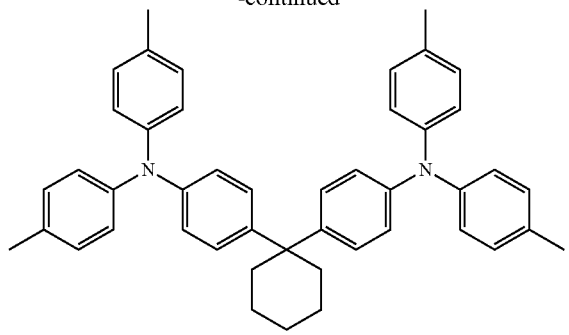

TAPC

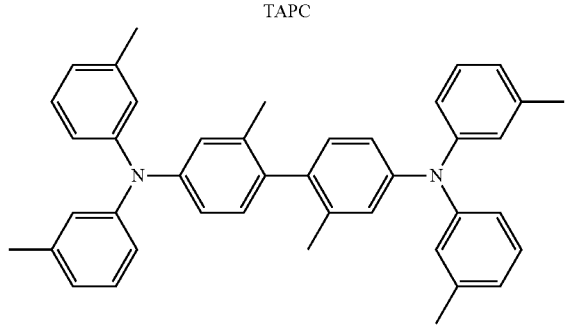

HMTPD

Formula 201

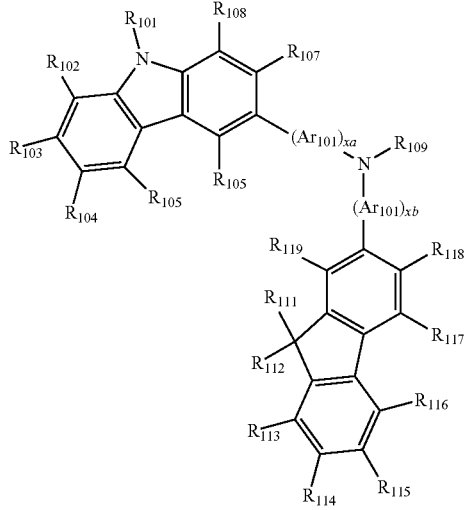

Formula 202

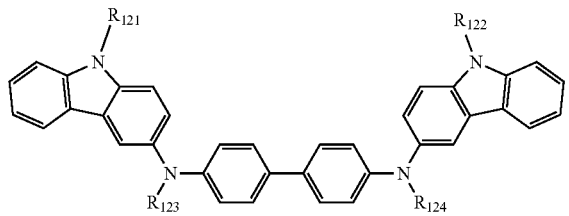

wherein, $Ar_{101}$ and $Ar_{102}$ in Formula 201 may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group.

xa and xb in Formula 201 may be each independently an integer selected from 0 to 5. Alternatively, xa and xb may be each independently an integer selected from 0, 1, and 2. In some embodiments, xa may be 1 and xb may be 0, but embodiments are not limited thereto.

$R_{101}$ to $R_{108}$, $R_{111}$ to $R_{119}$, and $R_{121}$ to $R_{124}$ in Formulae 201 and 202 may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (e.g., a methyl group, an ethyl group, a propyl group, a butyl group, pentyl group, or a hexyl group), and a $C_1$-$C_{10}$ alkoxy group (e.g., a methoxy group, an ethoxy group, a propoxy group, a butoxy group, or a pentoxy group);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments are not limited thereto.

$R_{109}$ in Formula 201 may be selected from a phenyl group, a naphthyl group, an anthracenyl group, and a pyridinyl group; and a phenyl group, a naphthyl group, an anthracenyl group and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In some embodiments, the compound represented by Formula 201 may be represented by Formula 201A, but embodiments are not limited thereto:

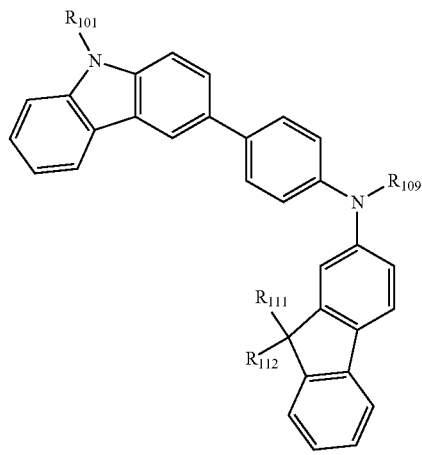

Formula 201A wherein $R_{101}$, $R_{111}$, $R_{112}$, and $R_{109}$ in Formula 201A may be the same as those described herein.

In some embodiments, the compound represented by Formula 201 and the compound represented by Formula 202 may include Compounds HT1 to HT20, but embodiments are not limited thereto:

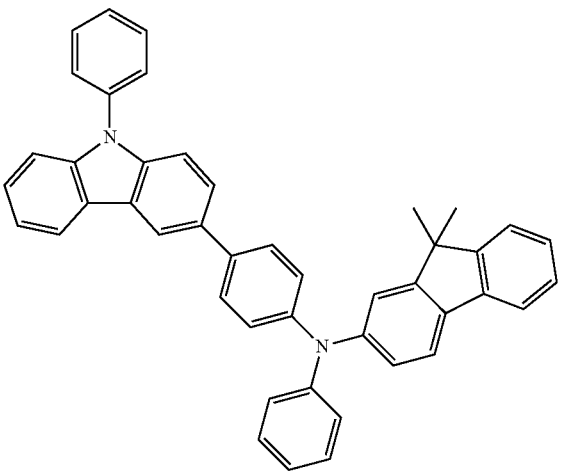

HT1

HT2
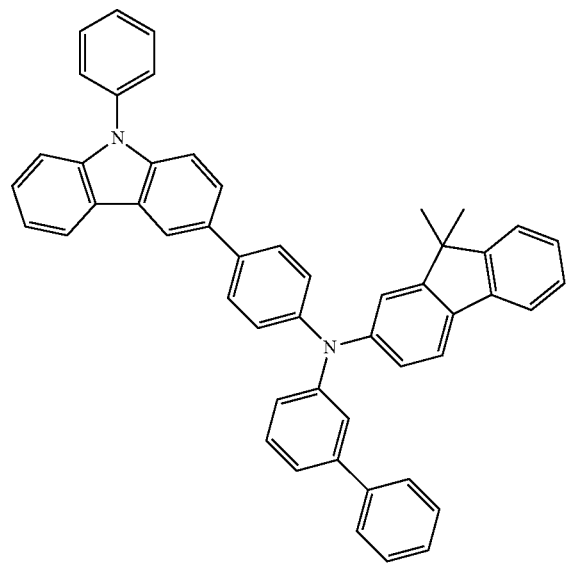
HT4
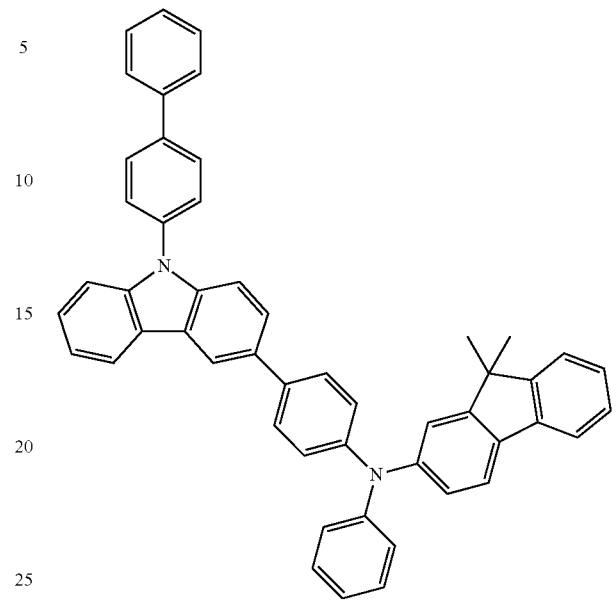
HT3
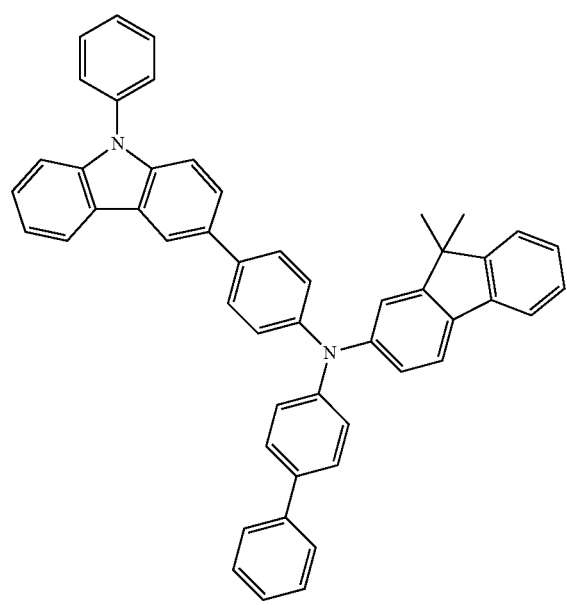
HT5
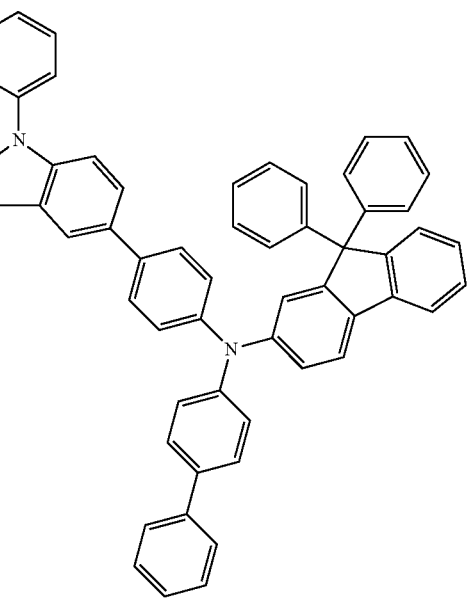

HT6
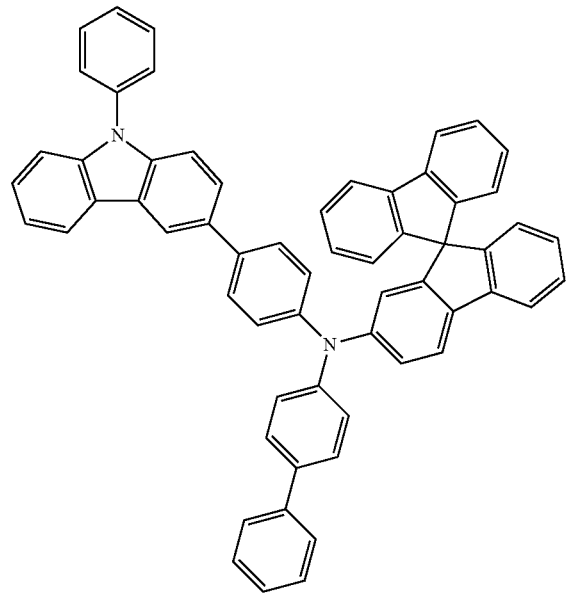
HT8
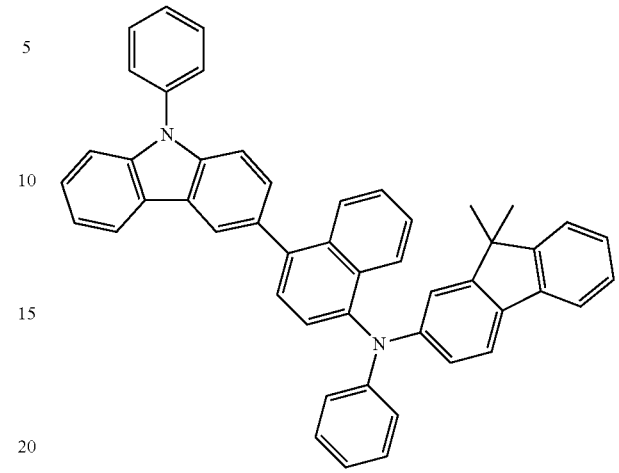
HT9
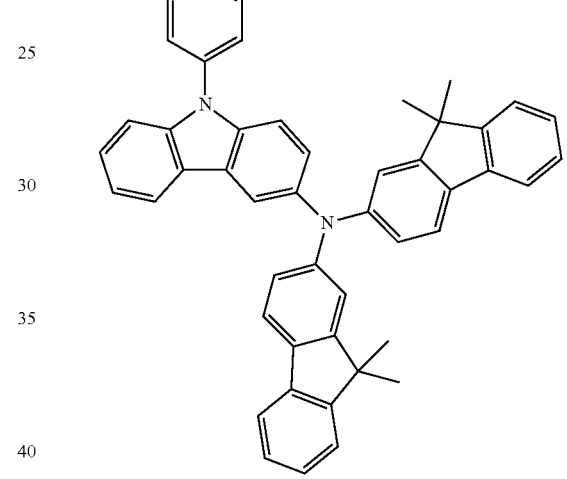
HT7
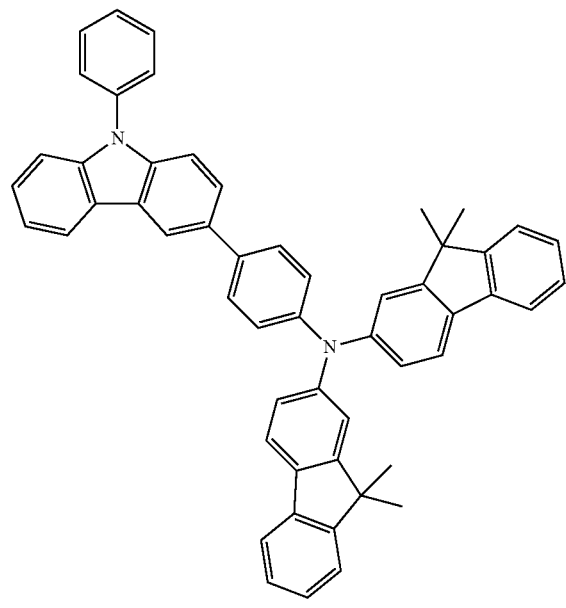
HT10
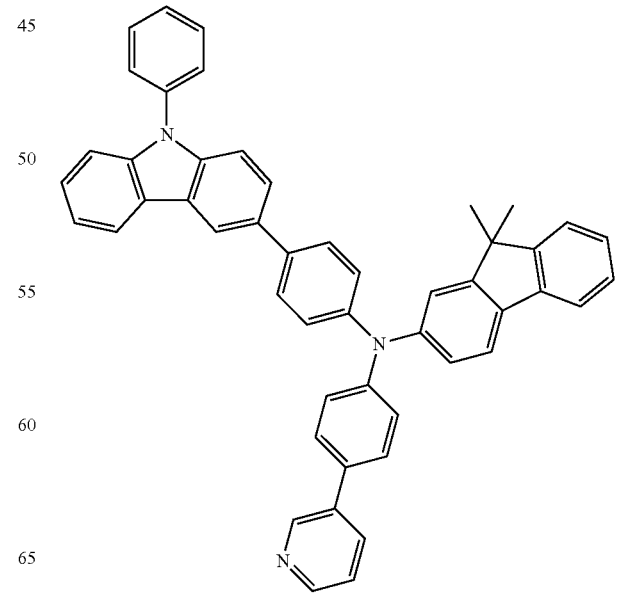

HT11
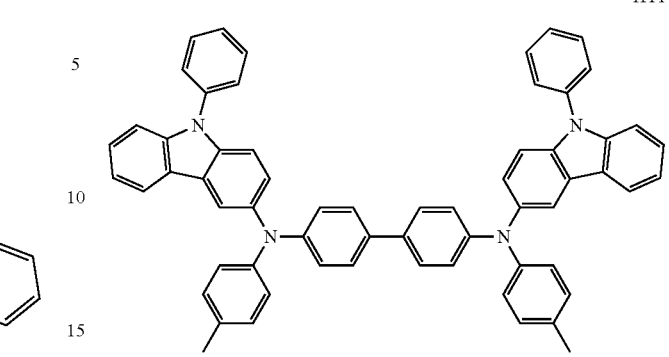
HT14
HT12
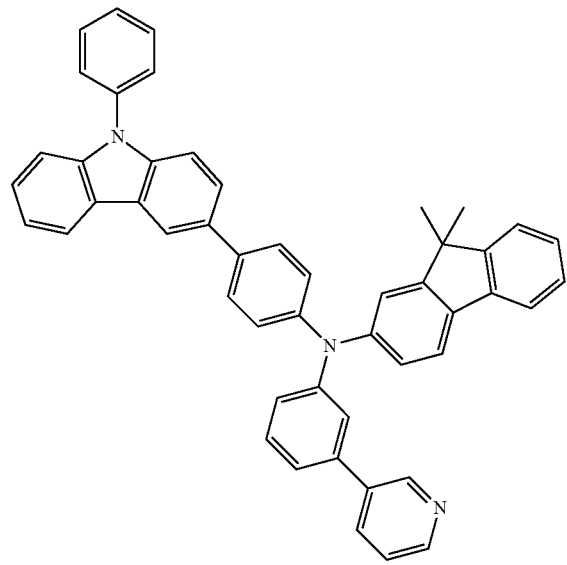
HT15
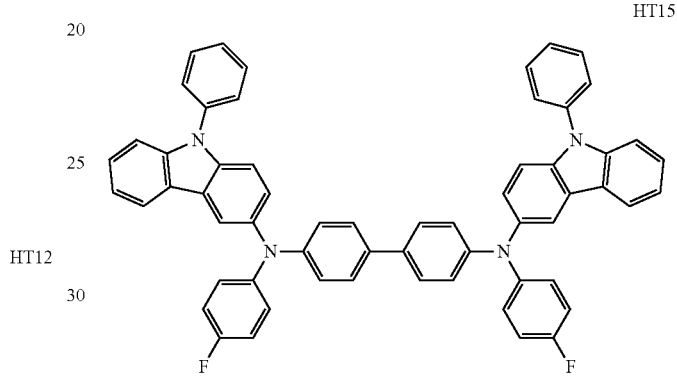
HT16
HT13
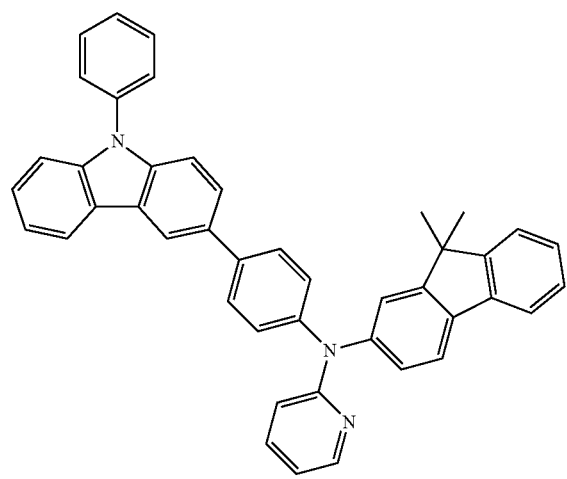
HT17
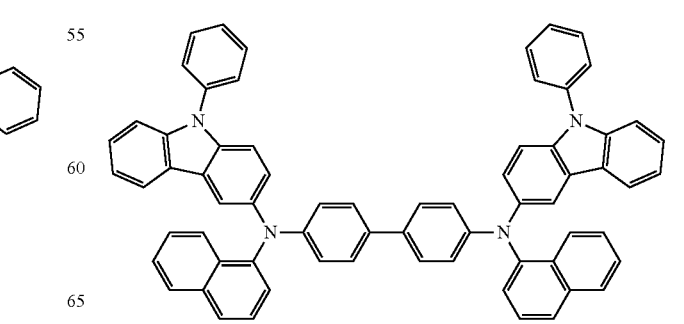

-continued

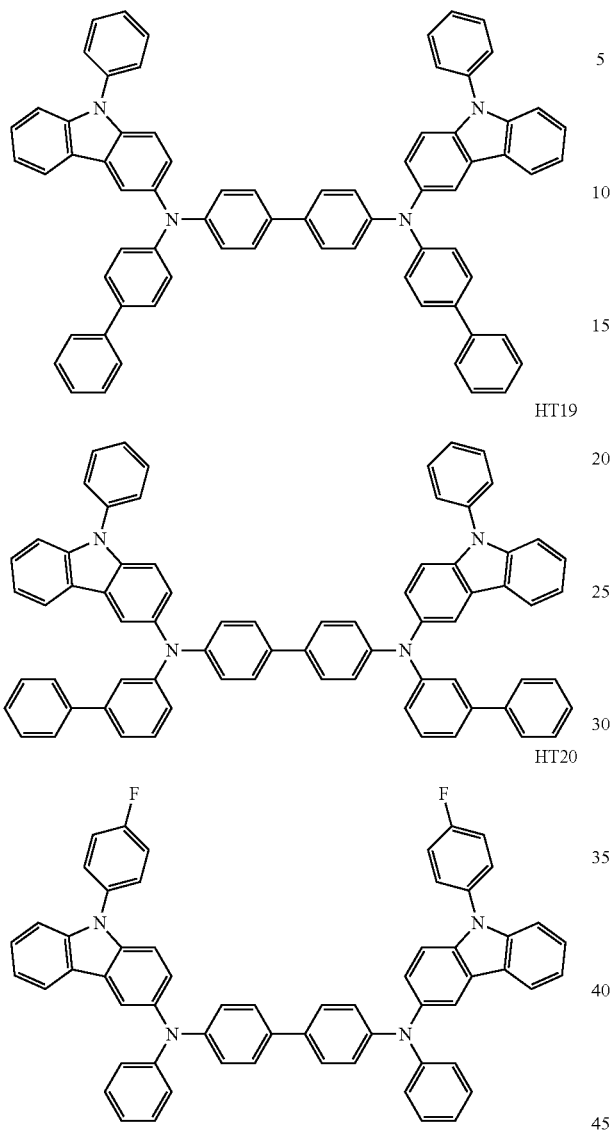

HT18

HT19

HT20

The thickness of the hole transport region may be in a range of about 100 Angstroms (Å) to about 10,000 Å, and in some embodiments, about 100 Å to about 1,000 Å. When the hole transport region includes at least one of a hole injection layer and a hole transport layer, the thickness of the hole injection layer may be in a range of about 100 Å to about 10,000 Å, and in some embodiments, about 100 Å to about 1,000 Å, and the thickness of the hole transport layer may be in a range of about 50 Å to about 2,000 Å, and in some embodiments, about 100 Å to about 1,500 Å. While not wishing to be bound by theory, it is understood that when the thicknesses of the hole transport region, the hole injection layer, and the hole transport layer are within these ranges, excellent hole transport characteristics may be obtained without a substantial increase in driving voltage.

The hole transport region may include a charge-generating material as well as the mentioned materials above, to improve conductive properties. The charge-generating material may be homogeneously or non-homogeneously dispersed throughout the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 or HP-1, but are not limited thereto:

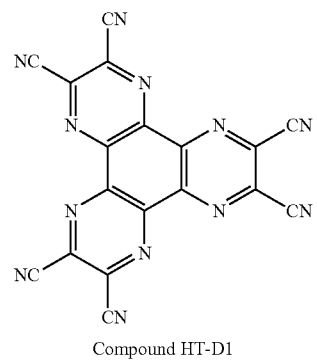

Compound HT-D1

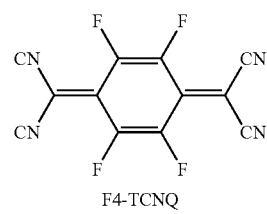

F4-TCNQ

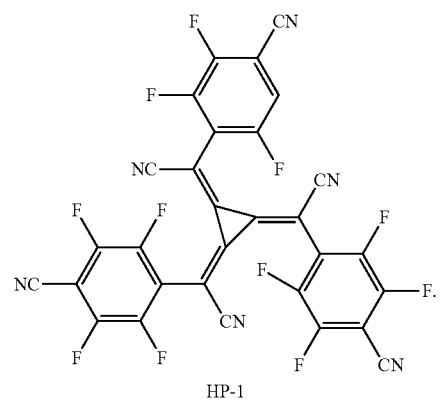

HP-1

The hole transport region may include a buffer layer.

Also, the buffer layer may compensate for an optical resonance distance according to a wavelength of light emitted from the emission layer, and thus, efficiency of a formed organic light-emitting device may be improved.

The hole transport region may further include an electron blocking layer. The electron blocking layer may include, for example, mCP, but a material therefor is not limited thereto:

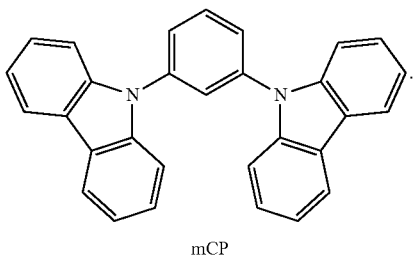 [SMILES: c1cc(-n2c3ccccc3c3ccccc32)cc(-n2c3ccccc3c3ccccc32)c1]

mCP

An emission layer may be formed on the hole transport region by using one or more suitable methods, such as vacuum deposition, spin coating, casting, or LB deposition. When the emission layer is formed by vacuum deposition or spin coating, vacuum deposition and coating conditions for the emission layer may be generally similar to the conditions for forming a hole injection layer, though the conditions may vary depending on the compound used.

When the organic light-emitting device 10 is a full color organic light-emitting device, the emission layer may be patterned into a red emission layer, a green emission layer, and a blue emission layer. In some embodiments, the emission layer may have a structure in which the red emission layer, the green emission layer, and/or the blue emission layer are layered to emit white light or other various embodiments are possible.

The emission layer may include the above-described composition.

According to an embodiment, the emission layer may include the composition.

In various embodiments, the emission layer may include the composition and a fluorescent dopant.

The fluorescent dopant may be any suitable fluorescent dopant known in the art.

In some embodiments, the fluorescent dopant may be selected from compounds represented by Formula 501:

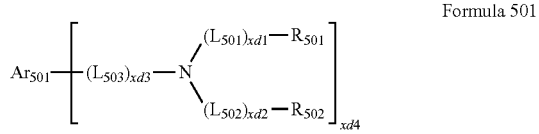

Formula 501 wherein, in Formula 501, $Ar_{501}$ may be selected from a naphthalene group, a heptalene group, a fluorene group, a spiro-bifluorene group, a carbazole group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group; and a naphthalene group, a heptalene group, a fluorene group, a spiro-bifluorene group, a carbazole group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, and —Si($Q_{501}$)($Q_{502}$)($Q_{503}$), wherein $Q_{501}$ to $Q_{503}$ may be each independently selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group, $L_{501}$ to $L_{503}$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $R_{501}$ and $R_{502}$ may be each independently selected from a phenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, xd1 to xd3 may be each independently selected from 0, 1, 2, and 3, and xd4 may be selected from 0, 1, 2, 3, 4, 5, and 6.

In some embodiments, in Formula 501, $Ar_{501}$ may be selected from a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group and an indenoanthracene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group and an indenoanthracene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group, $L_{501}$ to $L_{503}$ may be each independently selected from a phenylene group, a naphthylene group, a fluorenylene group, a spiro-bifluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-bifluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group, $R_{501}$ to $R_{502}$ may be each independently selected from a phenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xd1 to xd3 may be each independently 0, 1, or 2, and xd4 may be 0, 1, 2, 3, or 4, but embodiments are not limited thereto.

According to an embodiment, the fluorescent dopant may include at least one compound selected from compounds FD(1) to FD(5) and FD1 to FD8, but embodiments are not limited thereto:

Compound FD(1)

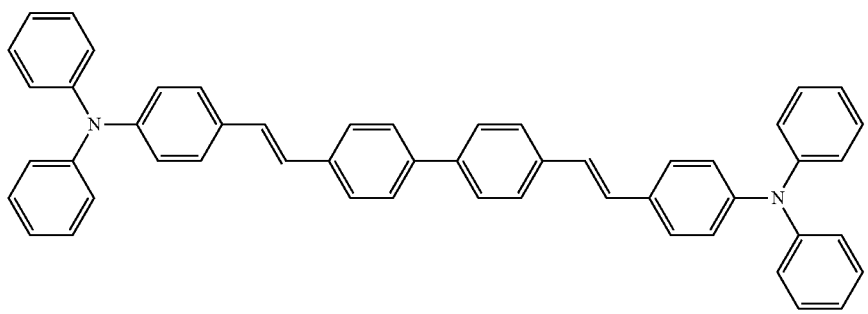

-continued
Compound FD(2)
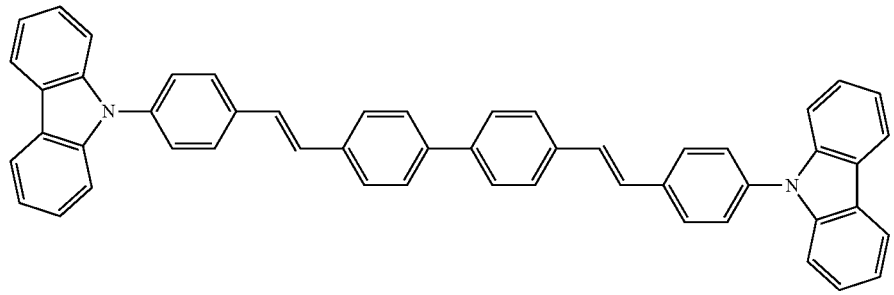
Compound FD(3)
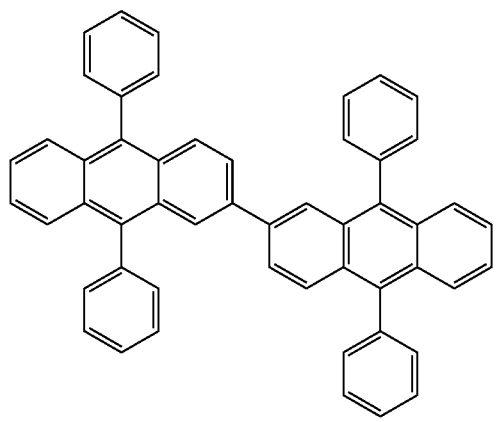
Compound FD(4)
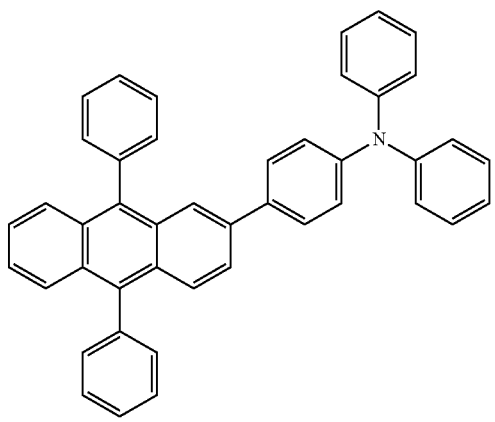
Compound FD(5)
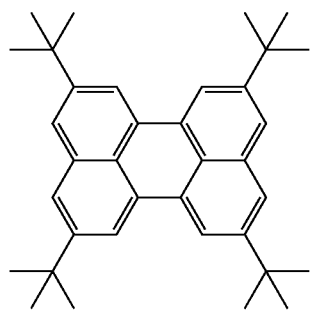
FD1
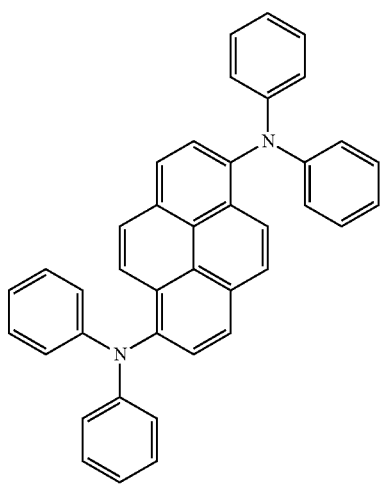

-continued
FD2
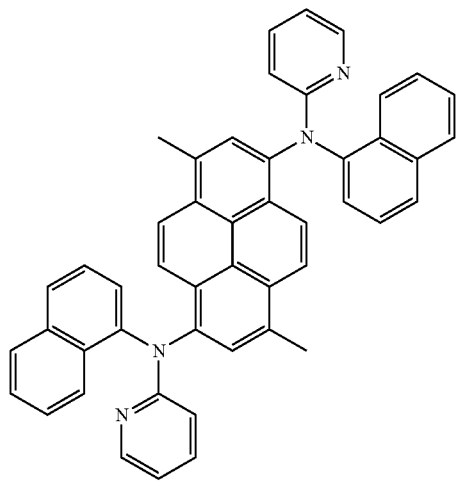
FD3
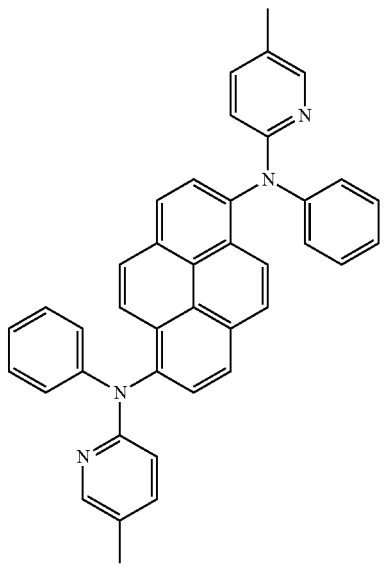
FD4
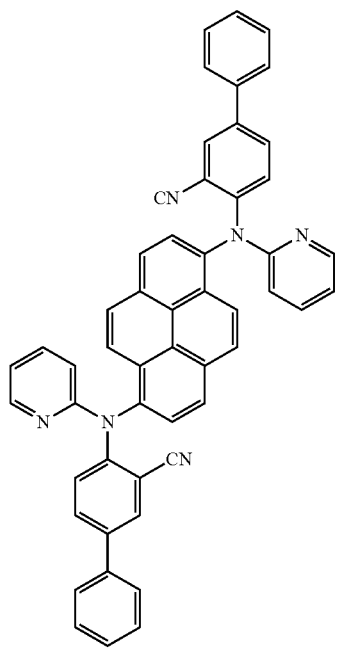
FD5
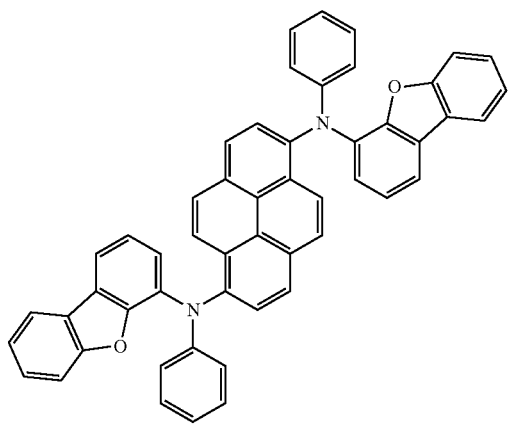
FD6
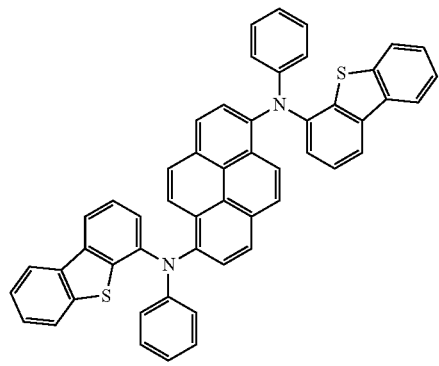
FD7
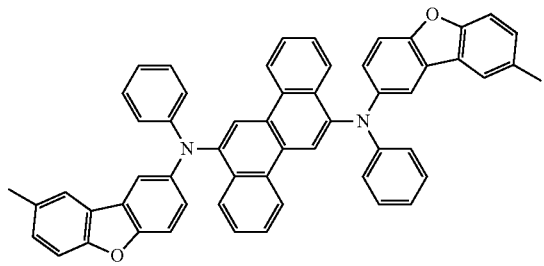

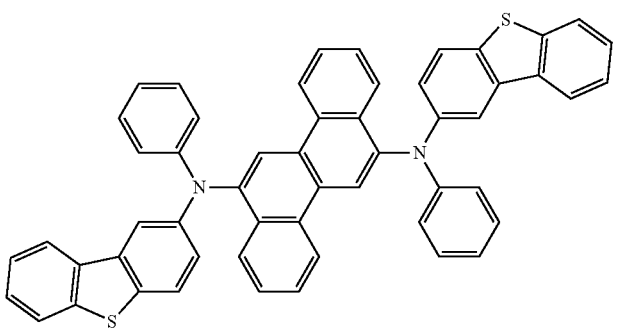

FD8

When the emission layer includes the composition and the fluorescent dopant, the amount of the fluorescent dopant may be selected from a range of about 0.01 parts by weight to about 20 parts by weight based on about 100 parts by weight of the composition, but embodiments are not limited thereto.

The thickness of the emission layer may be in a range of about 100 Å to about 1,000 Å, and in some embodiments, about 200 Å to about 600 Å. While not wishing to be bound by theory, it is understood that when the thickness of the emission layer is within these ranges, excellent light-emission characteristics may be achieved without a substantial increase in driving voltage.

An electron transport region may be next formed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP and Bphen, but may also include other materials:

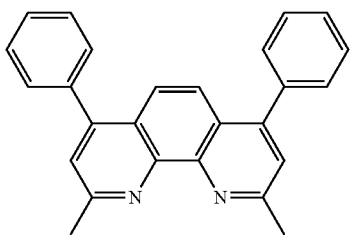

BCP

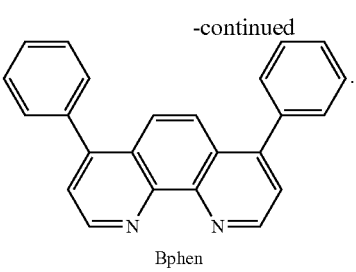

Bphen

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have improved hole blocking ability without a substantial increase in driving voltage.

The electron transport layer may further include at least one selected from BCP, BPhen, Alq3, BAlq, TAZ, and NTAZ:

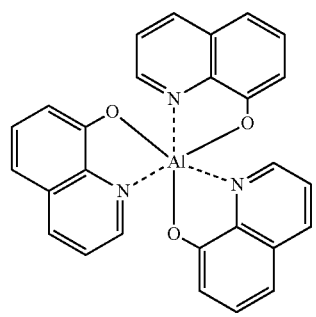

Alq3

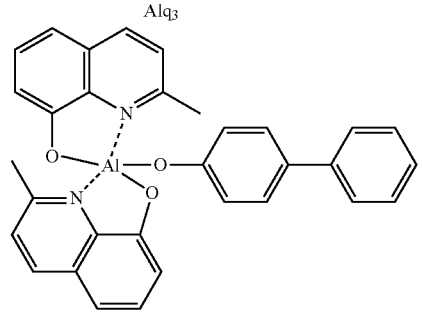

BAlq

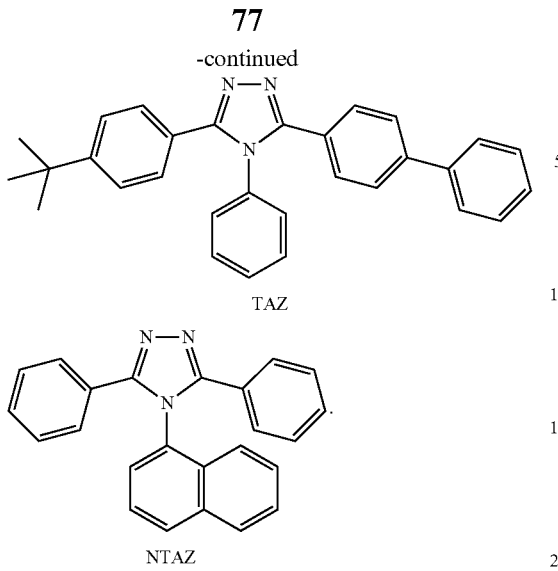

TAZ

NTAZ

In various embodiments, the electron transport layer may include at least one selected from Compounds ET1, ET2, and ET3, but embodiments are not limited thereto:

ET1

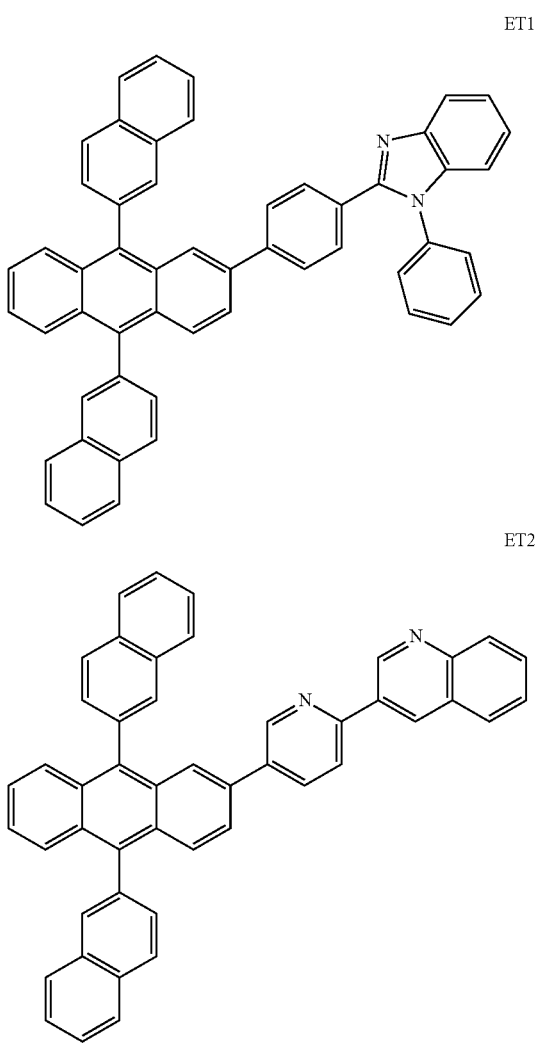

ET2

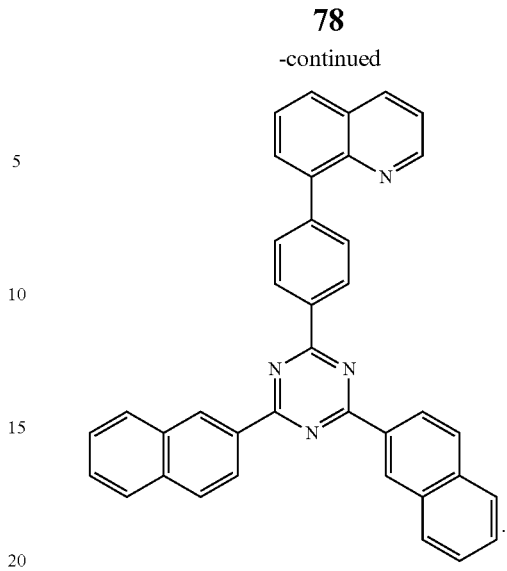

ET3

A thickness of the electron transport layer may be in a range of about 100 Å to about 1,000 Å, and in some embodiments, about 150 Å to about 500 Å. While not wishing to be bound by theory, it is understood that when the thickness of the electron transport layer is within these ranges, excellent electron transport characteristics may be achieved without a substantial increase in driving voltage.

Also, the electron transport layer may further include, in addition to the materials described above, a metal-containing material.

The metal-containing material may include a Li complex. The Li complex may include, for example, Compound ET-D1 (lithium 8-hydroxy quinolate, LiQ) or ET-D2:

ET-D1

ET-D2

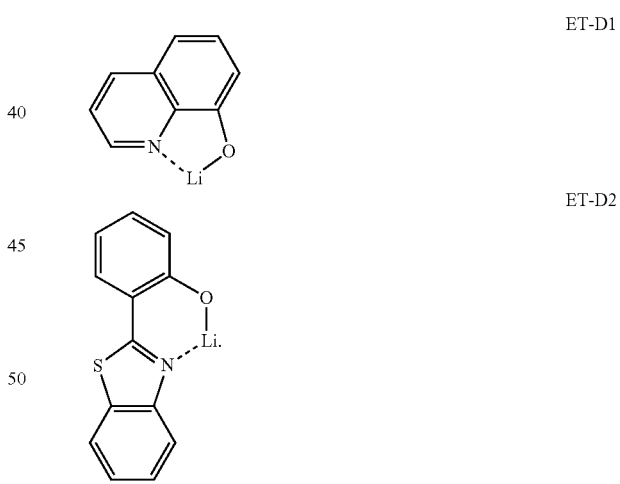

The electron transport region may include an electron injection layer that facilitates electron injection from the second electrode 19.

The electron injection layer may include at least one selected from LiF, NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within these ranges, excellent electron injection characteristics may be achieved without a substantial increase in driving voltage.

The second electrode 19 may be on the organic layer 15. The second electrode 19 may be a cathode. A material for the second electrode 19 may be a material having a relatively low work function, such as a metal, an alloy, an electrically conductive compound, and a composition thereof. Detailed examples of the material for forming the second electrode 19 may include lithium (Li), magnesium (Mg), aluminum (Al), aluminum-lithium (Al—Li), calcium (Ca), magnesium-indium (Mg—In), and magnesium-silver (Mg—Ag). In some embodiments, ITO or IZO may be used to form a transmissive second electrode 19 to manufacture a top emission light-emitting device, and such a variation may be possible.

Hereinbefore the organic light-emitting device 10 has been described with reference to FIG. 1, but embodiments are not limited thereto.

The term "$C_1$-$C_{60}$ alkyl group" as used herein refers to a linear or branched aliphatic saturated hydrocarbon monovalent group having 1 to 60 carbon atoms. Detailed examples thereof may include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group). Non-limiting examples thereof include a methoxy group, an ethoxy group, and an iso-propyloxy group.

The term "$C_2$-$C_{60}$ alkenyl group" as used herein refers to a group formed by placing at least one carbon-carbon double bond in the middle or at the terminus of the $C_2$-$C_{60}$ alkyl group. Detailed examples thereof may include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a group formed by placing at least one carbon-carbon triple bond in the middle or at the terminus of the $C_2$-$C_{60}$ alkyl group. Detailed examples thereof may include an ethenyl group and a propenyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms. Non-limiting examples thereof may include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group including at least one heteroatom selected from N, O, P, Si, and S as a ring-forming atom and 1 to 10 carbon atoms. Detailed examples thereof may include a tetrahydrofuranyl group and a tetrahydrothiophenyl group. The term "$C_1$-$C_{10}$ heterocycloalkylene group" used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in its ring, and which is not aromatic. Detailed examples thereof may include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, P, Si, and S as a ring-forming atom, 1 to 10 carbon atoms, and at least one carbon-carbon double bond in its ring. Examples of the $C_1$-$C_{10}$ heterocycloalkenyl group may include a 2,3-dihydrofuranyl group and a 2,3-dihydrothiophenyl group. The term "$C_1$-$C_{10}$ heterocycloalkylene group" as used herein refers to a divalent group having the same structure as the $C_1$-$C_{10}$ heterocycloalkyl group.

The term "$C_6$-$C_{60}$ aryl group" as used herein refers to a monovalent group having a carbocyclic aromatic system having 6 to 60 carbon atoms. The term "$C_6$-$C_{60}$ arylene group" as used herein refers to a divalent group having a carbocyclic aromatic system having 6 to 60 carbon atoms. Detailed examples of the $C_6$-$C_{60}$ aryl group may include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having an aromatic system including at least one heteroatom selected from N, O, P, Si, and S as a ring-forming atom and 1 to 60 carbon atoms. The term "$C_1$-$C_{60}$ heteroarylene group" as used herein refers to a divalent group having a heterocyclic aromatic system including at least one heteroatom selected from N, O, P, Si, and S as a ring-forming atom and 1 to 60 carbon atoms. Detailed examples of the $C_1$-$C_{60}$ heteroaryl group may include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" as used herein refers to —$OA_{102}$ (wherein $A_{102}$ is the $C_6$-$C_{60}$ aryl group). The term "$C_6$-$C_{60}$ arylthio group" as used herein indicates —$SA_{103}$ (wherein $A_{103}$ is the $C_6$-$C_{60}$ aryl group). The term "$C_7$-$C_{60}$ arylalkyl group" as used herein indicates -$A_{104}A_{105}$ (wherein $A_{104}$ is the $C_6$-$C_{59}$ aryl group and $A_{105}$ is the $C_1$-$C_{53}$ alkyl group).

The term "$C_2$-$C_{60}$ heteroaryloxy group" as used herein indicates —$OA_{106}$ (wherein $A_{106}$ is the $C_2$-$C_{60}$ heteroaryl group). The term "$C_2$-$C_{60}$ heteroarylthio group" as used herein indicates —$SA_{107}$ (wherein $A_{107}$ is the $C_2$-$C_{60}$ heteroaryl group). The term "$C_3$-$C_{60}$ heteroarylalkyl group" as used herein indicates -$A_{108}A_{109}$ (wherein $A_{108}$ is the $C_2$-$C_{59}$ heteroaryl group and $A_{109}$ is the $C_1$-$C_{58}$ alkyl group).

The term "monovalent non-aromatic condensed polycyclic group" as used herein refers to a monovalent group that has two or more rings condensed to each other and has only carbon atoms (for example, the number of carbon atoms may be in a range of 8 to 60) as ring-forming atom, wherein the molecular structure as a whole is non-aromatic. Non-limiting examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group that has a plurality of rings condensed with each other, has a heteroatom selected from N, O, P, and S, other than carbon atoms (for example, the number of carbon atoms may be in a range of 2 to 60), as ring-forming atoms, wherein the molecular structure as a whole is non-aromatic. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

In the present specification, at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_1$-$C_{60}$ heteroaryloxy group, substituted $C_1$-$C_{60}$ heteroarylthio group, substituted $C_2$-$C_{60}$ heteroarylalkyl group, substituted monovalent non-aromatic condensed polycyclic group, and substituted monovalent non-aromatic condensed heteropolycyclic group may be:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, or a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), or —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may be each independently hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, or a monovalent non-aromatic condensed heteropolycyclic group.

When a group containing a specified number of carbon atoms is substituted with any of the groups listed in the preceding paragraphs, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{60}$ alkyl" refers to a $C_1$-$C_{60}$ alkyl group substituted with $C_6$-$C_{60}$ aryl group, the total number of carbon atoms in the resulting aryl substituted alkyl group is $C_7$-$C_{120}$.

The term "room temperature" as used herein refers to a temperature of about 25° C.

Hereinafter the organic light-emitting device according to an embodiment will be described in detail with reference to Synthesis Examples and Examples, however, the inventive concept is not limited thereto. The wording "B was used instead of A" used in describing Synthesis Examples means that an amount of B used was identical to an amount of A used based on molar equivalence.

EXAMPLES

Synthesis Example 1: Synthesis of Compound A1

52 millimoles (mmol) of 3,6-dicyanocarbazole, 52 mmol of 9-(3-bromophenyl)-9H-carbazole, 8.8 grams (g) of CuI, 15.9 g of $K_2CO_3$, and 2.5 g of 1,10-phenanthroline were added to a 2-neck round bottom flask of 250 milliliters (mL), followed by addition of 150 mL of dimethylformamide (DMF). Subsequently, the composition was stirred at a temperature of 150° C. for 28 hours. The resultant was then cooled, and MeOH was added thereto to precipitate a solid for filtering. The resulting product was mixed with 1 liter (L) of chloroform, heated, and dissolved. Filtrate obtained by filtration using a celite pad was concentrated under reduced pressure. The obtained product was recrystallized using methylene chloride (MC) and acetone, thereby obtaining 10.9 g of Compound A1 (yield: 65.3%).

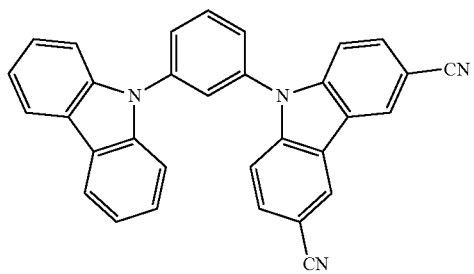

A1

Calc: 458.15, found [M+H$^+$]: 459.16

Evaluation Example 1: Evaluation of PL Spectrum and TRPL Spectrum

A quartz substrate washed with chloroform and pure water was prepared. The material shown in Table 1 was vacuum-(co)deposited on the quartz substrate at a vacuum degree of 10$^{-7}$ torr to prepare a film, D2, A1, D2:A1, A2, D2:A2, D3, A3, D3:A3, D3:A3:TBPe, D3:TBPe, D4, A4, D4:A4, D4:A4:TBPe, D4:TBPe, BmPyPb, TCTA, TCTA:BmPyPb, CBP:B3PYMPM, or TCTA:3TPYMB, each having a thickness of 50 nanometers (nm).

TABLE 1

| Name of film | Compound used in film preparation |
| --- | --- |
| Film D2 | Compound D2 |
| Film A1 | Compound A1 |
| Film D2:A1 | Compound D2:Compound A1 (at a volume ratio of 1:1) |
| Film A2 | Compound A2 |
| Film D2:A2 | Compound D2:Compound A2 (at a volume ratio of 1:1) |
| Film D3 | Compound D3 |
| Film A3 | Compound A3 |
| Film D3:A3 | Compound D3:Compound A3 (at a volume ratio of 1:1) |
| Film D3:A3:TBPe | Compound D3:Compound A3:TBPe (at a volume ratio of 49.5:49.5:1) |
| Film D3:TBPe | Compound D3:TBPe (at a volume ratio of 99:1) |
| Film D4 | Compound D4 |
| Film A4 | Compound A4 |
| Film D4:A4 | Compound D4:Compound A4 (at a volume ratio of 1:1) |
| Film D4:A4:TBPe | Compound D4:Compound A4:TBPe (at a volume ratio of 49.5:49.5:1) |
| Film D4:TBPe | Compound D4:TBPe (at a volume ratio of 99:1) |
| Film TCTA | TCTA |
| Film BmPyPb | BmPyPb |

TABLE 1-continued

| Name of film | Compound used in film preparation |
| --- | --- |
| Film TCTA:BmPyPb | TCTA:BmPyPb (at a volume ratio of 1:1) |
| Film CBP:B3PYMPM | CBP:B3PYMPM (at a volume ratio of 1:1) |
| Film TCTA:3TPYMB | TCTA:3TPYMB (at a volume ratio of 1:1) |

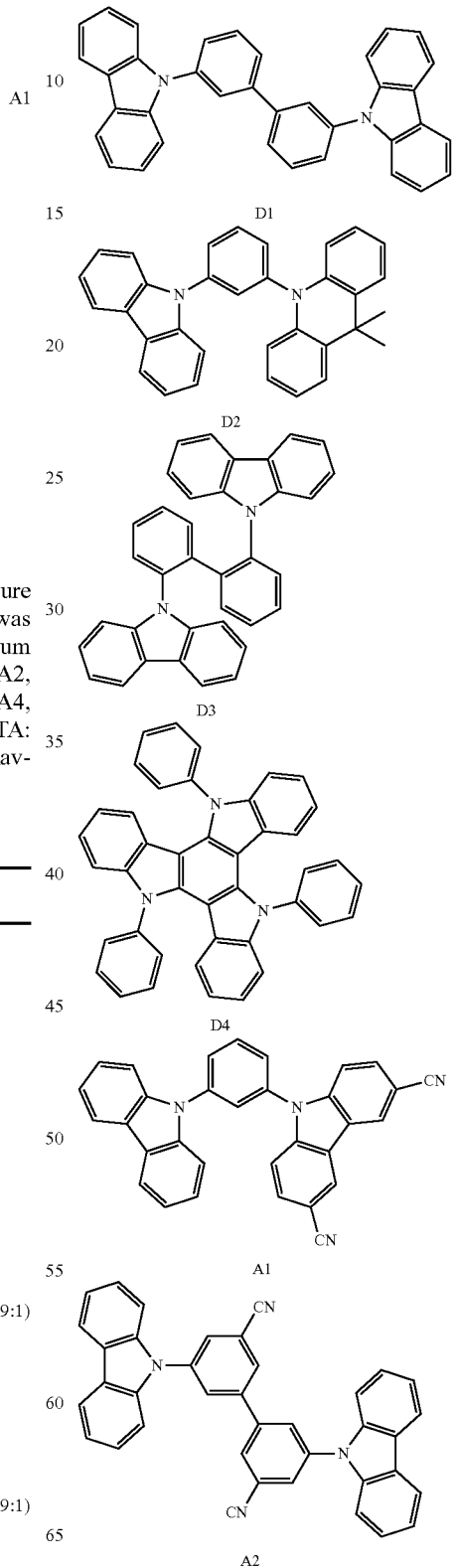

TABLE 1-continued

| Name of film | Compound used in film preparation |
| --- | --- |
| A3 | [structure] |
| A4 | [structure] |
| Compound FD(5): TBPe | [structure] |
| TCTA | [structure] |
| BmPyPb | [structure] |
| CBP | [structure] |
| B3PYMPM | [structure] |
| 3TPYMB | [structure] |

Subsequently, the PL spectrum of the prepared Films, D2, A1, D2:A1, A2, D2:A2, D3, A3, D3:A3, D4, A4, D4:A4, TCTA, BmPyPb, and TCTA:BmPyPb, were evaluated using an absolute PL quantum yield measurement system, Quantaurus-QY (available from Hamamatsu) at room temperature. The results thereof are shown in FIGS. 2A to 2E.

Figure 2A:
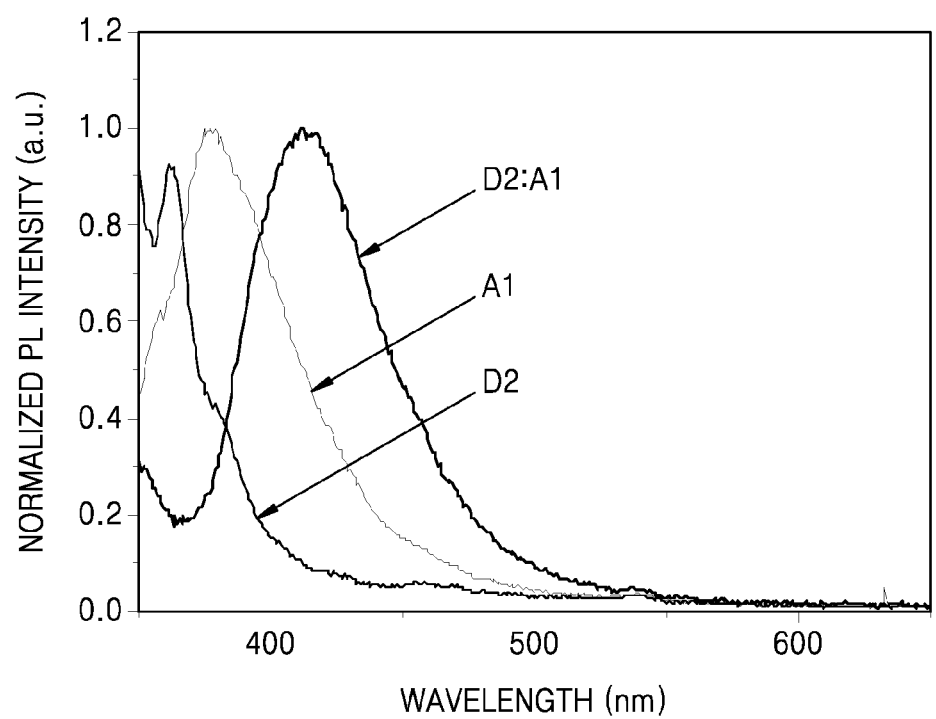
FIGS. 2A to 2E are graphs of normalized photoluminescence (PL) intensity (arbitrary units, a. u.) versus wavelength (nanometers, nm), which are representations of photoluminescence spectra of films measured in Evaluation Example 1.
Figure 2B:
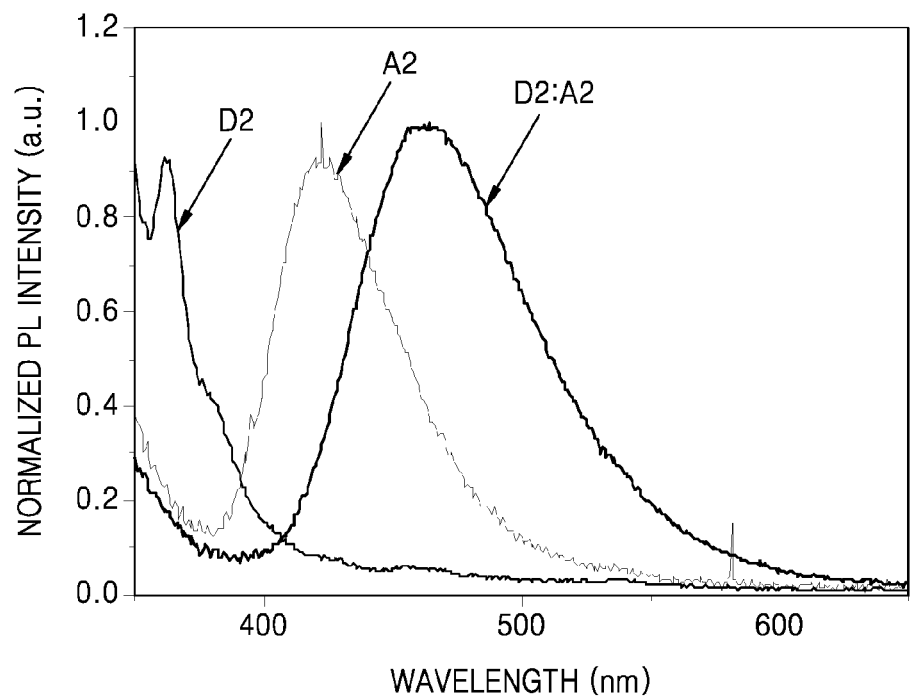
Figure 2C:
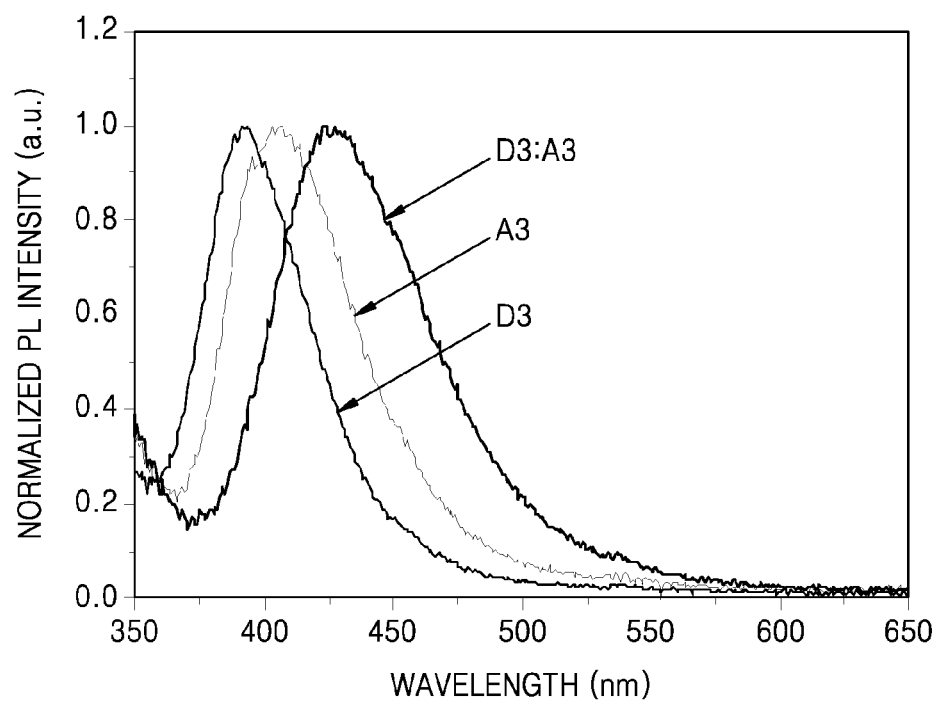
Figure 2D:
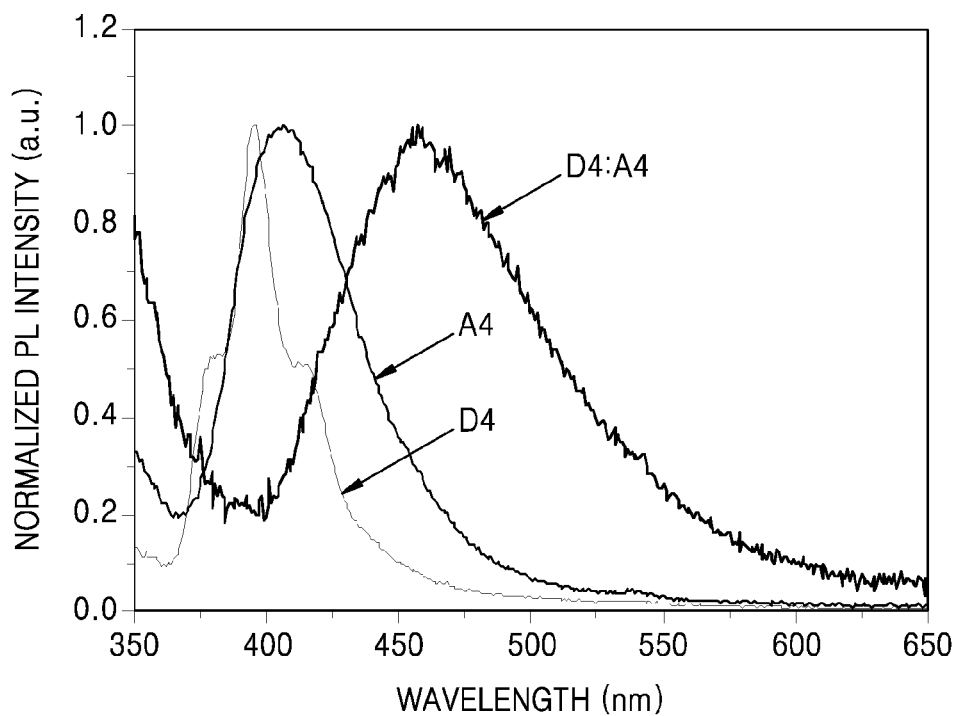
Figure 2E:
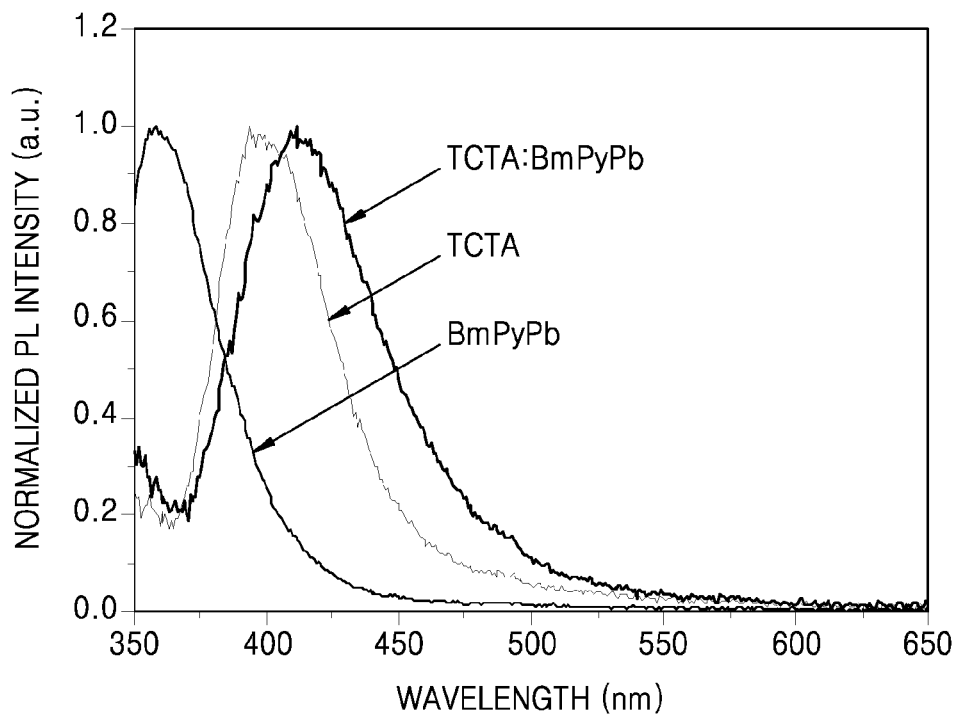
Figure 3A:
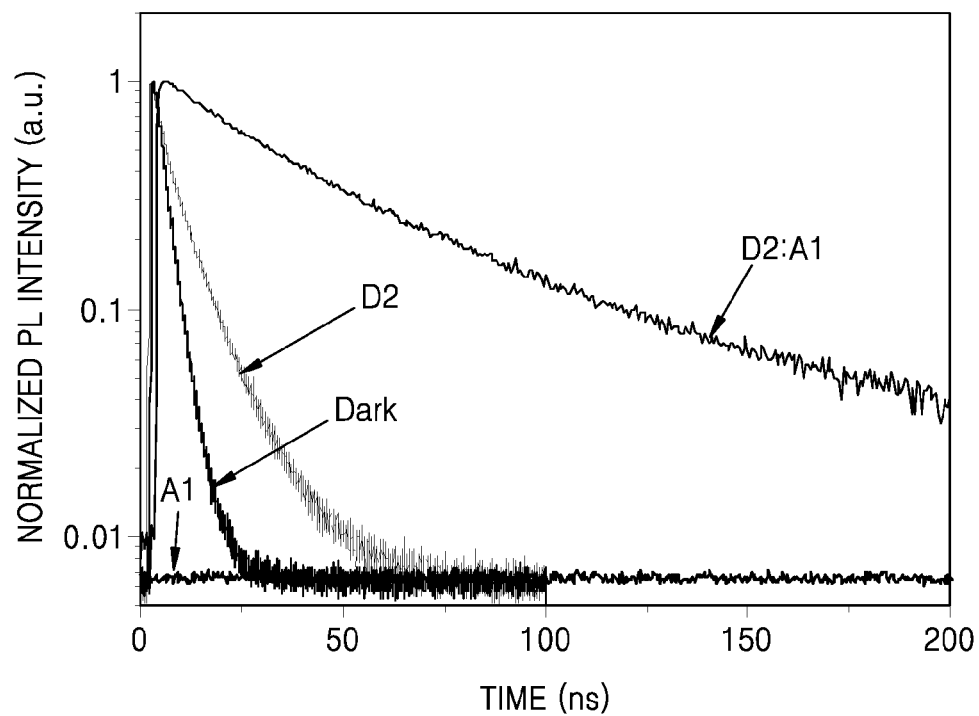
FIGS. 3A to 3G are graphs of normalized photoluminescence (PL) intensity (arbitrary units, a. u.) versus time (nanoseconds, ns), which are representations of time-resolved photoluminescence (TRPL) spectra in films measured in Evaluation Example 1.
Figure 3B:
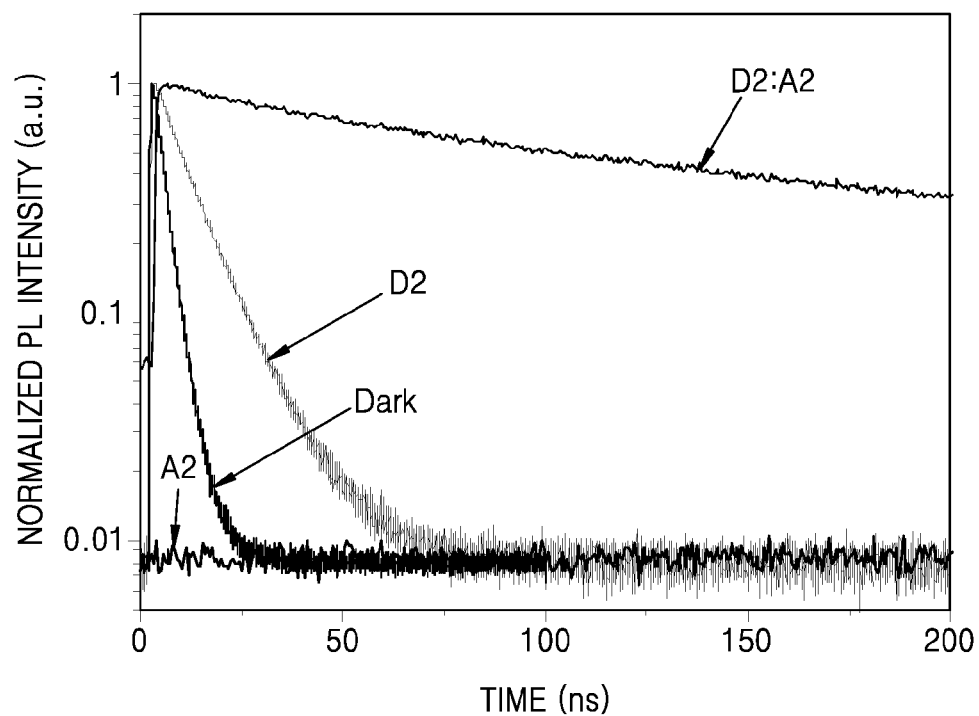
Figure 3C:
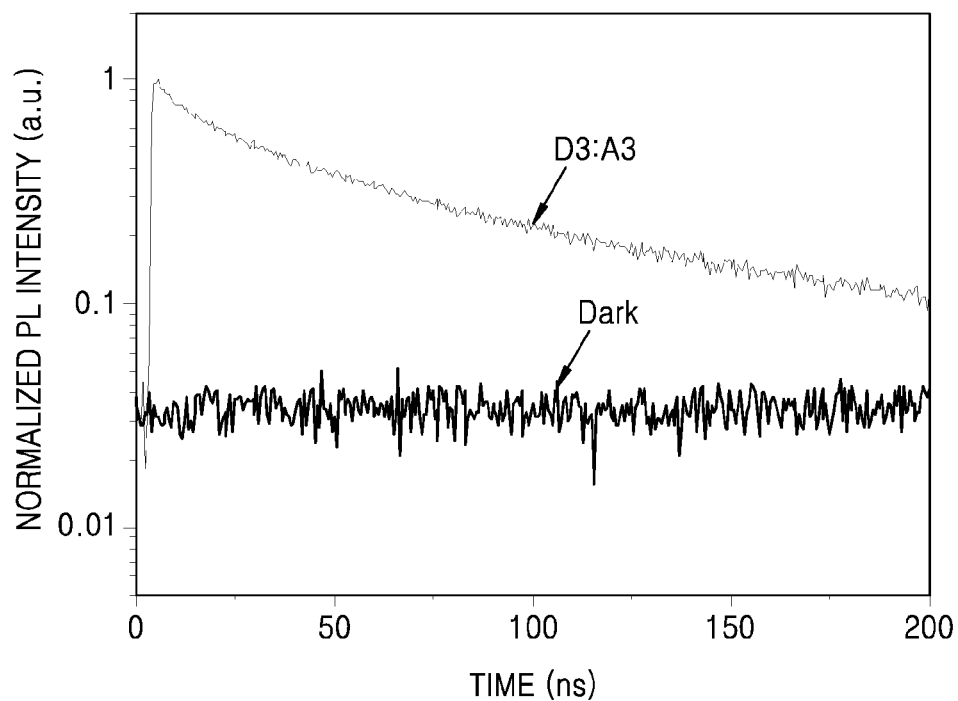
Figure 3D:
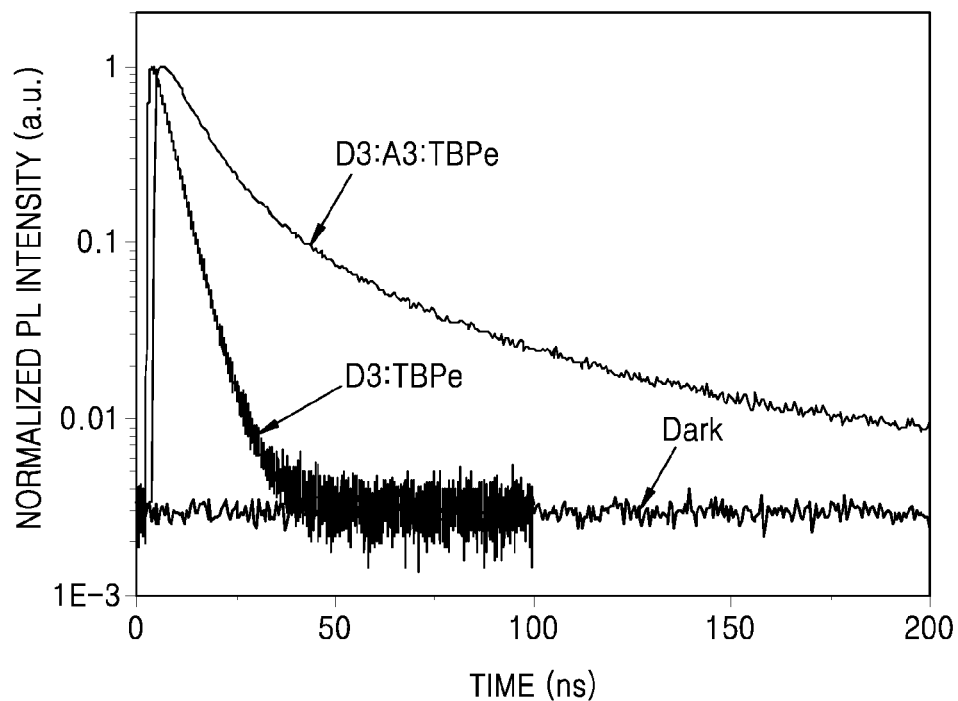
Figure 3E:
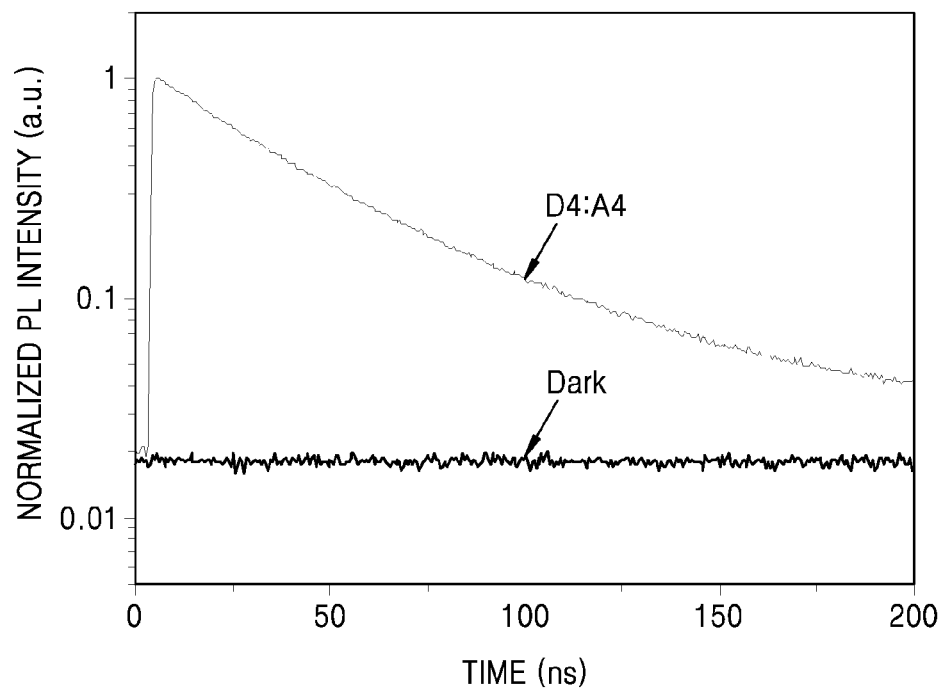
Figure 3F:
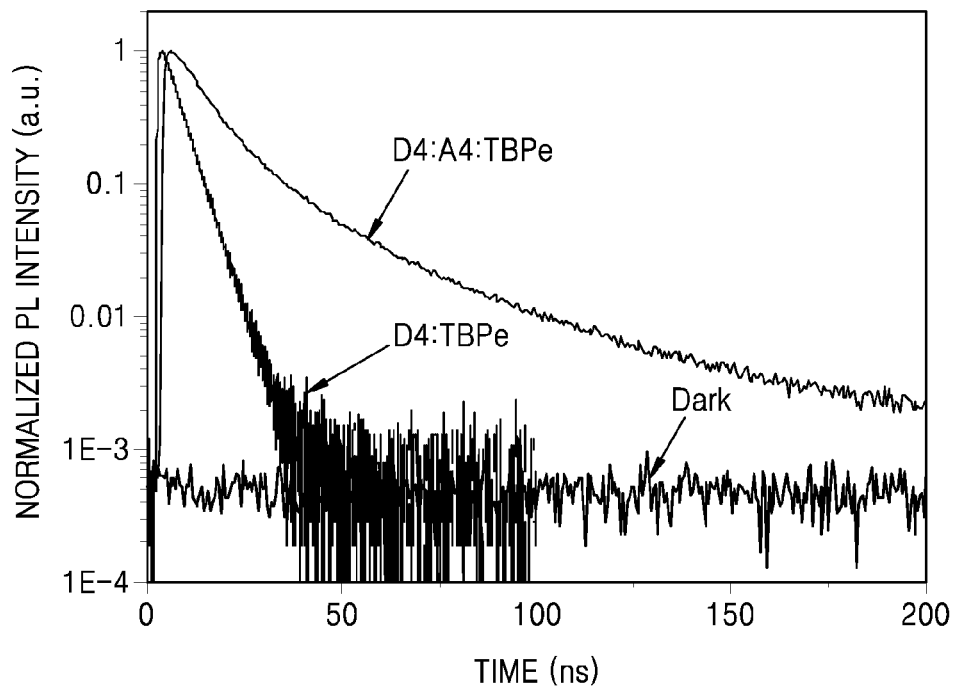
Figure 3G:
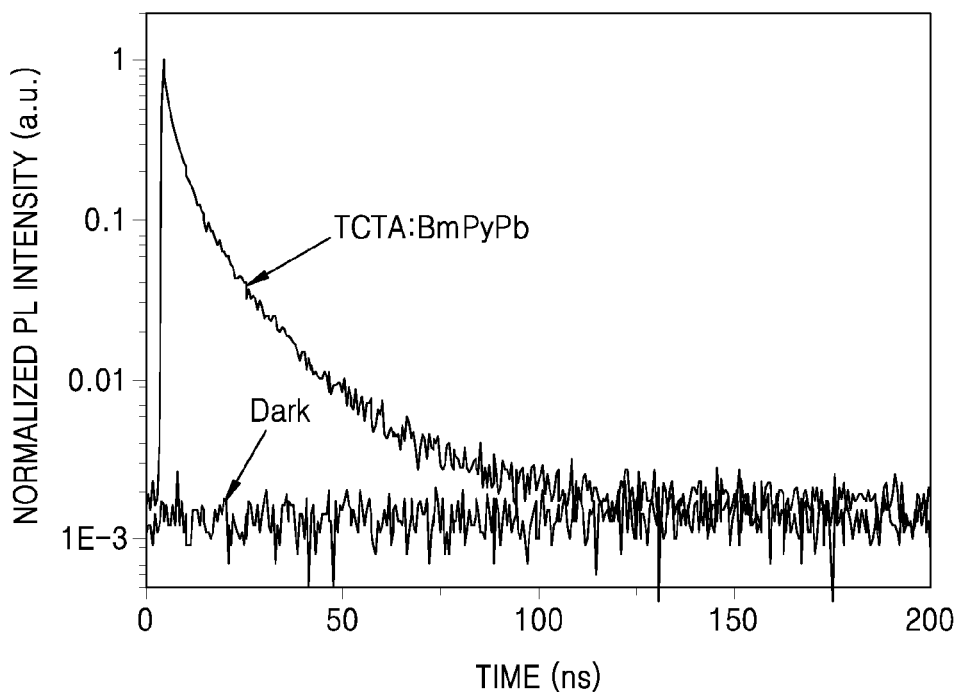
Figure 4A:
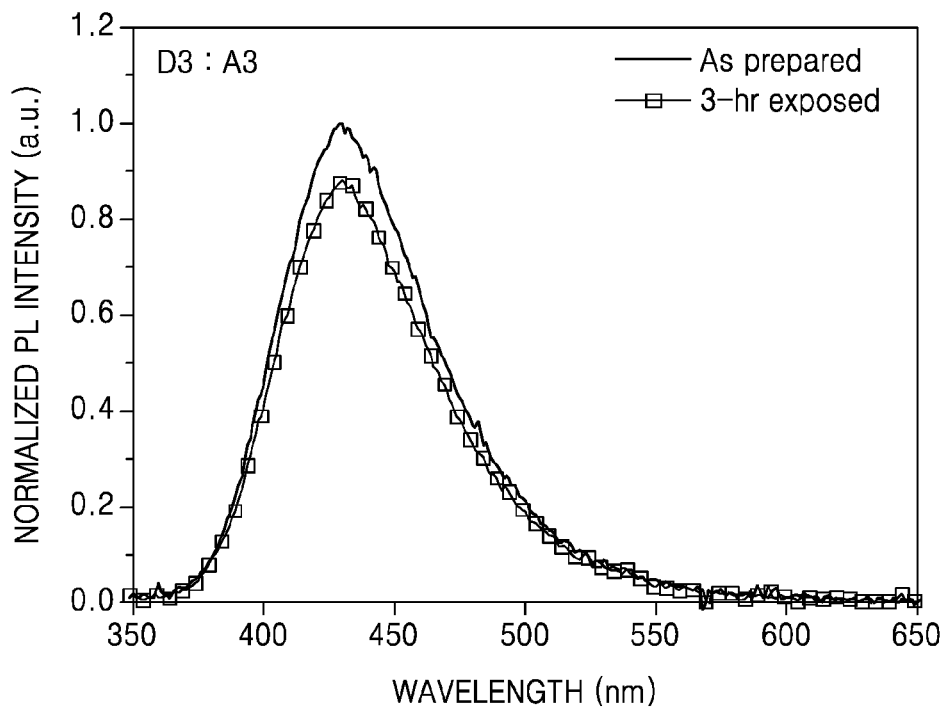
FIGS. 4A to 4D are graphs of normalized photoluminescence (PL) intensity (arbitrary units, a. u.) versus wavelength (nanometers, nm), which are representations of a PL spectrum ("As prepared") measured immediately after formation of each of Films D3:A3, TCTA:BmPyPb, CBP.
Figure 4B:
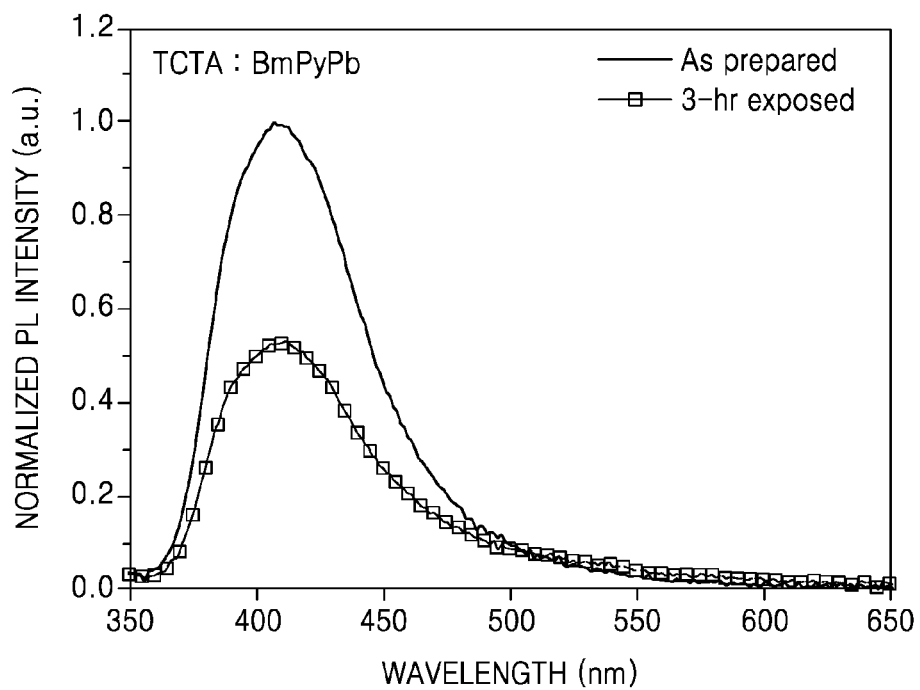
Figure 4C:
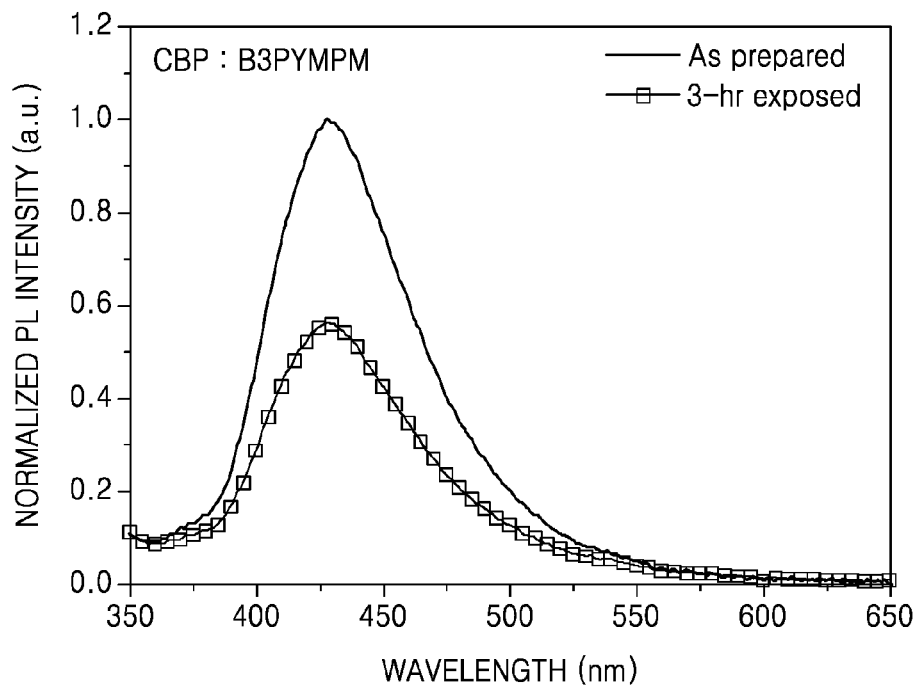
Figure 4D:
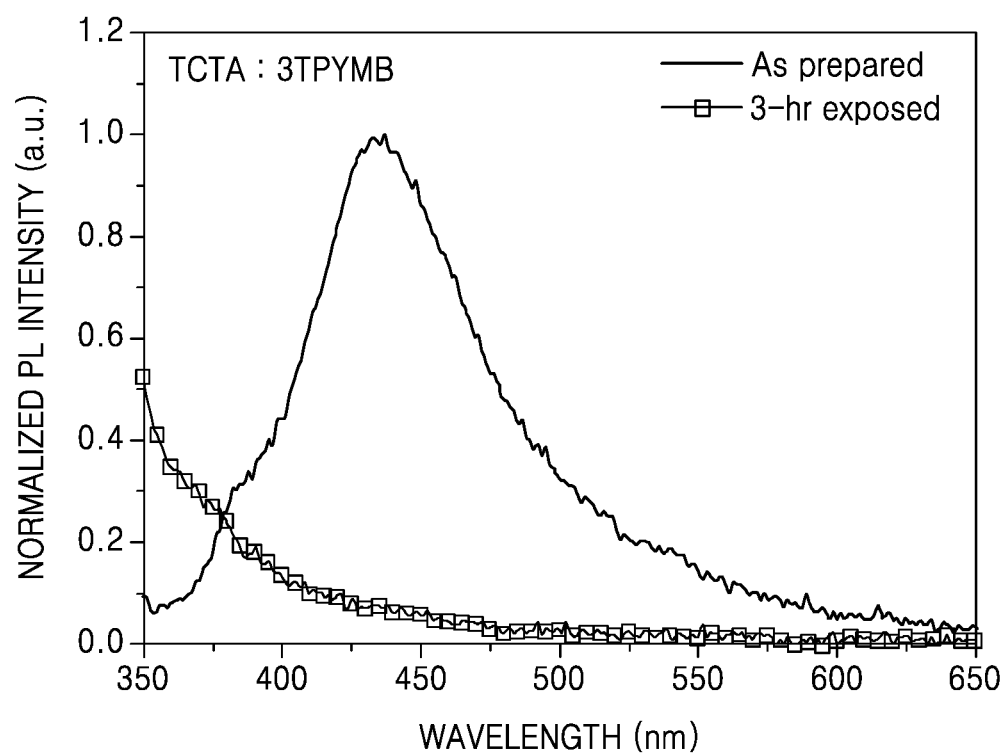

In FIG. 2A, the PL spectrum of Film D2:A1 was found to be shifted toward a longer wavelength range, as compared with those of Film D2 and Film A1. In FIG. 2B, the PL spectrum of Film D2:A2 was found to be shifted toward a longer wavelength range, as compared with those of Film D2 and Film A2. In FIG. 2C, the PL spectrum of Film D3:A3 was found to be shifted toward a longer wavelength range, as compared with those of Film D3 and Film A3. In FIG. 2D, the PL spectrum of Film D4:A4 was found to be shifted toward a longer wavelength range, as compared with those of Film D4 and Film A4. Accordingly, it was found that the combinations of compounds used in preparation of Film D2:A1, Film D2:A2, Film D3:A3, and Film D4:A4 each formed an exciplex.

In addition, in FIG. 2A, $\lambda_{max}$ of Film D2:A1 was about 425 nm. In FIG. 2B, $\lambda_{max}$ of Film D2:A2 was about 465 nm. In FIG. 2C, $\lambda_{max}$ of Film D3:A3 was about 430 nm. In FIG. 2D, $\lambda_{max}$ of Film D4:A4 was about 470 nm. The exciplex formed from Compounds D2 and A1, the exciplex formed from Compounds D2 and A2, the exciplex formed from Compounds D3 and A3, and the exciplex formed from Compounds D4 and A4 were each found to emit blue light.

Subsequently, the PL spectra of Films D2:A1, D2:A2, D3:A3, D3:A3:TBPe, D3:TBPe, D4:A4, D4:A4:TBPe, D4:TBPe, and TCTA:BmPyPb were evaluated at room temperature by using a TRPL measurement system, FluoTime 300 (manufactured by PicoQuant), and a pumping laser, PLS340 (manufactured by PicoQuant, excitation wavelength=340 nm, spectral width=20 nm). Then, a wavelength of main peaks in the PL spectra was determined, and upon photon pulses (pulse width=500 picoseconds, ps) applied to the films by PLS340, the number of photons emitted at a wavelength of main peaks for each of the films was repeatedly measured with time by time-correlated single photon counting (TCSPC), thereby obtaining TRPL curves available for the sufficient fitting. Based on the results obtained therefrom, two or more exponential decay functions were set forth for the fitting, thereby obtaining a decay time $T_{decay}$ (Ex) for each of Films D2:A1, D2:A2, D3:A3, D3:A3:TBPe, D4:A4, D4:A4:TBPe, and TCTA:BmPyPb. The functions used for the fitting are the same as described in Equation 1, and a decay time $T_{decay}$ having the largest value among values for each of the exponential decay functions used for the fitting was taken as a decay time $T_{decay}$ (Ex). The remaining decay time $T_{decay}$ values were used to determine the lifetime of typical fluorescence to be decayed. Here, during the same measurement time as the measurement time for obtaining TRPL curves, the same measurement was repeated once more at the dark state (i.e., a state where a pumping signal incident on a predetermined film was blocked), thereby obtaining a baseline or a background signal curve available as a baseline for the fitting.

Subsequently, the exponential decay curve (=changes in intensity over time), which was to be determined as the decay time $T_{decay}$ (Ex), was measured with respect to an integrated value of time-dependent intensity of the overall emission, and accordingly, a ratio of the integrated value over time was calculated, thereby evaluating the ratio of delayed fluorescent to the overall light-emitting portions.

$$f(t) = \sum_{i=1}^{n} A_i \exp(-t/T_{decay,i})$$ Equation 1

In the graphs of Films D2:A1, D2:A2, D3:A3, D3:A3:TBPe, D4:A4, D4:A4:TBPe, and TCTA:BmPyPb in FIGS. 3A to 3G, $T_{decay}$(Ex) and the ratio of a delayed fluorescence portion to the overall light-emitting portions are shown in Table 2:

TABLE 2

| Film | $T_{decay}$ (Ex) | Ratio of a delayed fluorescence portion to the overall light-emitting portions (%) |
|---|---|---|
| Film D2:A1 | 238 nanoseconds (ns) | 15.5 |
| Film D2:A2 | 515 ns | 37.8 |
| Film D3:A3 | 193 ns | 53.53 |
| Film D3:A3:TBPe | 318 ns | 24.78 |
| Film D4:A4 | 2.729 microseconds (μs) | 37.85 |
| Film D4:A4:TBPe | 1.738 μs | 15.16 |
| Film TCTA:BmPyPb | 75 ns | 4 |

Accordingly, i) the exciplex formed from Compounds D2 and A1, ii) the exciplex formed from Compounds D2 and A2, iii) the exciplex formed from Compounds D3 and A3, iv) the combination of the exciplex formed from Compounds D3 and A3; and TBPe, v) the exciplex formed from Compounds D4 and A4, and vi) the combination of the exciplex formed from Compounds D4 and A4; and TBPe were found to have both $T_{decay}$(Ex) of about 100 ns or greater (e.g., 150 ns or greater) and a ratio of the delayed fluorescence portion to the overall light-emitting portions of about 10% or greater (e.g., 15% or greater).

On the other hand, a ratio of the delayed fluorescence portion to the overall light-emitting portions in Film TCTA:BmPyPb was about 4%. Thus, the delayed fluorescence due to the exciplex in Film TCTA:BmPyPb was found to contribute to all the fluorescence in a relatively small degree.

Evaluation Example 2: Evaluation on HOMO and LUMO Energy Levels

Following the methods shown in Table 3, the HOMO and LUMO energy levels of Compounds D1, A1, D2, A2, D3, A3, D4, and A4 were evaluated. The results thereof are shown in Table 4.

TABLE 3

| | |
|---|---|
| HOMO energy level evaluation method | A potential (Volts, V) versus current (Amperes, A) graph of each compound was obtained by using CV (electrolyte: 0.1 molar (M) Bu$_4$NPF$_6$/solvent: CH$_2$Cl$_2$/electrode: 3-electrode system (working electrode: Pt disc (1 mm diameter), reference electrode: Pt wire, and auxiliary electrode: Pt wire)). Subsequently, the HOMO energy level of the compound was calculated from oxidation onset of the graph. |
| LUMO energy level evaluation method | Each compound was diluted with CHCl$_3$ at a concentration of 1 × 10$^{-5}$M, and a UV absorption spectrum thereof was measured at room temperature by using a Shimadzu UV-350 spectrometer. An optical band gap (Eg) was obtained from an edge of the UV absorption spectrum, and then the LUMO energy level thereof was calculated by using the optical band gap (Eg) and the HOMO energy level. |

TABLE 4

| Compound | HOMO energy level (eV) (measured) | LUMO energy level (eV) (measured) | Compound | HOMO energy level (eV) (measured) | LUMO energy level (eV) (measured) |
|---|---|---|---|---|---|
| D1 | −5.658 | −2.088 | A1 | −5.709 | −2.152 |
| D2 | −5.393 | −1.802 | A2 | −5.426 | −2.058 |
| D3 | −5.489 | −2.02 | A3 | −5.677 | −2.108 |
| D4 | −5.368 | −2.008 | A4 | −5.57 | −1.98 |

Referring to Table 4, Compounds D1, A1, D2, A2, D3, A3, D4, and A4 were found to have suitable electric characteristics for forming an exciplex that may emit delayed fluorescence.

Evaluation Example 3: Photoluminance (PL) Stability Evaluation

Immediately after formation of Films D3:A3, TCTA:BmPyPb, CBP:B3PYMPM, and TCTA:3TPYMB, a PL spectrum of each of the Films was evaluated using He—Cd laser (available from Kimmon Koha Co., Ltd, excited wavelength=325 nm) in an argon atmosphere in which external air is cut off at room temperature. An intensity $I_1$ (arbitrary units, a.u.) of the light at a maximum emission wavelength in the PL spectrum was measured to each of the Films. The results thereof are shown in Table 5.

Subsequently, each of the Films D3:A3, TCTA:BmPyPb, CBP:B3PYMPM, and TCTA:3TPYMB was exposed for three hours to light of a pumping laser, He—Cd laser (available from Kimmon Koha Co., Ltd, excited wavelength=325 nm), used in the evaluation of $I_1$ in an argon atmosphere in which external air is cut off. Then, a PL spectrum of each of the Films, which are obtained after above the three-hour exposure, was evaluated using He—Cd laser (available from Kimmon Koha Co., Ltd, excited wavelength=325 nm) at room temperature. An intensity $I_2$ (a.u.) of the light at a maximum emission wavelength in the PL spectrum was then measured to each of the Films. The results thereof are shown in Table 5.

The PL spectrum (denoted as As prepared) that was measured immediately after the formation of each of Films D3:A3, TCTA:BmPyPb, CBP:B3PYMPM, and TCTA:3TPYMB, and the PL spectrum (denoted as 3-hr exposed) that was measured after the three-hour exposure to laser light are shown in FIGS. 4A to 4D.

From $I_1$ and $I_2$ that were measured as above, the PL stability of each Film was calculated by using $(I_2/I_1) \times 100$ (%). The results are shown in Table 5.

TABLE 5

| Film | $I_1$ (a.u.) | $I_2$ (a.u.) | $(I_2/I_1) \times 100$ (%) (PL stability) |
|---|---|---|---|
| Film D3:A3 | 0.045 | 0.039 | 87 |
| Film TCTA:BmPyPb | 0.067 | 0.039 | 58 |
| Film CBP:B3PYMPM | 0.078 | 0.044 | 56 |
| Film TCTA:3TPYMB | 0.028 | 0.008 | 29 |

Referring to Table 5, it was found that Film D3:A3 had higher PL stability, as compared with Films TCTA:BmPyPb, CBP:B3PYMPM, and TCTA:3TPYMB.

Example: Manufacture of Organic Light-Emitting Device (OLED)

As an anode, a glass substrate having an ITO electrode thereon was cut to a size of 50 millimeters (mm)×50 mm×0.5 mm. Then the glass substrate was sonicated in acetone iso-propyl alcohol and pure water for about 15 minutes in each solvent, and cleaned by exposure to ultraviolet rays with ozone for 30 minutes.

Compound HT3 and TCNPQ (wherein the concentration of TCNPQ was about 3 percent by weight (wt %)) were co-deposited on the anode to form a hole injection layer having a thickness of about 100 Å. Compound HT3 was then deposited on the hole injection layer to form a hole transport layer having a thickness of about 1,700 Å.

Compound D2 and Compound A2 were then co-deposited on the hole transport layer at a volume ratio of about 3:7 to form an emission layer having a thickness of about 400 Å.

Compound ET16 and LiQ were co-deposited on the emission layer at a weight ratio of about 5:5 to form an electron transport layer having a thickness of about 360 Å. Subsequently, LiQ was deposited on the electron transport layer to form an electron injection layer having a thickness of about 5 Å. MgAg electrode (wherein an amount of Ag was about 10 wt %) having a thickness of about 120 Å was formed on the electron injection layer. Compound HT13 was deposited on the MgAg electrode to form a capping layer having a thickness of about 600 Å, thereby completing the manufacture of an organic light-emitting device. The donor compound, the acceptor compound, and/or the fluorescent dopant and the volume ratio thereof used in the formation of an emission layer of the manufactured OLEDs 1 to 3 and A and B are as shown in Table 6.

TABLE 6

| OLED | Donor compound | Acceptor compound | Fluorescent dopant | Volume ratio |
|---|---|---|---|---|
| 1 | Compound D2 | Compound A2 | — | 3:7 |
| 2 | Compound D2 | Compound A2 | TBPe | 29.7:69.3:1 |
| 3 | Compound D3 | Compound A3 | TBPe | 29.7:69.3:1 |
| A | TCTA | BmPyPb | — | 3:7 |
| B | TCTA | BmPyPb | TBPe | 29.7:69.3:1 |

Evaluation Example 4

The driving voltage, luminance, power, color-coordinates, roll-off, and lifespan ($T_{95}$) of the manufactured OLEDs 1 to 3 and A and B were measured by using a Keithley 2400 current voltmeter and a luminance meter (Minolta Cs-1000A). The results thereof are shown in Table 7. In Table 7, $T_{95}$ represents lifespan data evaluating a period taken for the luminance (at 9,000 nit) to reach 95% with respect to 100% of the initial luminance. The roll-off was calculated following Equation 20:

Roll off={1−(efficiency (at 9,000 nit)/maximum emission efficiency)}×100%  Equation 20

TABLE 7

| OLED | Donor compound | Acceptor compound | Fluorescent dopant | Driving voltage (V) | Efficiency (cd/A) | CIE_x | CIE_y | Roll off (%) | Lifespan ($L_{95}$) (hr) |
|---|---|---|---|---|---|---|---|---|---|
| 1 | Compound D2 | Compound A2 | — | 4.44 | 1.04 | 0.152 | 0.115 | 4.8 | 0.41 |
| 2 | Compound D2 | Compound A2 | TBPe | 4.79 | 4.10 | 0.143 | 0.232 | 28.4 | 1.81 |

TABLE 7-continued
| OLED | Donor compound | Acceptor compound | Fluorescent dopant | Driving voltage (V) | Efficiency (cd/A) | CIE_x | CIE_y | Roll off (%) | Lifespan (L$_{95}$) (hr) |
|---|---|---|---|---|---|---|---|---|---|
| 3 | Compound D3 | Compound A3 | TBPe | 4.79 | 4.66 | 0.141 | 0.224 | 26.1 | 1.29 |
| A | TCTA | BmPyPb | — | 5.31 | 0.81 | 0.170 | 0.077 | 7.2 | 0.01 |
| B | TCTA | BmPyPb | TBPe | 5.63 | 3.32 | 0.143 | 0.178 | 34.4 | 0.03 |
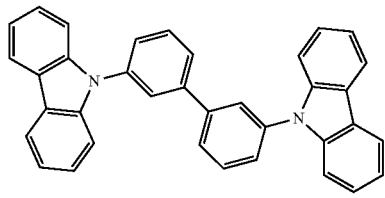
D1
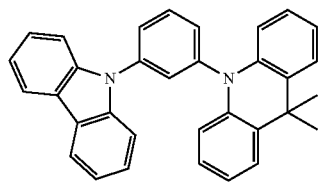
D2
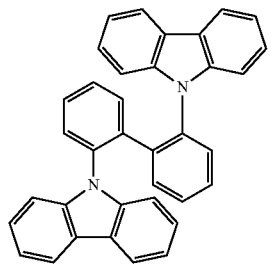
D3
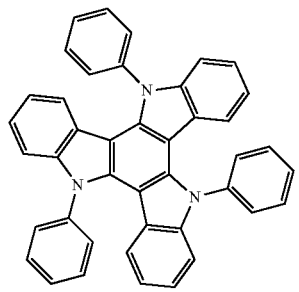
D4
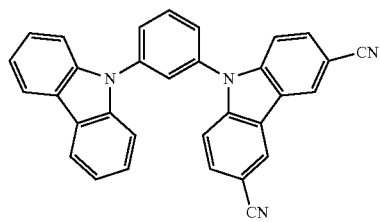
A1

TABLE 7-continued

| | Donor compound | Acceptor compound | Fluorescent dopant | Driving voltage (V) | Efficiency (cd/A) | CIE_x | CIE_y | Roll off (%) | Lifespan (L₉₅) (hr) |
|---|---|---|---|---|---|---|---|---|---|
| OLED | | | | | | | | | |

A2

A3

A4

TCTA

TABLE 7-continued

| OLED | Donor compound | Acceptor compound | Fluorescent dopant | Driving voltage (V) | Efficiency (cd/A) | CIE_x | CIE_y | Roll off (%) | Lifespan ($L_{95}$) (hr) |
|---|---|---|---|---|---|---|---|---|---|

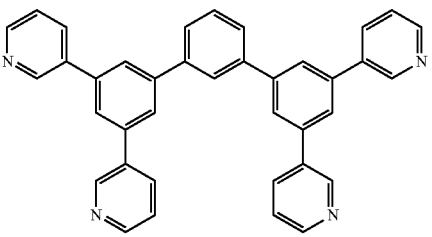

BmPyPb

Referring to Table 7, The OLED 1 was found to have low driving voltage, high efficiency, low roll-off, and long lifespan, as compared with the OLED A, and the OLEDs 2 and 3 were found to have low driving voltage, high efficiency, low roll-off, and long lifespan, as compared with the OLED B.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:

1. A composition comprising:
a donor compound and an acceptor compound,
wherein the donor compound and the acceptor compound form an exciplex,
wherein a maximum emission wavelength $\lambda_{max}$(Ex) in a photoluminescence spectrum of the exciplex is about 390 nanometers or greater and about 490 nanometers or less,
wherein a decay time $T_{decay}$(Ex) of delayed fluorescence in a time-resolved photoluminescence spectrum of the exciplex is about 100 nanoseconds or greater,
wherein a ratio of a delayed fluorescence portion to the overall light-emitting portions in the time-resolved photoluminescence spectrum of the exciplex is about 10% or greater,
wherein a photoluminescence stability of the exciplex is 60% or greater,
wherein the photoluminescence spectrum and the time-resolved photoluminescence spectrum of the exciplex are each a spectrum measured at room temperature with respect to a film that is formed by co-deposition of the donor compound and the acceptor compound on a substrate, and
wherein the photoluminescence stability of the exciplex is calculated according to Equation 10:

PL stability (%)=($I_2/I_1$)×100   Equation 10 wherein, in Equation 10,
$I_1$ is an intensity of a light at the maximum emission wavelength $\lambda_{max}$(Ex) in a photoluminescence spectrum of Film 1, which is obtained immediately after formation of a film by co-deposition of the donor compound and the acceptor compound on a substrate, measured at room temperature in an inert atmosphere in which external air is excluded, and
$I_2$ is an intensity of a light at the maximum emission wavelength $\lambda_{max}$(Ex) in a photoluminescence spectrum of Film 2, which is obtained after exposure of the Film 1 to pumping laser light used in the evaluation of $I_1$ in an inert atmosphere in which external air is excluded for 3 hours, measured at room temperature in an inert atmosphere in which external air is excluded.

2. The composition of claim 1, wherein the maximum emission wavelength $\lambda_{max}$(Ex) is about 390 nanometers or greater and about 440 nanometers or less.

3. The composition of claim 1, wherein
an absolute value of the highest occupied molecular orbital energy level of the donor compound |HOMO (D)| is about 5.78 electron volts or less,
an absolute value of the lowest unoccupied molecular orbital energy level of the acceptor compound |LUMO (A)| is about 1.76 electron volts or greater,
the highest occupied molecular orbital energy level of the donor compound is calculated by using cyclic voltammetry, and
the lowest unoccupied molecular orbital energy level of the acceptor compound is calculated by using an ultraviolet absorption spectrum measured at room temperature.

4. The composition of claim 1, wherein
an absolute value of the highest occupied molecular orbital energy level difference between the acceptor compound and the donor compound |HOMO (A)−HOMO (D)| is about 0.037 electron volts or greater and about 1.1 electron volts or less,
an absolute value of the lowest unoccupied molecular orbital energy level difference between the acceptor compound and the donor compound |LUMO (A)−LUMO (D)| is about 0.001 electron volts or greater and about 1.1 electron volts or less,
the highest occupied molecular orbital energy level of the donor compound is calculated by using cyclic voltammetry, and
the lowest unoccupied molecular orbital energy level of the acceptor compound is calculated by using an ultraviolet absorption spectrum measured at room temperature.

5. The composition of claim 1, wherein
the donor compound comprises at least one selected from a carbazole-containing ring, a dibenzofuran-containing ring, a dibenzothiophene-containing ring, an indenocarbazole-containing ring, an indolocarbazole-containing ring, a benzofurocarbazole-containing ring, a benzothienocarbazole-containing ring, an acridine-containing ring, a dihydroacridine-containing ring, and a tri-indolobenzene-containing ring, and the acceptor compound comprises at least one selected from a carbazole-containing ring, a dibenzofuran-containing ring, a dibenzothiophene-containing ring, an indenocarbazole-containing ring, an indolocarbazole-containing ring, a benzofurocarbazole-containing ring, a benzothienocarbazole-containing ring, a pyridine-containing ring, a pyrimidine-containing ring, and a triazine-containing ring.

6. The composition of claim 1, wherein
the donor compound does not comprise an electron withdrawing group, and
the acceptor compound comprises at least one electron withdrawing group,
wherein the electron withdrawing group is selected from —F, —CFH$_2$, —CF$_2$H, —CF$_3$, —CN, and —NO$_2$;
a C$_1$-C$_{60}$ alkyl group substituted with at least one selected from —F, —CFH$_2$, —CF$_2$H, —CF$_3$, —CN, and —NO$_2$;
a C$_1$-C$_{60}$ heteroaryl group and a monovalent non-aromatic condensed polycyclic heterocyclic group, each comprising *=N—*' as a ring-forming moiety; and
a C$_1$-C$_{60}$ heteroaryl group and a monovalent non-aromatic condensed polycyclic heterocyclic group, each comprising *=N—*' as a ring-forming moiety and each substituted with at least one selected from deuterium, —F, —CFH$_2$, —CF$_2$H, —CF$_3$, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_7$-C$_{60}$ arylalkyl group, a substituted or unsubstituted C$_1$-C$_{60}$ heteroaryl group, a substituted or unsubstituted C$_1$-C$_{60}$ heteroaryloxy group, a substituted or unsubstituted C$_1$-C$_{60}$ heteroarylthio group, a substituted or unsubstituted C$_2$-C$_{60}$ heteroarylalkyl group, a substituted or unsubstituted monovalent non-aromatic condensed polycyclic group, and a substituted or unsubstituted monovalent non-aromatic condensed heteropolycyclic group.

7. The composition of claim 1, wherein
the donor compound is selected from a compound represented by Formula D-1, and
the acceptor compound is selected from compounds represented by Formulae A-1 and A-2:

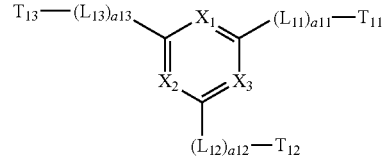

Formula D-1

Formula A-1

Formula A-2

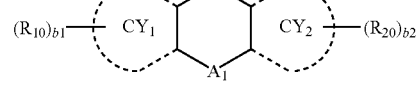

Formula 11

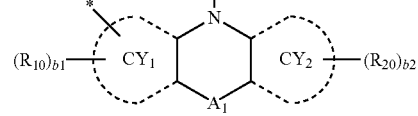

Formula 12

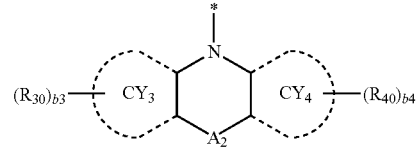

Formula 13

Formula 14

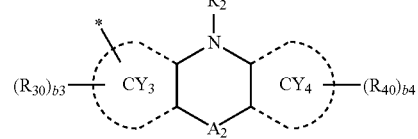

wherein, in Formulae D-1, A-1, A-2, and 11 to 14,
Ar$_1$ is selected from groups represented by Formulae 11 and 12,
Ar$_2$ is selected from
groups represented by Formulae 11 and 12, a phenyl group, and a naphthyl group; and
a phenyl group and a naphthyl group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a naphthyl group, a fluorenyl group, a carbazolyl group, a dibenzofuranyl group, and a dibenzothiophenyl group,
Ar$_{11}$ and Ar$_{12}$ are each independently selected from groups represented by Formulae 13 and 14,
X$_1$ is N or C(T$_{14}$), X$_2$ is N or C(T$_{15}$), X$_3$ is N or C(T$_{16}$), provided that at least one of X$_1$ to X$_3$ is N,
L$_1$ is selected from
a single bond, a phenylene group, a naphthylene group, a fluorenylene group, a carbazolylene group, a dibenzofuranylene group, and a dibenzothiophenylene group; and
a phenylene group, a naphthylene group, a fluorenylene group, a carbazolylene group, a dibenzofuranylene group, and a dibenzothiophenylene group, each substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, and —Si($Q_{11}$)($Q_{12}$)($Q_{13}$), $L_{11}$ to $L_{13}$ are each independently selected from a single bond, a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group; and a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, —$CFH_2$, a phenyl group, a phenyl group substituted with a cyano group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —Si($Q_{11}$)($Q_{12}$)($Q_{13}$), a1 and a11 to a13 are each independently an integer selected from 0 to 5, when a1 is 2 or greater, groups $L_1$ are identical to or different from each other, when a11 is 2 or greater, groups $L_{11}$ are identical to or different from each other, when a12 is 2 or greater, groups $L_{12}$ are identical to or different from each other, when a13 is 2 or greater, groups $L_{13}$ are identical to or different from each other, $CY_1$ to $CY_4$ are each independently selected from a benzene group, a naphthalene group, a fluorene group, a carbazole group, a benzocarbazole group, an indolocarbazole group, a dibenzofuran group, and a dibenzothiophene group, $A_1$ is selected from a single bond, a $C_1$-$C_4$ alkylene group, and a $C_2$-$C_4$ alkenylene group; and a $C_1$-$C_4$ alkylene group and a $C_2$-$C_4$ alkenylene group, each substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, and —Si($Q_{21}$)($Q_{22}$)($Q_{23}$), $A_2$ is selected from a single bond, a $C_1$-$C_4$ alkylene group, and a $C_2$-$C_4$ alkenylene group; and a $C_1$-$C_4$ alkylene group and a $C_2$-$C_4$ alkenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —Si($Q_{21}$)($Q_{22}$)($Q_{23}$), $R_1$, $R_{10}$, and $R_{20}$ are each independently selected from hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, and a dibenzothiophenyl group;

a phenyl group, a naphthyl group, a fluorenyl group, a carbazolyl group, a dibenzofuranyl group, and a dibenzothiophenyl group;

a phenyl group, a naphthyl group, a fluorenyl group, a carbazolyl group, a dibenzofuranyl group, and a dibenzothiophenyl group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, and a dibenzothiophenyl group; and —Si($Q_1$)($Q_2$)($Q_3$), $T_{11}$ to $T_{16}$, $R_2$, $R_{30}$, and $R_{40}$ are each independently selected from hydrogen, deuterium, —F, —Cl, —Br, —I, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$), b1 to b4 are each independently an integer selected from 0 to 10, and at least one of substituents of the substituted $C_1$-$C_{60}$ alkyl group, substituted $C_2$-$C_{60}$ alkenyl group, substituted $C_2$-$C_{60}$ alkynyl group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_1$-$C_{60}$ heteroaryloxy group, substituted $C_1$-$C_{60}$ heteroarylthio group, substituted $C_2$-$C_{60}$ heteroarylalkyl group, substituted monovalent non-aromatic condensed polycyclic group, and substituted monovalent non-aromatic condensed heteropolycyclic group is selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, and —Si$(Q_{31})(Q_{32})(Q_{33})$, wherein $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

8. The composition of claim 7, wherein
$Ar_1$ is selected from groups represented by Formulae 11-1 to 11-8 and 12-1 to 12-8,
$Ar_2$ is selected from groups represented by Formulae 11-1 to 11-8 and 12-1 to 12-8, a phenyl group, and a naphthyl group, and
$Ar_{11}$ and $Ar_{12}$ are each independently selected from groups represented by Formulae 13-1 to 13-8 and 14-1 to 14-8:

Formula 11-1

Formula 11-2

Formula 11-3

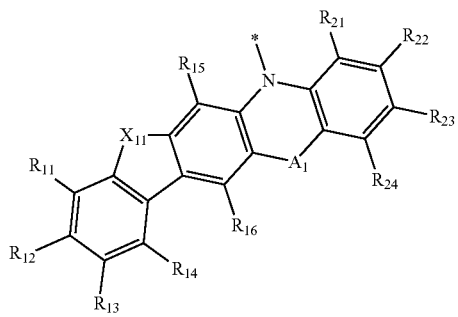

Formula 11-4

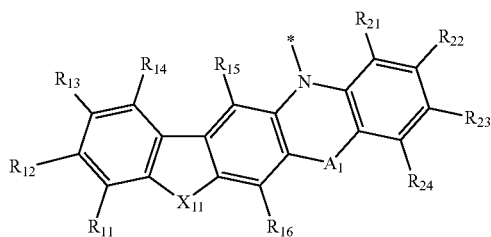

Formula 11-5

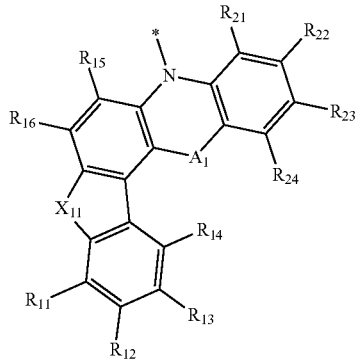

Formula 11-6

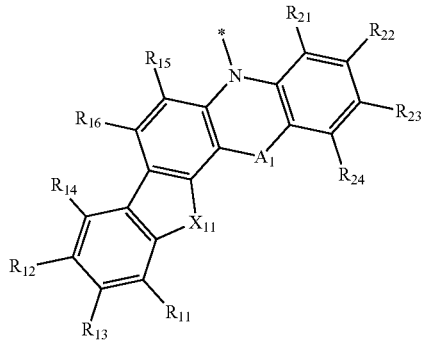

Formula 11-7

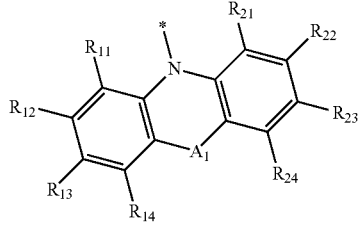

Formula 11-8
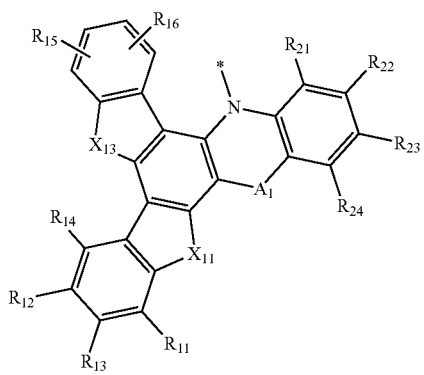
Formula 12-1
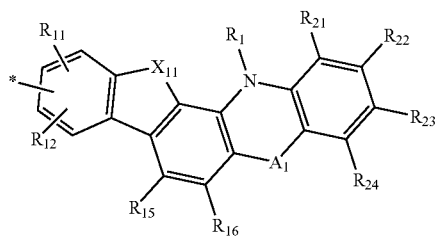
Formula 12-2
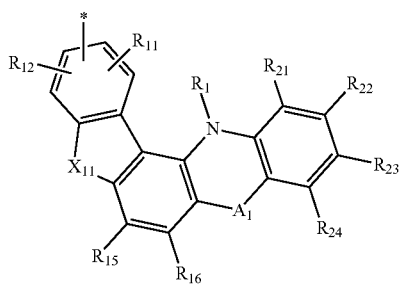
Formula 12-3
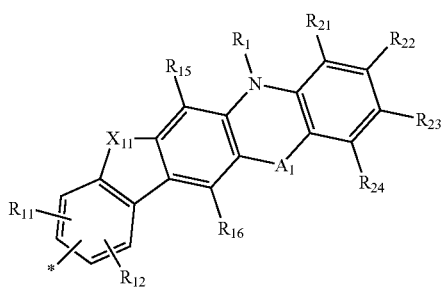
Formula 12-4
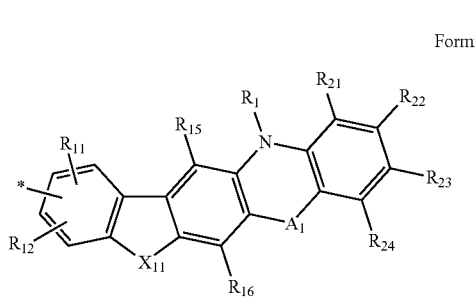
Formula 12-5
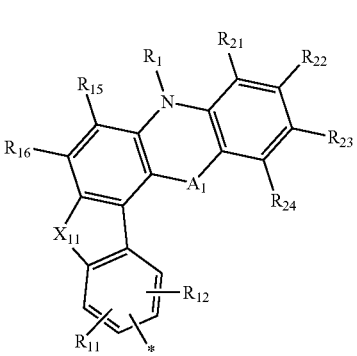
Formula 12-6
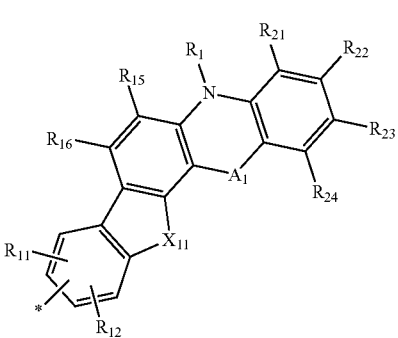
Formula 12-7
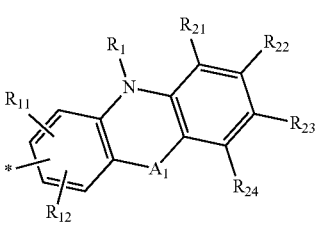
Formula 12-8
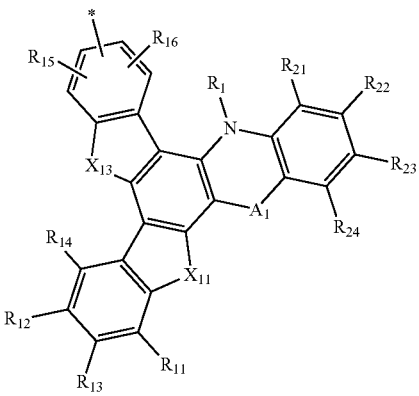
Formula 13-1
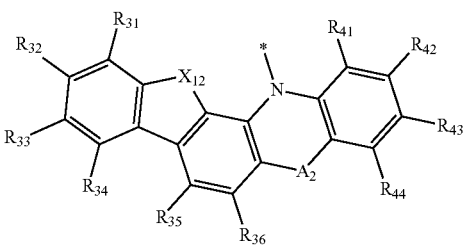

Formula 13-2
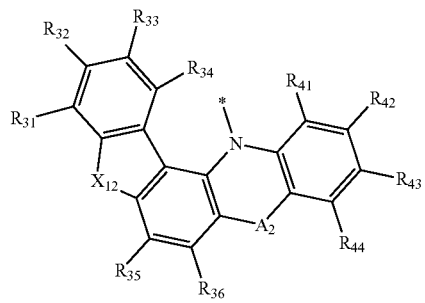
Formula 13-3
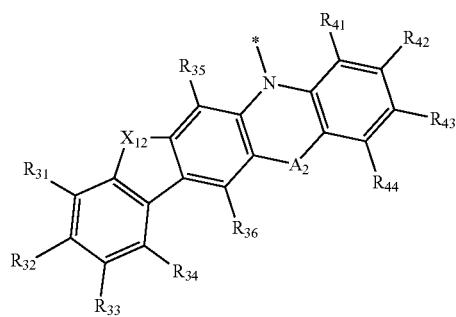
Formula 13-4
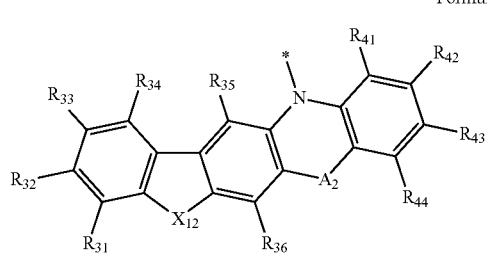
Formula 13-5
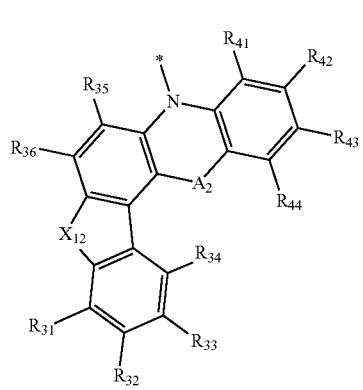
Formula 13-6
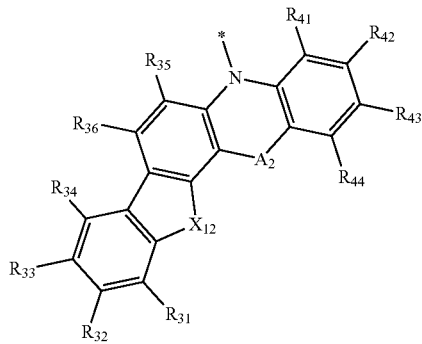
Formula 13-7
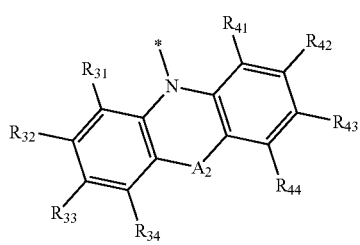
Formula 13-8
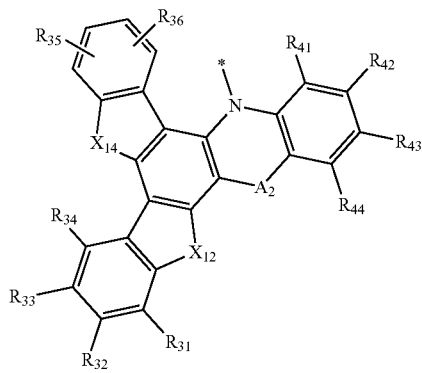
Formula 14-1
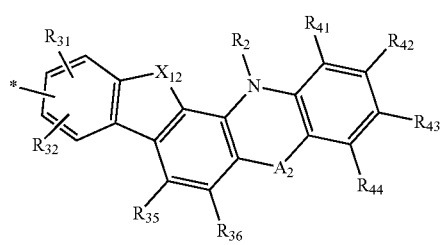
Formula 14-2
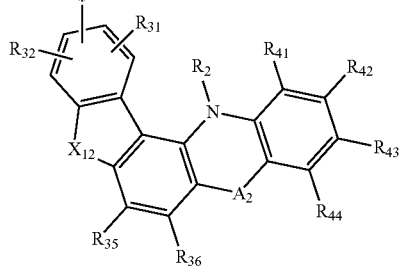

107
-continued

Formula 14-3
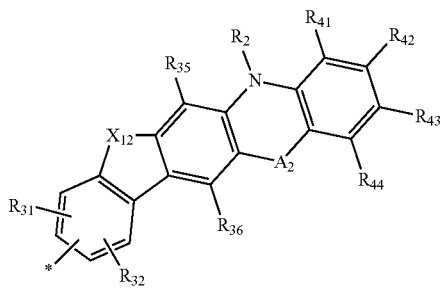

Formula 14-4
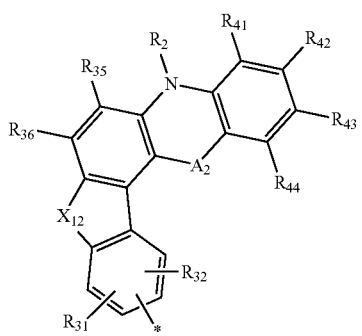

Formula 14-5
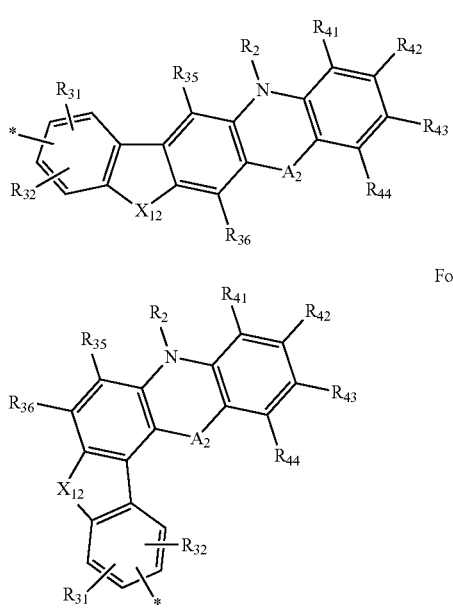

Formula 14-6
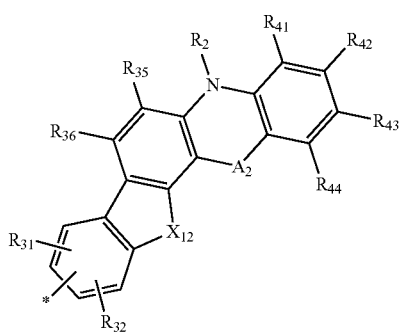

Formula 14-7
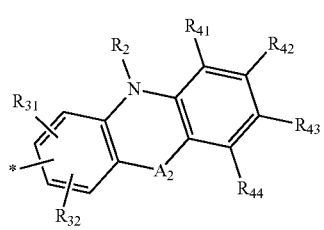

108
-continued

Formula 14-8
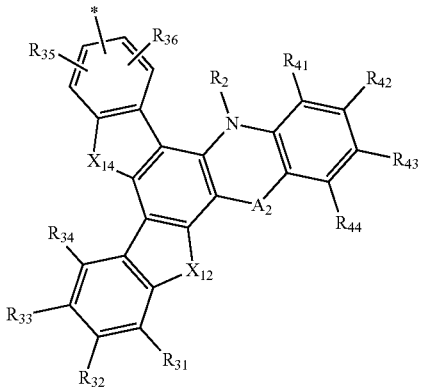

wherein, in Formulae 11-1 to 11-8, 12-1 to 12-8, 13-1 to 13-8, and 14-1 to 14-8, $X_{11}$ and $X_{13}$ are each independently $C(R_{17})(R_{18})$, $N(R_{19})$, O, or S, $X_{12}$ and $X_{14}$ are each independently $C(R_{37})(R_{38})$, $N(R_{39})$, O, or S, $R_1$, $R_2$, $\lambda_1$, and $\lambda_2$ are the same as those groups defined in claim 7, $R_{11}$ to $R_{19}$ are each independently the same as $R_{10}$ defined in claim 7, $R_{21}$ to $R_{24}$ are each independently the same as $R_{20}$ defined in claim 7, $R_{31}$ to $R_{39}$ are each independently the same as $R_{30}$ defined in claim 7, $R_{41}$ to $R_{44}$ are each independently the same as $R_{40}$ defined in claim 7, and

* indicates a binding site to an adjacent atom.

9. The composition of claim 8, wherein $A_1$ is selected from a single bond, a $C_1$-$C_2$ alkylene group, and a $C_2$ alkenylene group; and a $C_1$-$C_2$ alkylene group and a $C_2$ alkenylene group, each substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, and —Si($Q_{21}$)($Q_{22}$)($Q_{23}$), $A_2$ is selected from a single bond, a $C_1$-$C_2$ alkylene group, and a $C_2$ alkenylene group; and a $C_1$-$C_2$ alkylene group and a $C_2$ alkenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —Si($Q_{21}$)($Q_{22}$)($Q_{23}$), and $R_2$, $R_{31}$ to $R_{39}$, and $R_{41}$ to $R_{44}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, and a dibenzothiophenyl group;

a phenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group;

a phenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group; and —Si($Q_1$)($Q_2$)($Q_3$), wherein $Q_1$ to $Q_3$ and $Q_{21}$ to $Q_{23}$ are each independently selected from hydrogen, a $C_1$-$C_{10}$ alkyl group, a $C_1$-$C_{10}$ alkoxy group, a phenyl group, and a naphthyl group.

10. The composition of claim 7, wherein $Ar_1$ is selected from groups represented by Formulae 15-1 to 15-17 and 16-1 to 16-8, $Ar_2$ is selected from groups represented by Formulae 15-1 to 15-17 and 16-1 to 16-8, a phenyl group, and a naphthyl group, and $Ar_{11}$ and $Ar_{12}$ are each independently selected from groups represented by Formulae 17-1 to 17-3:

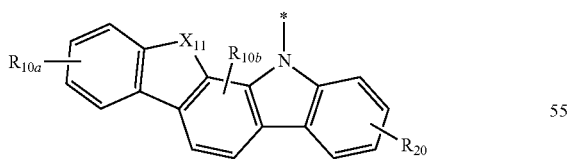

Formula 15-1

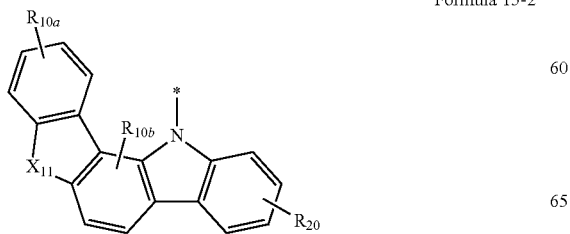

Formula 15-2

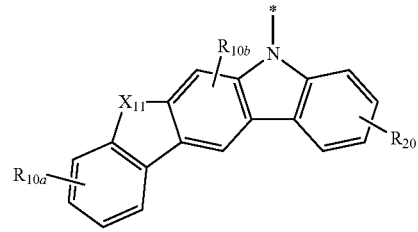

Formula 15-3

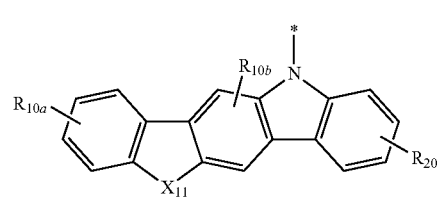

Formula 15-4

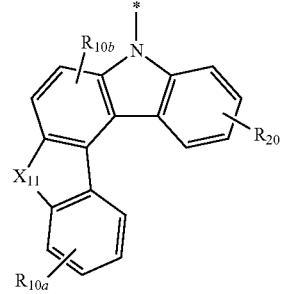

Formula 15-5

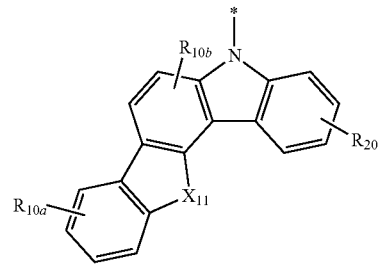

Formula 15-6

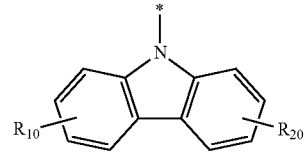

Formula 15-7

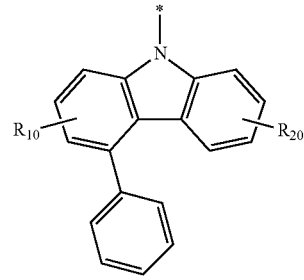

Formula 15-8

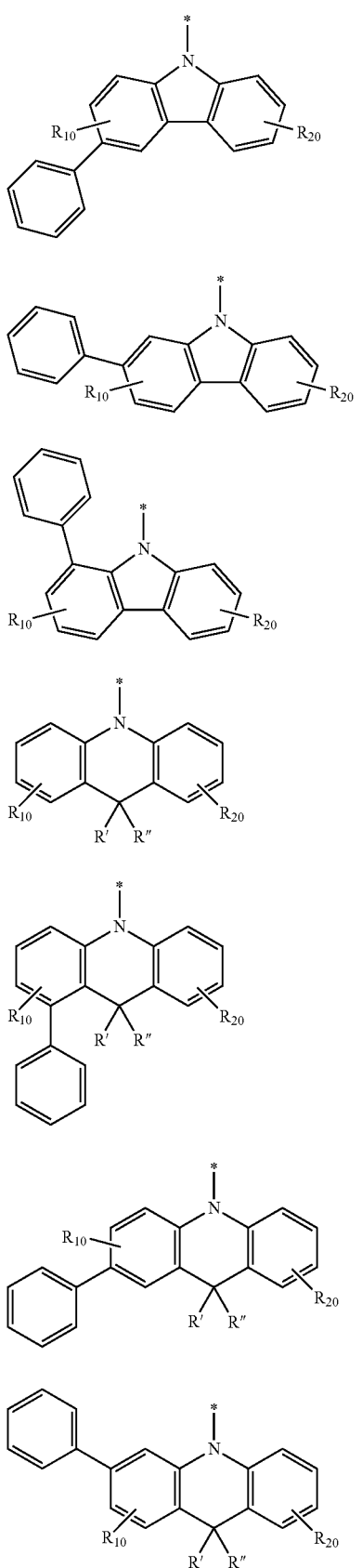
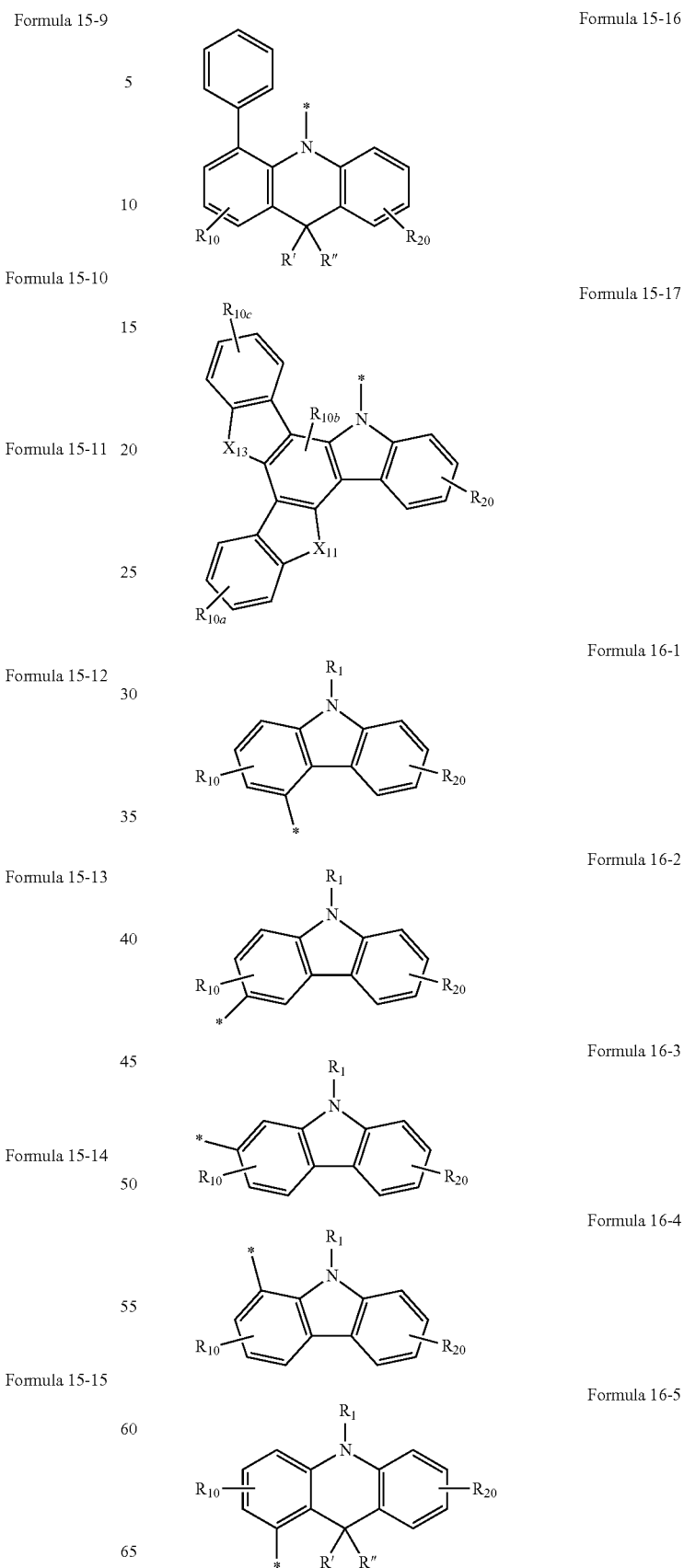

-continued

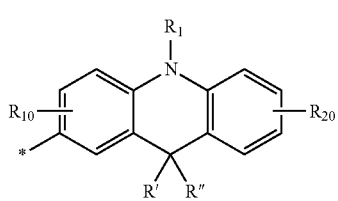
Formula 16-6

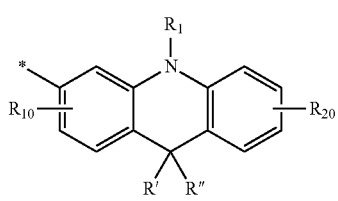
Formula 16-7

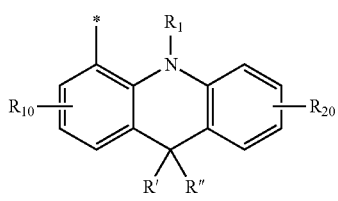
Formula 16-8

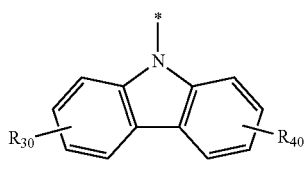
Formula 17-1

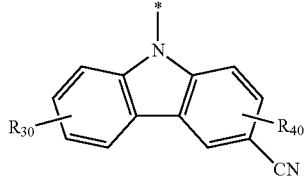
Formula 17-2

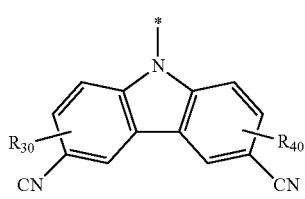
Formula 17-3 wherein, in Formulae 15-1 to 15-17, 16-1 to 16-8, and 17-1 to 17-3, $X_{11}$ and $X_{13}$ are each independently $C(R_{17})(R_{18})$, $N(R_{19})$, O, or S, R' and R" are each independently selected from hydrogen, deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, and a dibenzothiophenyl group, $R_1$, $R_{10}$, $R_{10a}$ to $R_{10c}$, and $R_{20}$ are each independently selected from hydrogen, deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, and —Si($Q_1$)($Q_2$)($Q_3$), and $R_{30}$ and $R_{40}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —CF$_3$, —CF$_2$H, and —CFH$_2$;

a phenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group;

a phenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —CF$_3$, —CF$_2$H, —CFH$_2$, a phenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group; and —Si($Q_1$)($Q_2$)($Q_3$), wherein $Q_1$ to $Q_3$ are each independently selected from hydrogen, a $C_1$-$C_{10}$ alkyl group, a $C_1$-$C_{10}$ alkoxy group, a phenyl group, and a naphthyl group.

11. The composition of claim 7, wherein
i) the donor compound is represented by Formula D-1, provided that the donor compound is selected from compounds in which $L_1$ in Formula D-1 is a single bond; or
ii) the donor compound is selected from compounds represented by Formulae D-1(1) to D-1(52):

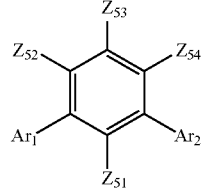
Formula D-1(1)

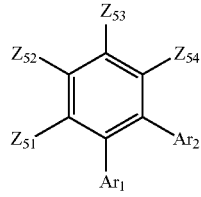
Formula D-1(2)

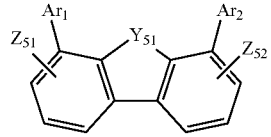
Formula D-1(3)

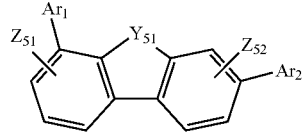
Formula D-1(4)

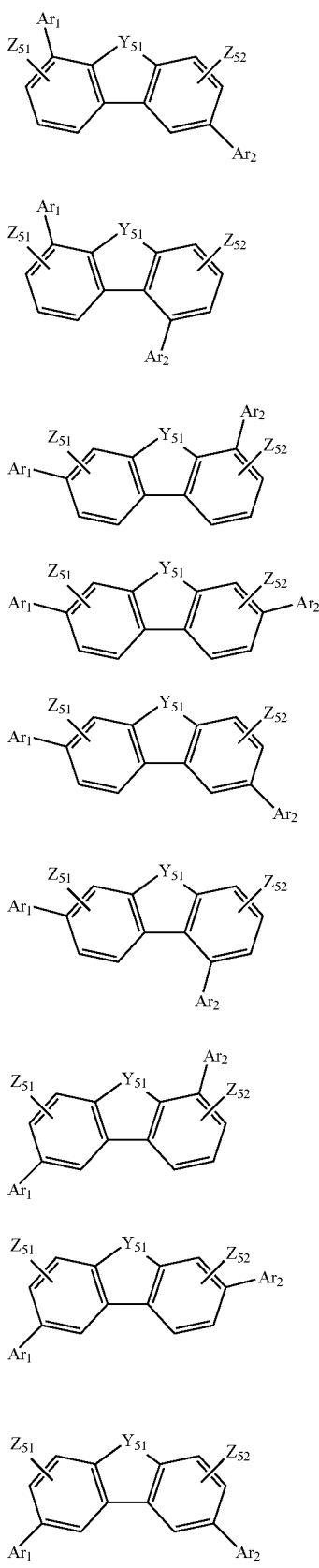
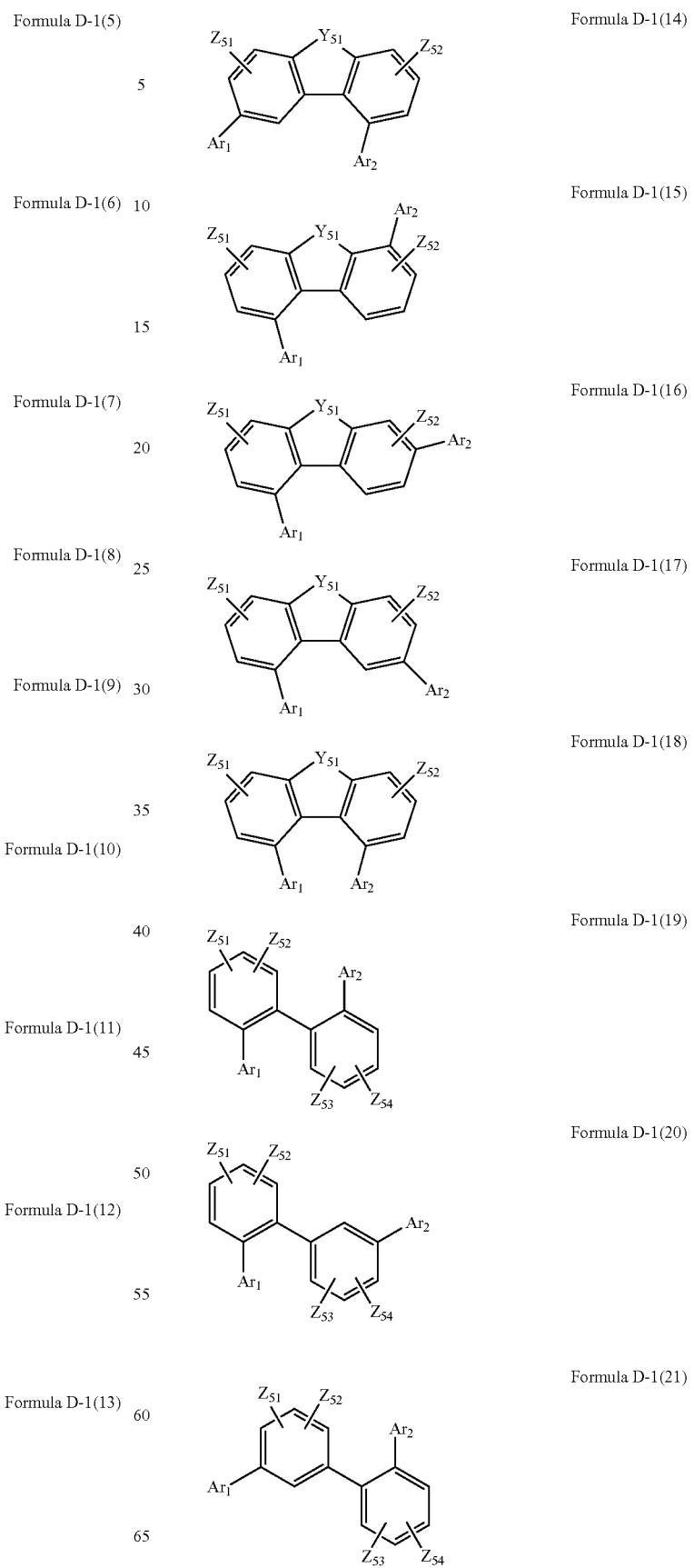

Formula D-1(22)
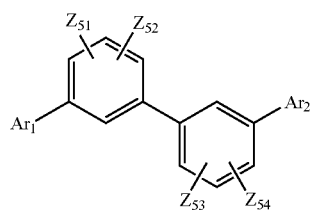
Formula D-1(23)
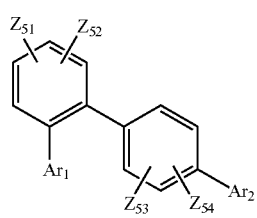
Formula D-1(24)
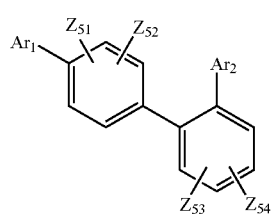
Formula D-1(25)
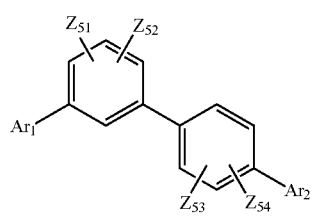
Formula D-1(26)
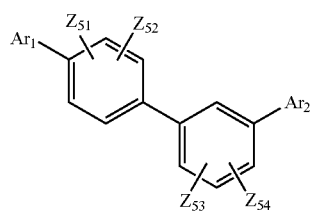
Formula D-1(27)
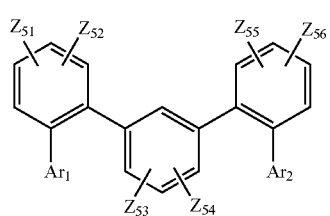
Formula D-1(28)
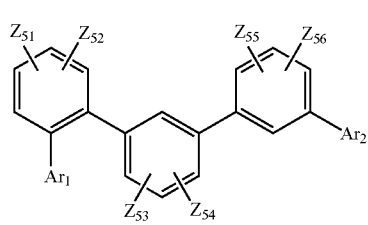
Formula D-1(29)
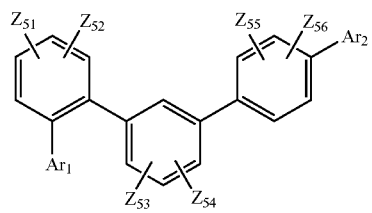
Formula D-1(30)
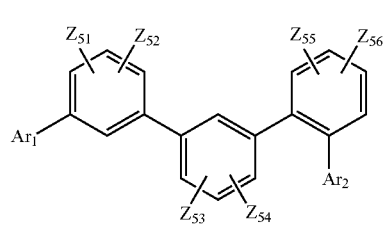
Formula D-1(31)
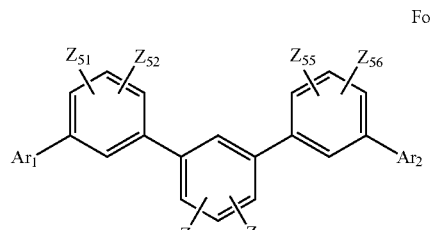
Formula D-1(32)
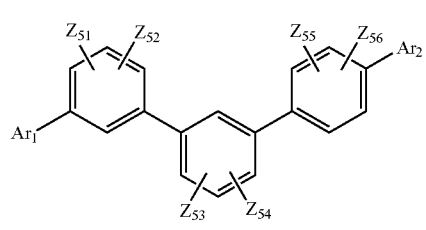
Formula D-1(33)
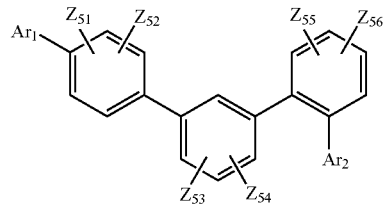
Formula D-1(34)
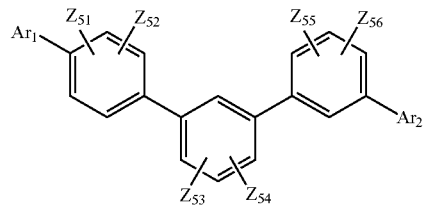
Formula D-1(35)
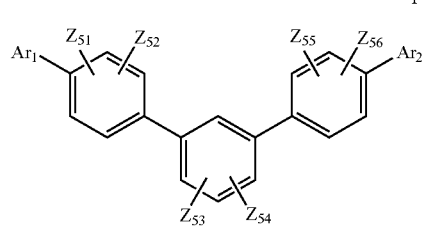

Formula D-1(36)
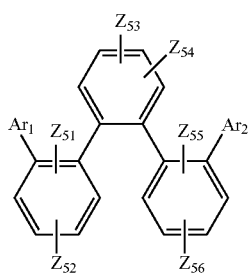
Formula D-1(37)
Formula D-1(38)
Formula D-1(39)
Formula D-1(40)
Formula D-1(41)
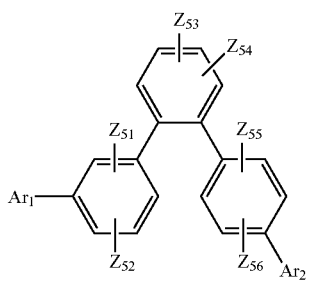
Formula D-1(42)
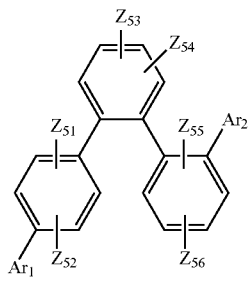
Formula D-1(43)
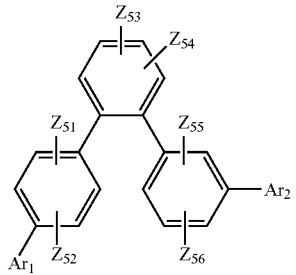
Formula D-1(44)
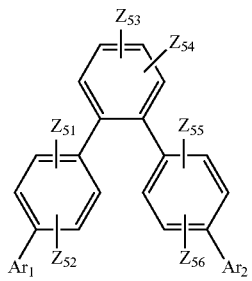
Formula D-1(45)
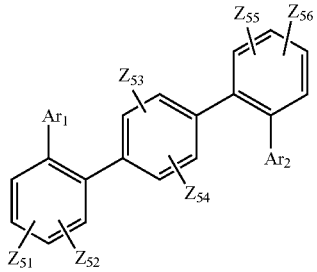

-continued

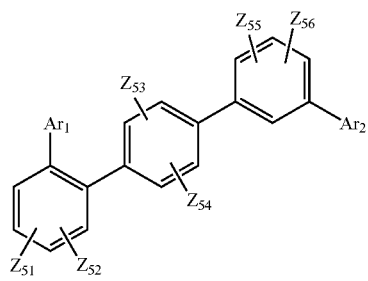
Formula D-1(46)

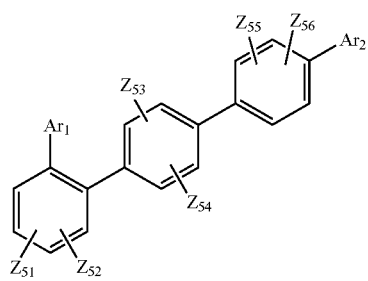
Formula D-1(47)

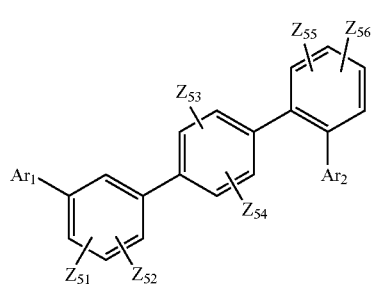
Formula D-1(48)

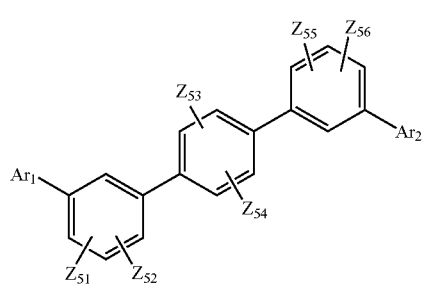
Formula D-1(49)

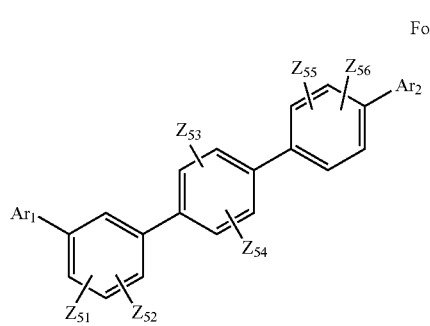
Formula D-1(50)

-continued

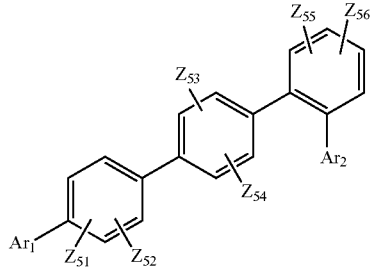
Formula D-1(51)

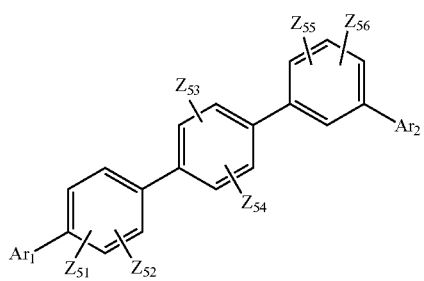
Formula D-1(52)

wherein, in Formulae D-1(1) to D-1(52), $Ar_1$ and $Ar_2$ are the same as those groups defined in claim 7, $Y_{51}$ is each independently $C(Z_{53})(Z_{54})$, $N(Z_{55})$, O, or S, and $Z_{51}$ to $Z_{56}$ are each independently selected from hydrogen, deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, and —Si($Q_{11}$)($Q_{12}$)($Q_{13}$), wherein $Q_{11}$ to $Q_{13}$ are each independently selected from hydrogen, a $C_1$-$C_{10}$ alkyl group, a $C_1$-$C_{10}$ alkoxy group, a phenyl group, and a naphthyl group.

12. The composition of claim 7, wherein $L_{11}$ to $L_{13}$ are each independently selected from groups represented by Formulae 3-1 to 3-56, provided that i) at least one of $L_{11}$ in the number of $a_{11}$, ii) at least one of $L_{12}$ in the number of a12, and iii) at least one of $L_{13}$ in the number of a13 are each independently selected from groups represented by Formulae 3-15 to 3-56:

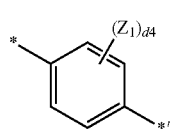
Formula 3-1

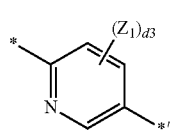
Formula 3-2

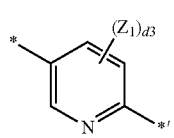
Formula 3-3

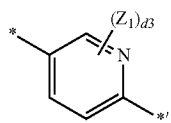
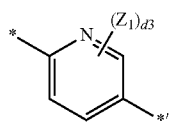
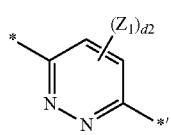
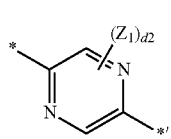
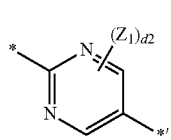
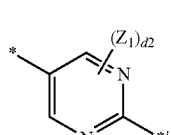
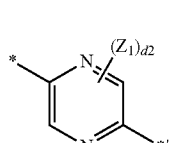
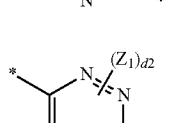
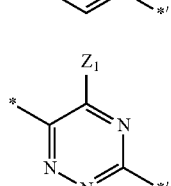
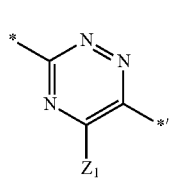
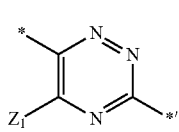
Formula 3-4
Formula 3-5
Formula 3-6
Formula 3-7
Formula 3-8
Formula 3-9
Formula 3-10
Formula 3-11
Formula 3-12
Formula 3-13
Formula 3-14
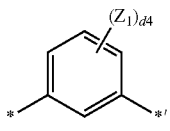
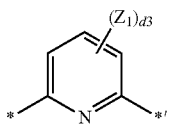
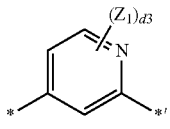
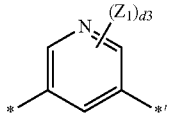
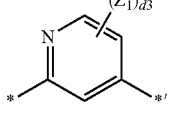
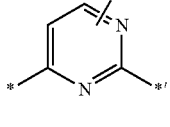
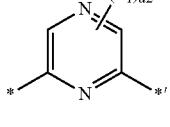
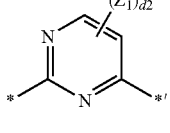
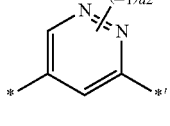
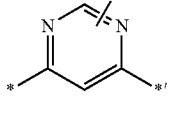
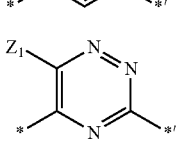
Formula 3-15
Formula 3-16
Formula 3-17
Formula 3-18
Formula 3-19
Formula 3-20
Formula 3-21
Formula 3-22
Formula 3-23
Formula 3-24
Formula 3-25
Formula 3-26

Formula 3-27 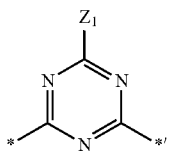
Formula 3-28 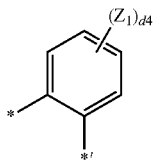
Formula 3-29 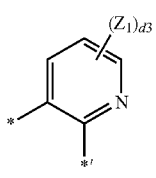
Formula 3-30 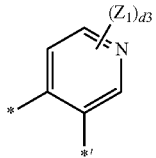
Formula 3-31 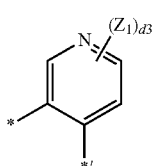
Formula 3-32 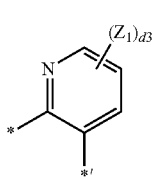
Formula 3-33 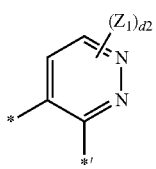
Formula 3-34 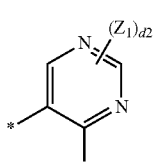
Formula 3-35 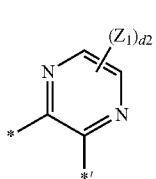
Formula 3-36 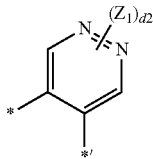
Formula 3-37 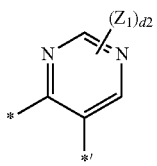
Formula 3-38 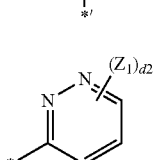
Formula 3-39 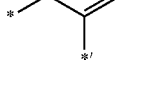
Formula 3-40 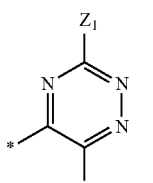
Formula 3-41 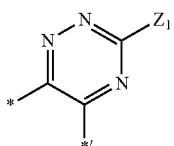
Formula 3-42 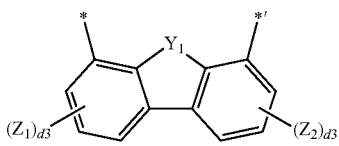
Formula 3-43 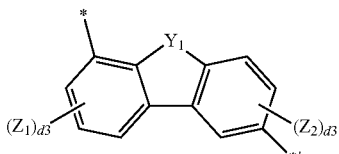
Formula 3-44 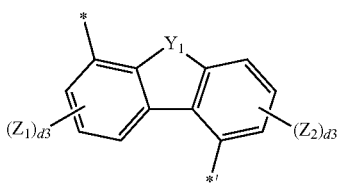

127
-continued

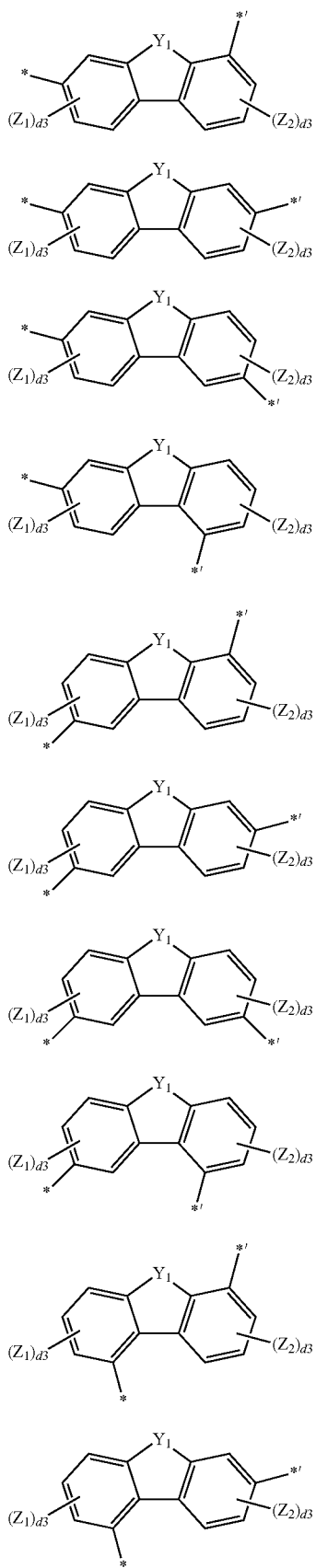

Formula 3-45
Formula 3-46
Formula 3-47
Formula 3-48
Formula 3-49
Formula 3-50
Formula 3-51
Formula 3-52
Formula 3-53
Formula 3-54

128
-continued

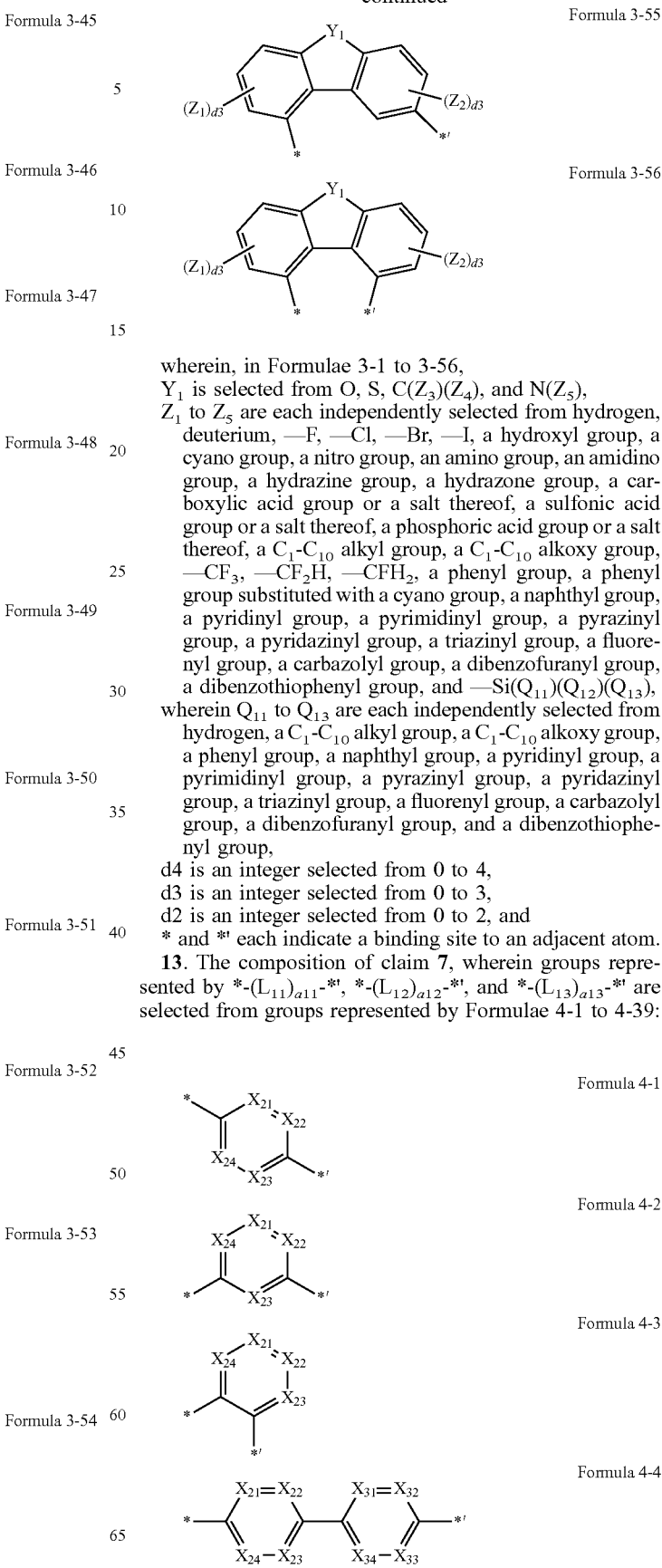

Formula 3-55
Formula 3-56 wherein, in Formulae 3-1 to 3-56,
$Y_1$ is selected from O, S, $C(Z_3)(Z_4)$, and $N(Z_5)$,
$Z_1$ to $Z_5$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, —$CFH_2$, a phenyl group, a phenyl group substituted with a cyano group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —$Si(Q_{11})(Q_{12})(Q_{13})$,
wherein $Q_{11}$ to $Q_{13}$ are each independently selected from hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, and a dibenzothiophenyl group,
d4 is an integer selected from 0 to 4,
d3 is an integer selected from 0 to 3,
d2 is an integer selected from 0 to 2, and
* and *' each indicate a binding site to an adjacent atom.

13. The composition of claim 7, wherein groups represented by *-$(L_{11})_{a11}$-*', *-$(L_{12})_{a12}$-*', and *-$(L_{13})_{a13}$-*' are selected from groups represented by Formulae 4-1 to 4-39:

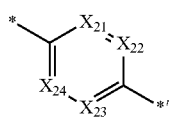

Formula 4-1

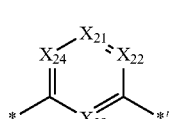

Formula 4-2

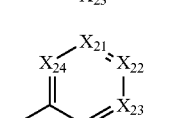

Formula 4-3

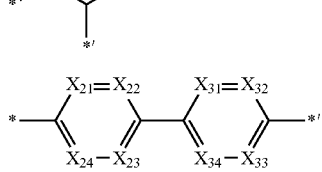

Formula 4-4

129
-continued
Formula 4-5
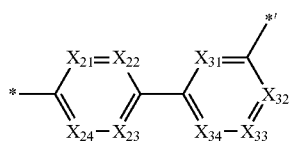
Formula 4-6
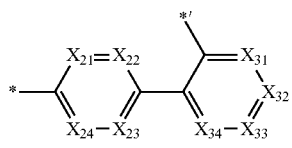
Formula 4-7
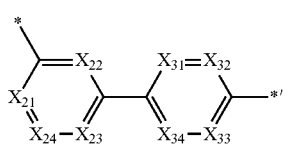
Formula 4-8
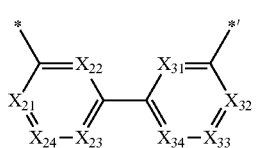
Formula 4-9
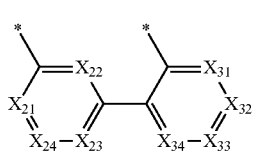
Formula 4-10
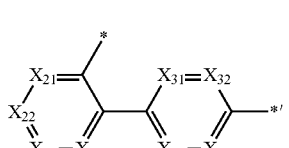
Formula 4-11
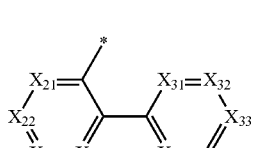
Formula 4-12
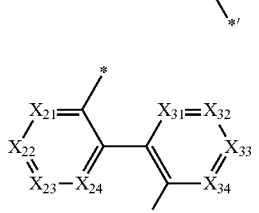
Formula 4-13
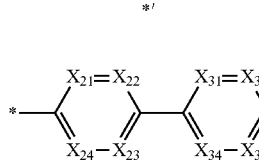
Formula 4-14
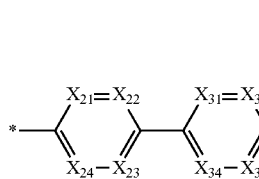
130
-continued
Formula 4-15
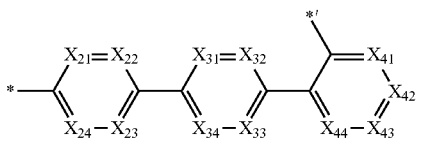
Formula 4-16
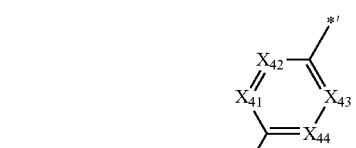
Formula 4-17
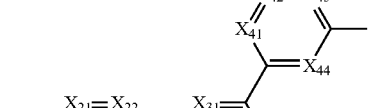
Formula 4-18
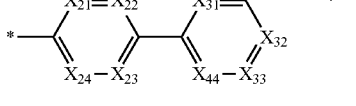
Formula 4-19
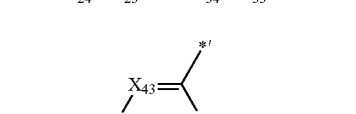
Formula 4-20
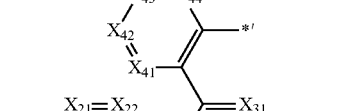
Formula 4-21
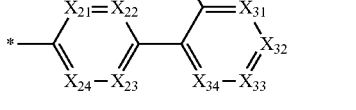

Formula 4-22
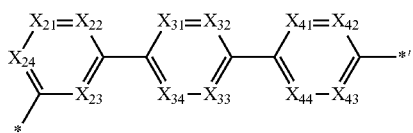
Formula 4-23
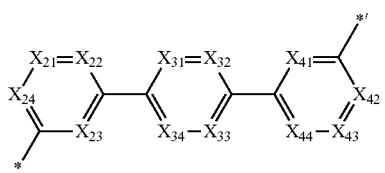
Formula 4-24
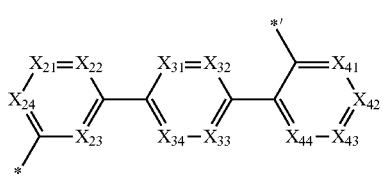
Formula 4-25
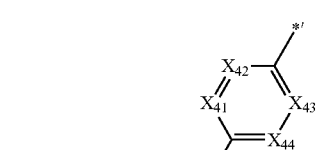
Formula 4-26
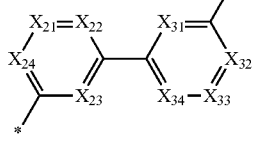
Formula 4-27
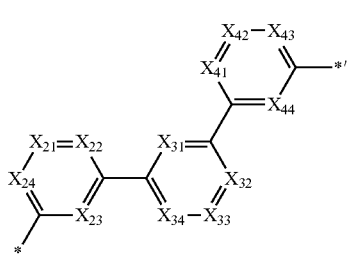
Formula 4-28
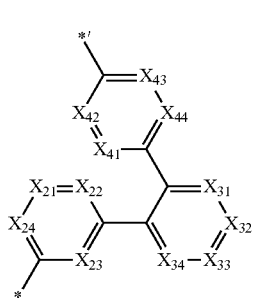
Formula 4-29
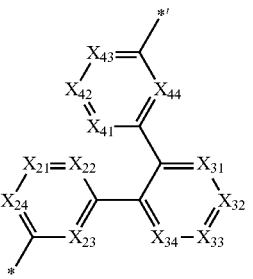
Formula 4-30
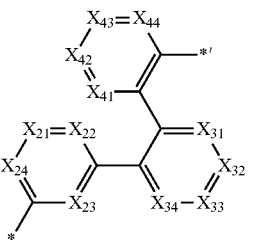
Formula 4-31
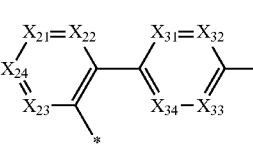
Formula 4-32
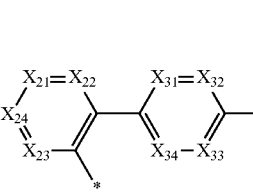
Formula 4-33
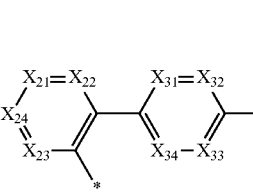
Formula 4-34
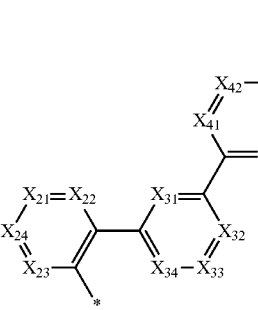
Formula 4-35
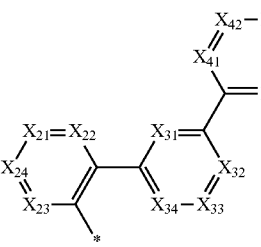

-continued

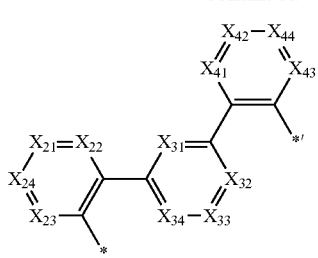

Formula 4-36

Formula 4-37

Formula 4-38

Formula 4-39 wherein, in Formulae 4-1 to 4-39, $X_{21}$ is N or C($Z_{21}$), $X_{22}$ is N or C($Z_{22}$), $X_{23}$ is N or C($Z_{23}$), $X_{24}$ is N or C($Z_{24}$), $X_{31}$ is N or C($Z_{31}$), $X_{32}$ is N or C($Z_{32}$), $X_{33}$ is N or C($Z_{33}$), $X_{34}$ is N or C($Z_{34}$), $X_{41}$ is N or C($Z_{41}$), $X_{42}$ is N or C($Z_{42}$), $X_{43}$ is N or C($Z_{43}$), and $X_{44}$ is N or C($Z_{44}$), provided that at least one of $X_{21}$ to $X_{24}$ are not N, at least one of $X_{31}$ to $X_{34}$ are not N, and at least one of $X_{41}$ to $X_{44}$ are not N, $Z_{21}$ to $Z_{24}$, $Z_{31}$ to $Z_{34}$, and $Z_{41}$ to $Z_{44}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —CF$_3$, —CF$_2$H, —CFH$_2$, a phenyl group, a phenyl group substituted with a cyano group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —Si($Q_{11}$)($Q_{12}$)($Q_{13}$), wherein $Q_{11}$ to $Q_{13}$ are each independently selected from hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, and a dibenzothiophenyl group, and

* and *' each indicate a binding site to an adjacent atom.

14. The composition of claim 1, wherein $T_{11}$ to $T_{16}$ are each independently selected from
hydrogen, deuterium, —F, a cyano group, a $C_1$-$C_{10}$ alkyl group, a $C_1$-$C_{10}$ alkoxy group, —CF$_3$, —CF$_2$H, and —CFH$_2$;
a $C_1$-$C_{10}$ alkyl group and a $C_1$-$C_{10}$ alkoxy group, each substituted with at least one selected from deuterium, —F, a cyano group, —CF$_3$, —CF$_2$H, and —CFH$_2$;
a phenyl group, a pyridinyl group, a pyrimidinyl group, a triazinyl group, a carbazolyl group, a dibenzofuranyl group, and a dibenzothiophenyl group;
a phenyl group, a pyridinyl group, a pyrimidinyl group, a triazinyl group, a carbazolyl group, a dibenzofuranyl group, and a dibenzothiophenyl group, each substituted with at least one selected from deuterium, —F, a cyano group, a $C_1$-$C_{10}$ alkyl group, a $C_1$-$C_{10}$ alkoxy group, —CF$_3$, —CF$_2$H, —CFH$_2$, a phenyl group, a pyridinyl group, a pyrimidinyl group, a triazinyl group, a carbazolyl group, a dibenzofuranyl group, and a dibenzothiophenyl group; and
—Si($Q_1$)($Q_2$)($Q_3$),
wherein $Q_1$ to $Q_3$ are each independently selected from hydrogen, a $C_1$-$C_{10}$ alkyl group, a $C_1$-$C_{10}$ alkoxy group, a phenyl group, a pyridinyl group, a pyrimidinyl group, a triazinyl group, a carbazolyl group, a dibenzofuranyl group, and a dibenzothiophenyl group.

15. The composition of claim 7, wherein
i) the acceptor compound is represented by Formula A-1, provided that the acceptor compound is selected from compounds in which $Ar_{11}$ and $Ar_{12}$ in Formula A-1 are each independently selected from groups represented by Formulae 17-1 to 17-3, and at least one of $Ar_{11}$ and $Ar_{12}$ is selected from groups represented by Formulae 17-2 and 17-3;
ii) the acceptor compound is represented by Formula A-1, provided that the acceptor compound is selected from compounds in which $L_{11}$ in Formula A-1 is selected from groups represented by Formulae 3-15 and 3-28, and at least one of $L_{11}$ in the number of a11 is selected from groups represented by Formulae 6-1 to 6-4; or
iii) the acceptor compound is represented by Formula A-2, provided that the acceptor compound is selected from compounds in which $X_1$ to $X_3$ in Formula A-2 are all N:

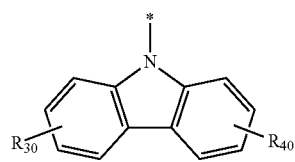

Formula 17-1

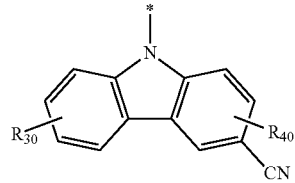

Formula 17-2

-continued

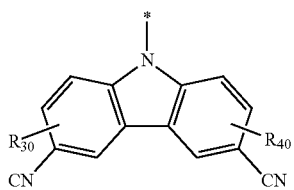

Formula 17-3

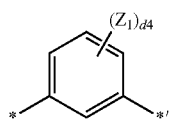

Formula 3-15

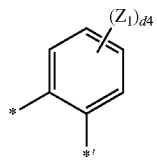

Formula 3-28

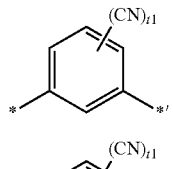

Formula 6-1

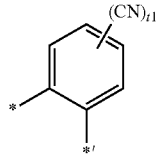

Formula 6-2

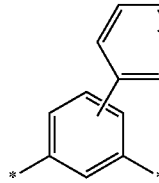

Formula 6-3

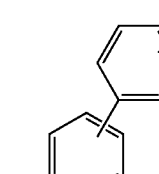

Formula 6-4

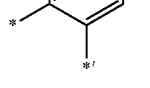

wherein, in Formulae 17-1 to 17-3, 3-15, 3-28, and 6-1 to 6-4, $R_{30}$ and $R_{40}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, and —$CFH_2$;

a phenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group;

a phenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, —$CFH_2$, a phenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group; and —$Si(Q_1)(Q_2)(Q_3)$, $Z_1$ is selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, —$CFH_2$, a phenyl group, a phenyl group substituted with a cyano group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —$Si(Q_{11})(Q_{12})(Q_{13})$, d4 is an integer selected from 0 to 4, t1 is an integer selected from 1 and 2, wherein $Q_1$ to $Q_3$ and $Q_{11}$ to $Q_{13}$ are each independently selected from hydrogen, a $C_1$-$C_{10}$ alkyl group, a $C_1$-$C_{10}$ alkoxy group, a phenyl group, and a naphthyl group, and

* and *' each indicate a binding site to an adjacent atom.

16. The composition of claim 1, wherein the donor compound is selected from Compounds D1 to D16 and the acceptor compound is selected from Compounds A1 to A11:

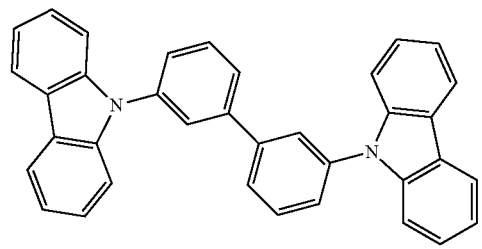

D1

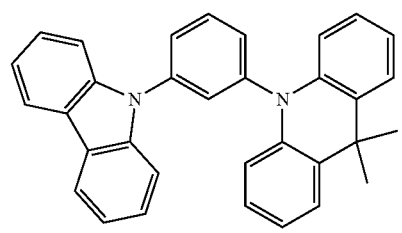

D2

D3
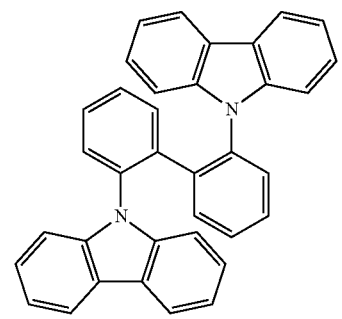
D4
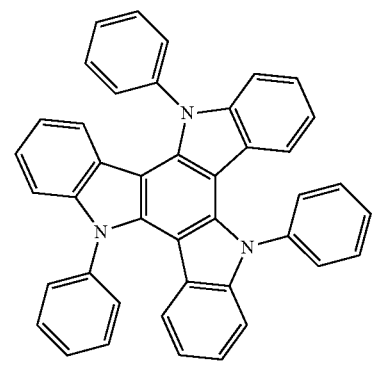
D5
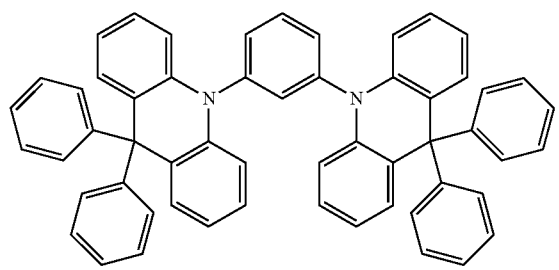
D6
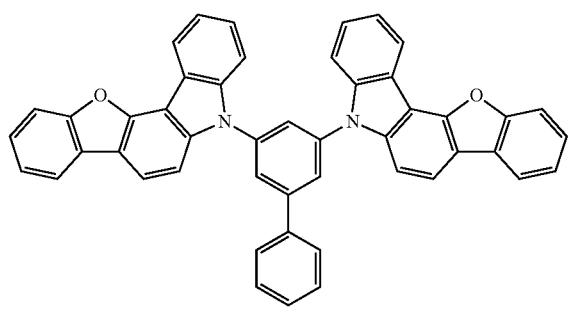
D7
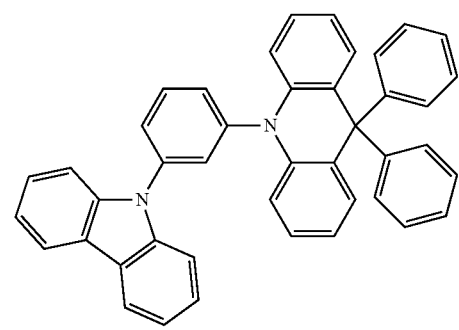
D8
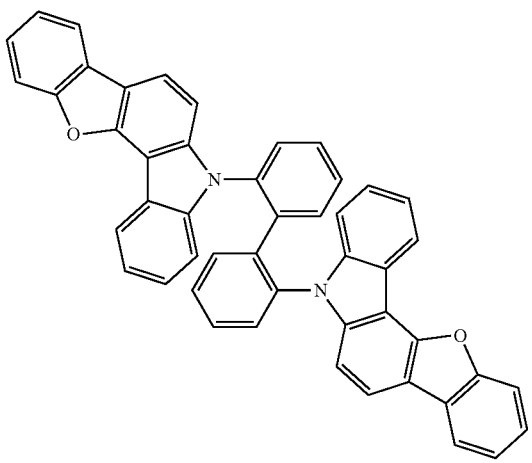
D9
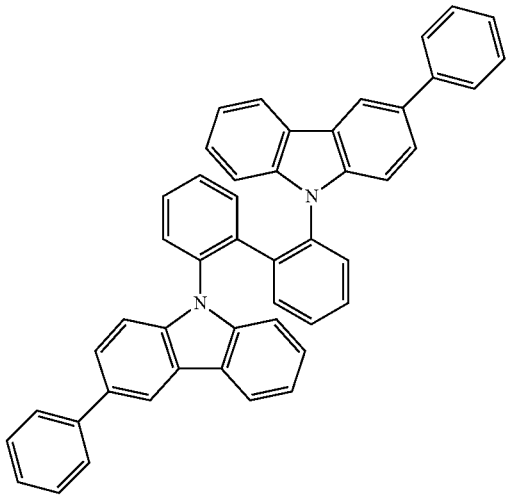
D10
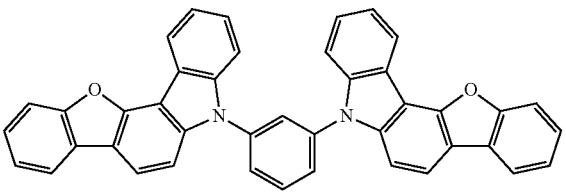
D11
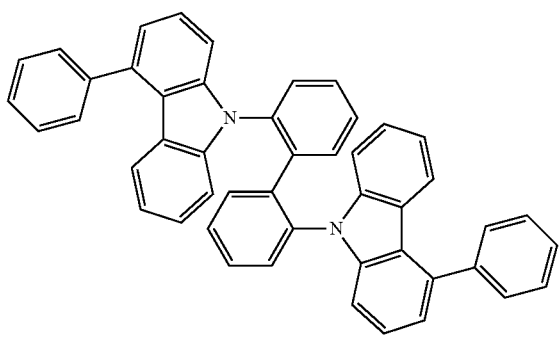

-continued
D12
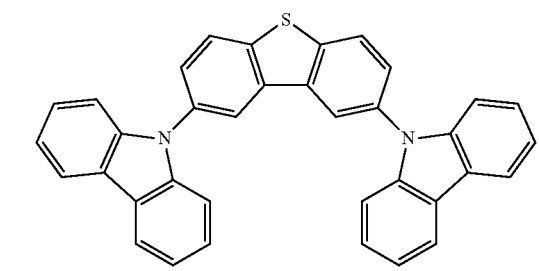
D13
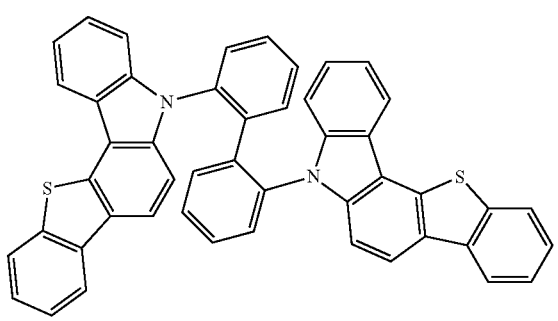
D14
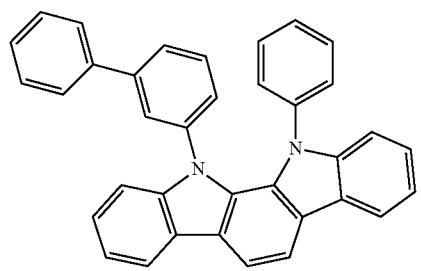
D15
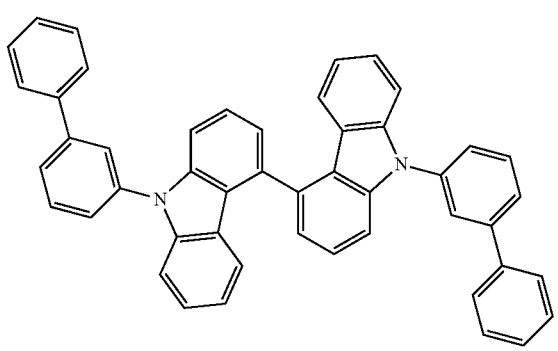
-continued
D16
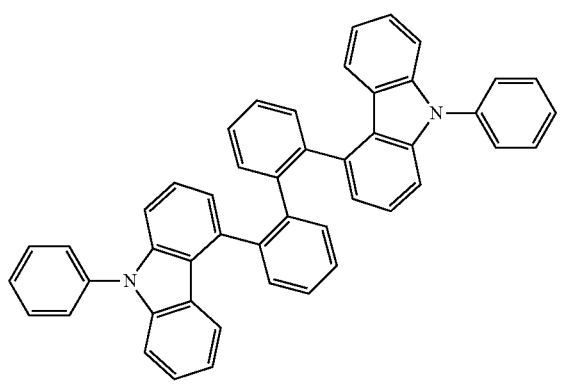
A1
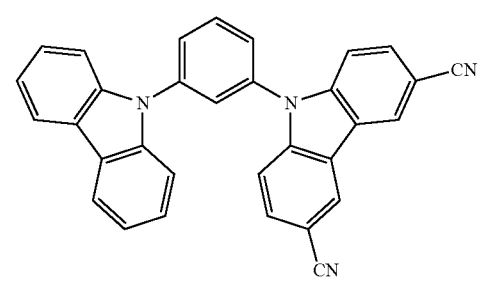
A2
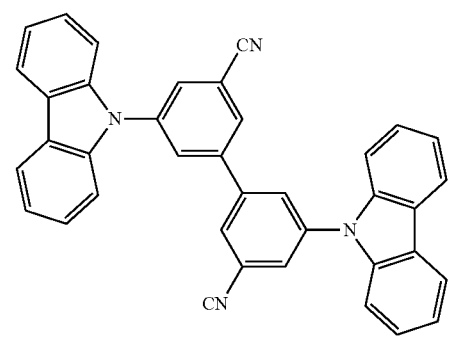
A3
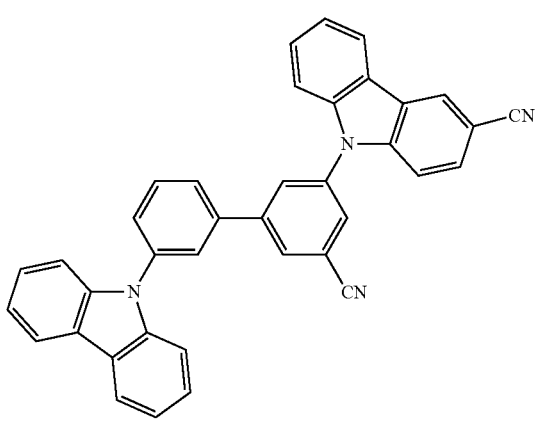

-continued

A4
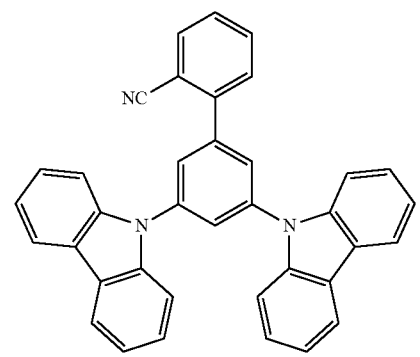

A5
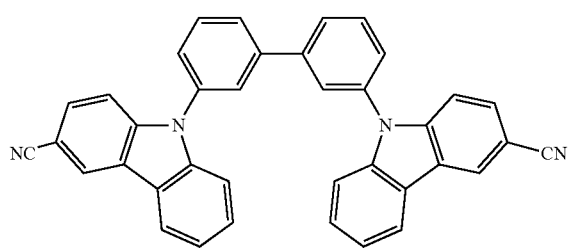

A6
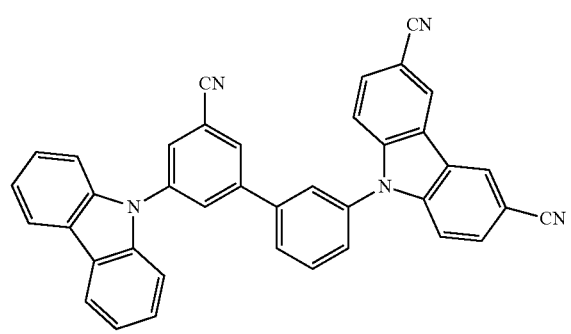

A7
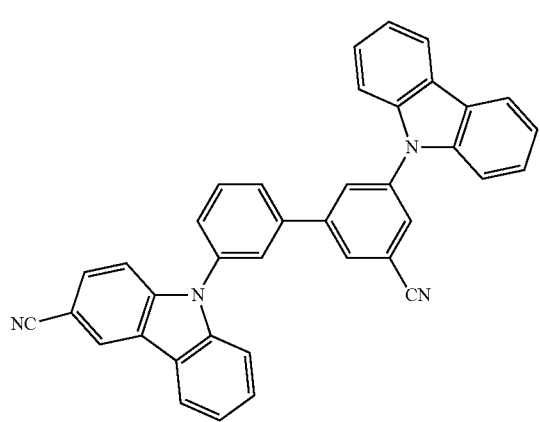

-continued

A8
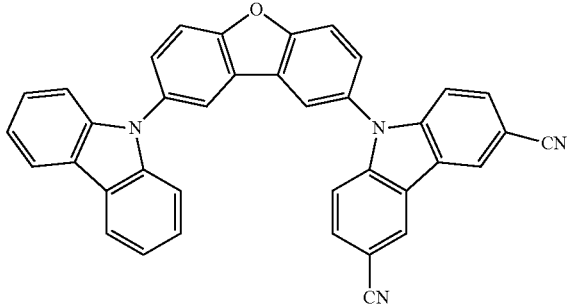

A9
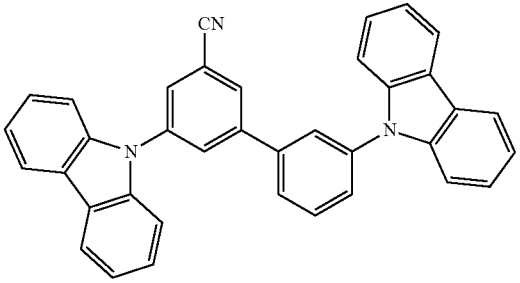

A10
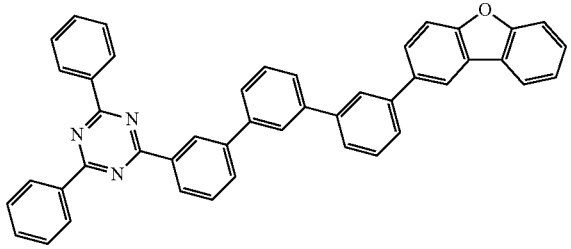

A11
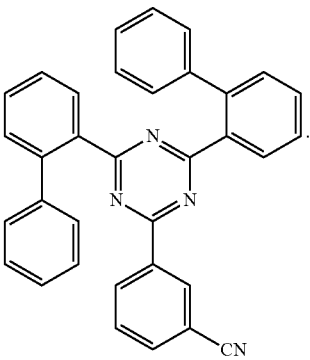

17. A thin film comprising the composition of claim 1.

18. An organic light-emitting device comprising:
a first electrode;
a second electrode; and
an organic layer disposed between the first electrode and the second electrode,
wherein the organic layer comprises a thin film comprising the composition claim 1.

19. The organic light-emitting device of claim 18, wherein the exciplex in the composition is a thermally activated delayed fluorescence emitter.

20. The organic light-emitting device of claim 18,
wherein the thin film comprises the composition of claim 1, and
wherein the thin film is an emission layer.

21. The organic light-emitting device of claim 20,
wherein light emitted from the emission layer is blue light,
wherein a maximum emission wavelength of the blue light is in a range of about 390 nanometers to about 490 nanometers,
wherein X coordinates in CIE color-coordinates of the blue light is a in range of about 0.182 to about 0.307, and
wherein Y coordinates in CIE color-coordinates of the blue light is in a range of about 0.092 to about 0.523.

22. The organic light-emitting device of claim 18, wherein the thin film further comprises a fluorescent dopant.

23. The organic light-emitting device of claim 22, wherein
a maximum emission wavelength $\lambda_{max}(Ex)$ in a photoluminescence spectrum of the exciplex is less than a maximum emission wavelength $\lambda_{max}(FD)$ in a photoluminescence spectrum of the fluorescent dopant,
the photoluminescence spectrum of the exciplex is a spectrum measured at room temperature with respect to a film that is formed by co-deposition of the donor compound and the acceptor compound on a substrate, and
the photoluminescence spectrum of the fluorescent dopant is a spectrum measured at room temperature with respect to a film that is formed by deposition of the fluorescent dopant on a substrate.

24. The organic light-emitting device of claim 23, wherein the fluorescent dopant is selected from compounds represented by Formula 501:

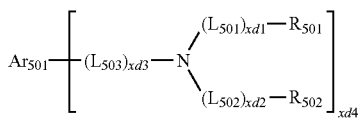

wherein, in Formula 501,
$Ar_{501}$ is selected from
a naphthalene group, a heptalene group, a fluorene group, a spiro-bifluorene group, a carbazole group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group; and
a naphthalene group, a heptalene group, a fluorene group, a spiro-bifluorene group, a carbazole group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, and —Si($Q_{501}$)($Q_{502}$)($Q_{503}$), wherein $Q_{501}$ to $Q_{503}$ are each independently selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group, $L_{501}$ to $L_{503}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $R_{501}$ and $R_{502}$ are each independently selected from
a phenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and
a phenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group,
xd1 to xd3 are each independently selected from 0, 1, 2, and 3, and
xd4 is selected from 0, 1, 2, 3, 4, 5, and 6.

25. The organic light-emitting device of claim 22, wherein the fluorescent dopant comprises at least one compound selected from Compounds FD(1) to FD(5) and FD1 to FD8:

Compound FD(1)
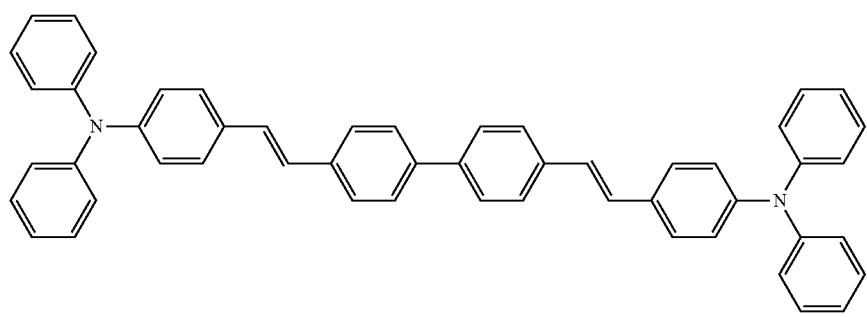
Compound FD(2)
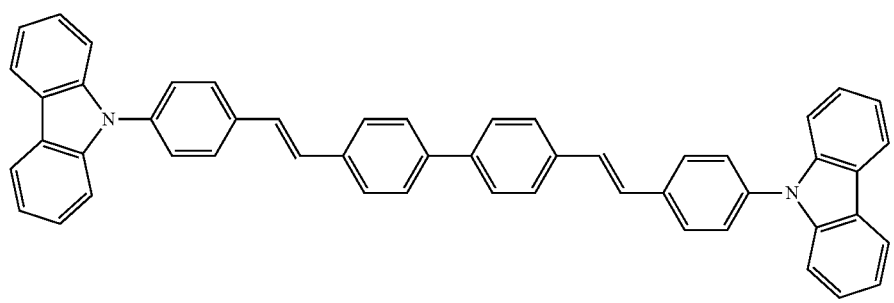
Compound FD(3)
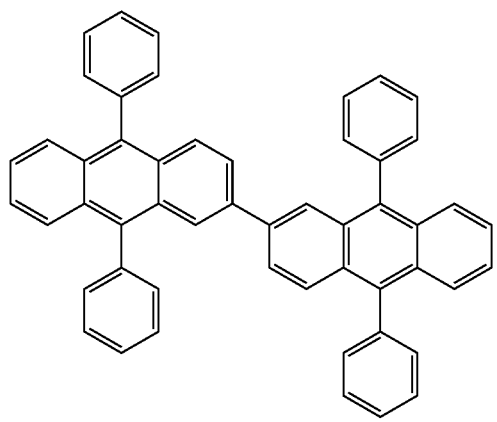
Compound FD(4)
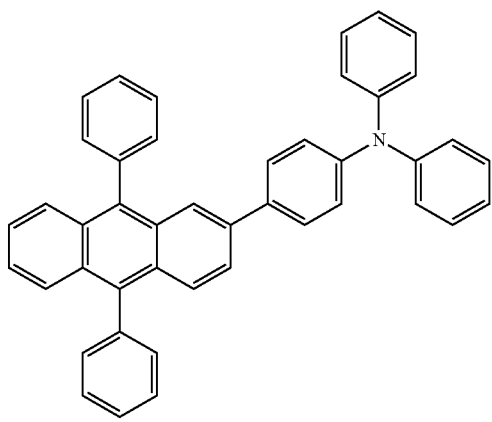
Compound FD(5)
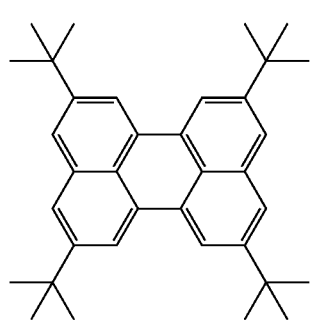
FD1
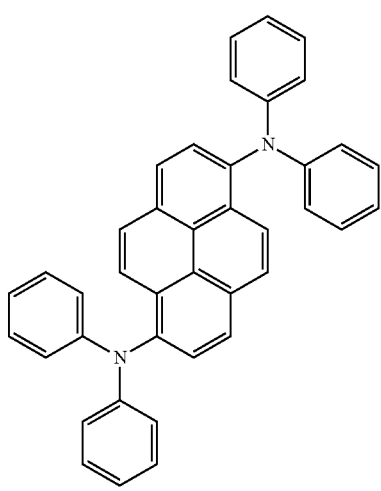

-continued
147
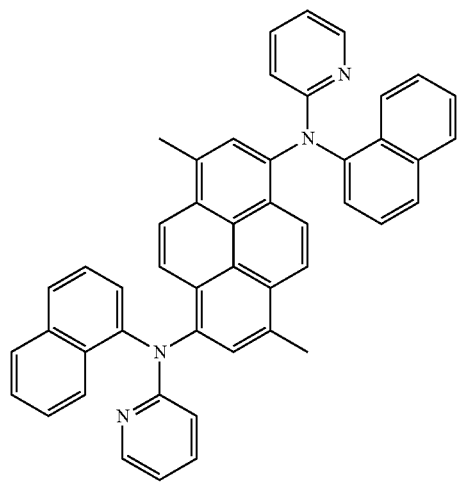
148
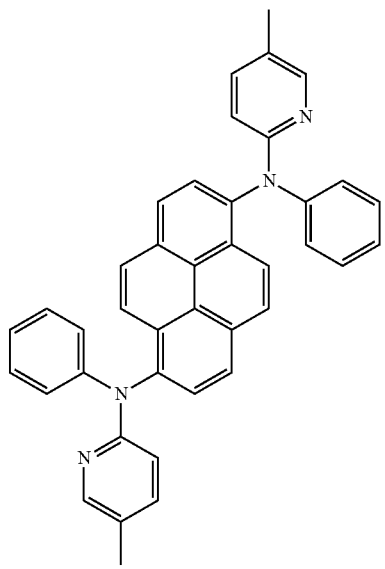
FD2
FD3
FD4
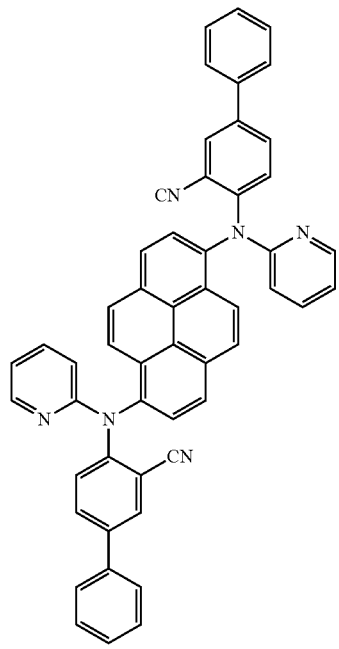
FD5
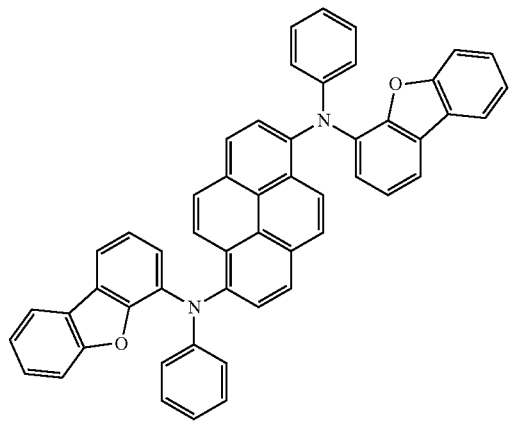
FD6
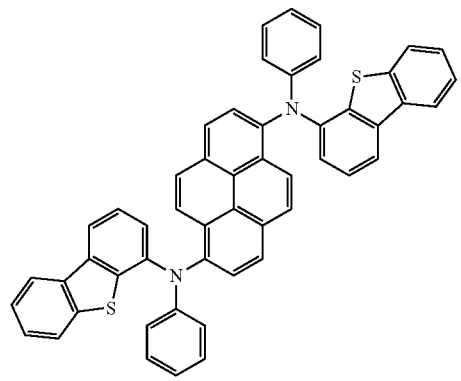
FD7
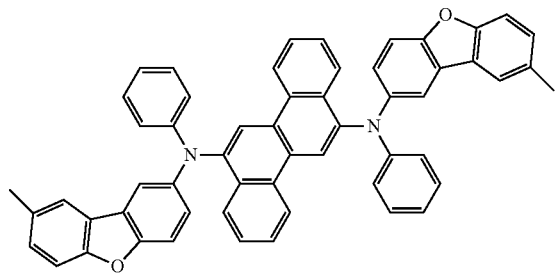

FD8

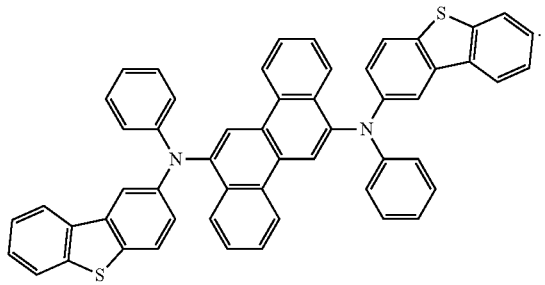

26. A composition comprising:
a donor compound and an acceptor compound,
wherein the donor compound and the acceptor compound form an exciplex,
wherein a maximum emission wavelength $\lambda_{max}$(Ex) in a photoluminescence spectrum of the exciplex is about 390 nanometers or greater and about 490 nanometers or less,
wherein a decay time $T_{decay}$(Ex) of delayed fluorescence in a time-resolved photoluminescence spectrum of the exciplex is about 100 nanoseconds or greater,
wherein a ratio of a delayed fluorescence portion to the overall light-emitting portions in the time-resolved photoluminescence spectrum of the exciplex is about 10% or greater,
wherein a photoluminescence stability of the exciplex is 59% or greater,
wherein the photoluminescence spectrum and the time-resolved photoluminescence spectrum of the exciplex are each a spectrum measured at room temperature with respect to a film that is formed by co-deposition of the donor compound and the acceptor compound on a substrate, and
wherein the photoluminescence stability of the exciplex is calculated according to Equation 10:

PL stability (%)=$(I_2/I_1)$×100     Equation 10 wherein, in Equation 10,
$I_1$ is an intensity of a light at the maximum emission wavelength $\lambda_{max}$(Ex) in a photoluminescence spectrum of Film 1, which is obtained immediately after formation of a film by co-deposition of the donor compound and the acceptor compound on a substrate, measured at room temperature in an inert atmosphere in which external air is excluded, and
$I_2$ is an intensity of a light at the maximum emission wavelength $\lambda_{max}$(Ex) in a photoluminescence spectrum of Film 2, which is obtained after exposure of the Film 1 to pumping laser light used in the evaluation of $I_1$ in an inert atmosphere in which external air is excluded for 3 hours, measured at room temperature in an inert atmosphere in which external air is excluded, wherein
the donor compound does not comprise an electron withdrawing group, and
the acceptor compound comprises at least one electron withdrawing group,
wherein the electron withdrawing group is selected from —F, —CFH$_2$, —CF$_2$H, —CF$_3$, —CN, and —NO$_2$;
a $C_1$-$C_{60}$ alkyl group substituted with at least one selected from —F, —CFH$_2$, —CF$_2$H, —CF$_3$, —CN, and —NO$_2$;
a $C_1$-$C_{60}$ heteroaryl group and a monovalent non-aromatic condensed polycyclic heterocyclic group, each comprising *=N—*' as a ring-forming moiety; and
a $C_1$-$C_{60}$ heteroaryl group and a monovalent non-aromatic condensed polycyclic heterocyclic group, each comprising *=N—*' as a ring-forming moiety and each substituted with at least one selected from deuterium, —F, —CFH$_2$, —CF$_2$H, —CF$_3$, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, and a substituted or unsubstituted monovalent non-aromatic condensed heteropolycyclic group.

* * * * *